United States Patent
Adelfinskaya et al.

(10) Patent No.: US 8,242,087 B2
(45) Date of Patent: Aug. 14, 2012

(54) PHOSPHATE MODIFIED NUCLEOSIDES USEFUL AS SUBSTRATES FOR POLYMERASES AND AS ANTIVIRAL AGENTS

(75) Inventors: Olga Adelfinskaya, San Diego, CA (US); Piet Herdewijn, Wezemaal (BE)

(73) Assignee: K.U.Leuven Research & Development, Leuven (BE)

(*) Notice: Subject to any disclaimer, the term of this patent is extended or adjusted under 35 U.S.C. 154(b) by 449 days.

(21) Appl. No.: 12/549,117

(22) Filed: Aug. 27, 2009

(65) Prior Publication Data

US 2011/0112046 A9  May 12, 2011

Related U.S. Application Data

(63) Continuation-in-part of application No. PCT/EP2008/001764, filed on Feb. 27, 2008.

(30) Foreign Application Priority Data

Feb. 27, 2007 (GB) .................................. 0703715.3
Feb. 27, 2007 (GB) .................................. 0703722.9
Sep. 17, 2007 (GB) .................................. 0718228.0
Sep. 17, 2007 (GB) .................................. 0718229.8
Apr. 30, 2009 (GB) .................................. 0907436.0

(51) Int. Cl.
*A01N 43/04* (2006.01)
*A61K 31/70* (2006.01)

(52) U.S. Cl. ................ 514/43; 514/45; 514/46; 514/47; 514/48; 514/49; 514/50; 514/51

(58) Field of Classification Search ......................... None
See application file for complete search history.

(56) References Cited

U.S. PATENT DOCUMENTS 6,620,796 B1 * 9/2003 Zhou et al. ..................... 514/45

FOREIGN PATENT DOCUMENTS

WO    WO 2008/104408 A2    9/2008

OTHER PUBLICATIONS

Ahmadibeni and Parang, "Solid-Phase Reagents for Selective Monophosphorylation of Carbohydrates and Nucleosides," *J. Org. Chem.* 70:1100-1103, 2005.
Dinkel et al., "Versatile Reagents to Introduce Caged Phosphates," *Tetrahedron Lett.* 44:1153-1155, 2003.
Giraut et al., "Phosphodiester Substrates for Incorporation of Nucleotides in DNA Using HIV-1 Reverse Transcriptase," *Chembiochem* 10:2246-2252, 2009.
Grachev et al., "Formylphenyl Esters of Guanosine-5'-Mono-, Di-, and Triphosphates at the Terminal Phosphate Residue," *Bioorg. Khim.* 16:1379-1385, 1990. (Abstract in English).
International Search Report and Written Opinion for PCT/EP2010/055942 mailed Aug. 25, 2010.

* cited by examiner

*Primary Examiner* — Patrick Lewis
(74) *Attorney, Agent, or Firm* — Clark & Elbing LLP

(57) ABSTRACT

This invention relates to novel phosphate-modified nucleosides, and methods for producing them, being useful for the prevention or treatment of a viral infection in a mammal, and for preparing oligonucleotides by DNA/RNA polymerase-dependent amplification, e.g. PCR.

37 Claims, 12 Drawing Sheets

I  II

SEQUENCE LISTING

<160> NUMBER OF SEQ ID NOS: 8

<210> SEQ ID NO 1
<211> LENGTH: 17
<212> TYPE: DNA
<213> ORGANISM: Artificial Sequence
<220> FEATURE:
<223> OTHER INFORMATION: Primer

<400> SEQUENCE: 1
caggaaacag ctatgac                                                      17

<210> SEQ ID NO 2
<211> LENGTH: 22
<212> TYPE: DNA
<213> ORGANISM: Artificial Sequence
<220> FEATURE:
<223> OTHER INFORMATION: PCR primer

<400> SEQUENCE: 2
cccctgtcat agctgtttcc tg                                                22

<210> SEQ ID NO 3
<211> LENGTH: 44
<212> TYPE: DNA
<213> ORGANISM: Artificial Sequence
<220> FEATURE:
<223> OTHER INFORMATION: Primer

<400> SEQUENCE: 3
cctttgtcat agctgtttcc tccctttgtc atagctgttt cctg                        44

<210> SEQ ID NO 4
<211> LENGTH: 26
<212> TYPE: DNA
<213> ORGANISM: Artificial Sequence
<220> FEATURE:
<223> OTHER INFORMATION: Primer

<400> SEQUENCE: 4 cttttttttgt catagctgtt tcctgc                                           26

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
ttttcgtcat agctgtttcc tg                                                22

<210> SEQ ID NO 6
<211> LENGTH: 26
<212> TYPE: DNA
<213> ORGANISM: Artificial Sequence
<220> FEATURE:
<223> OTHER INFORMATION: Primer

<400> SEQUENCE: 6
aaaaagtcag tcatagctgt ttcctg                                            26

<210> SEQ ID NO 7
<211> LENGTH: 17
<212> TYPE: DNA

```
<213> ORGANISM: Artificial Sequence
<220> FEATURE:
<223> OTHER INFORMATION: Primer

<400> SEQUENCE: 7
gtcatagctg tttcctg                                                    17

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
caggaaacag ctatgactga                                                 20
```

PHOSPHATE MODIFIED NUCLEOSIDES USEFUL AS SUBSTRATES FOR POLYMERASES AND AS ANTIVIRAL AGENTS

CROSS REFERENCE TO RELATED APPLICATIONS

This application is a continuation-in-part of International Application No. PCT/EP2008/001764, filed Feb. 27, 2008, which was published in English under PCT Article 21(2), and which claims the benefit of British Patent Application No. 0703715.3, filed Feb. 27, 2007; British Patent Application No. 0703722.9, filed Feb. 27, 2007; British Patent Application No. 0718228.0, filed Sep. 17, 2007; and British Patent Application No. 0718229.8, filed Sep. 17, 2007, the disclosures of which are incorporated by reference in their entirety.

This application also claims the benefit of British Patent Application No. 0907436.0, filed Apr. 30, 2009, the disclosure of which is incorporated by reference in its entirety.

FIELD OF THE INVENTION

The present invention relates to novel phosphate-modified nucleosides, such as amino acid phosphoramidate nucleosides. The present invention also relates to the phosphate-modified nucleosides as substrates for wild type and/or mutated DNA or RNA polymerases.

The present invention provides for the use of these novel phosphate-modified nucleosides for the production of oligonucleotides such as DNA or RNA and of polypeptides or proteins. The invention also relates to the use of these phosphate-modified nucleosides for growing or selecting specific micro-organisms, such as bacteria. The invention further provides for the use of these novel phosphate-modified nucleosides to treat or prevent viral infections and their use to manufacture a medicine to treat or prevent viral infections, particularly infections with viruses belonging to the HIV family.

The present invention furthermore relates to a method for the production of oligonucleotides, peptides or proteins by using said phosphate-modified nucleosides.

BACKGROUND OF THE INVENTION

There has been significant progress in the design and synthesis of numerous nucleotide analogues bearing a modified nucleobase moiety or unnatural sugar and that are substrates for polymerases. Modifications at the phosphate moiety are introduced to increase the stability of a nucleotide toward enzymatic degradation or to mask the phosphate negative charge and facilitate its penetration into a cell. Common strategy in nucleotide prodrug design is protecting a phosphate moiety with a labile masking group. Removal of a masking group liberates a nucleoside monophosphate entity to be transformed into a nucleoside triphosphate (hereinafter referred as NTP), a substrate for intracellular enzymes. However, even after removal of the masking group, phosphorylation and activation of nucleoside monophosphate remains a problem due to substrate specificity of cellular kinases. Therefore, design of a nucleotide analogue that would allow bypassing the kinase activation pathway while behaving as a direct polymerase substrate would be a considerable challenge.

Treatment of certain viral infections has always been a challenging task due to ability of some viruses to integrate into a host's genome. Therefore, the viral enzymes that are critical for viral genome replication and integration are regarded as the most effective targets for the design of antiviral agents.

A lot of attention has been given to studying mechanisms of action of Human Immunodeficiency Virus (type 1) (HIV-1) and developing specific inhibitors towards this very challenging and important target. One of the enzymes that are essential for the HIV replication is HIV reverse transcriptase (HIV RT). The function of this enzyme is to use a viral RNA genome and a reverse transcriptase to synthesize a double stranded DNA for integration into a host genome. Because this step is critical for the propagation of the viral infection, HIV reverse transcriptase (RT) is an excellent target for antiviral treatment. Currently, two major classes of RT inhibitors (RTIs) exist and are administered for treatment of HIV infection. Non-nucleoside reverse transcriptase inhibitors (NNRTs) are a group of compounds that act through the allosteric inhibition by binding to a hydrophobic site, or a pocket in close proximity to the active site of HIV RT. The other group of RTIs is represented by nucleoside reverse transcriptase inhibitors (NRTIs) that bind directly to the active site and interfere with the polymerization reaction and DNA synthesis.

Nucleoside reverse transcriptase inhibitors are designed to be recognized as substrates for RT and incorporated into a growing strand for further termination of chain elongation. Inhibition of reverse transcriptase activity and chain termination by NRTIs is achieved by introduction of structural modifications to the sugar moiety. The elongation of the DNA strand by a polymerase requires a nucleophilic attack of the 3'-OH group to the a phosphorus atom of an incoming nucleotide. Therefore, nucleoside analogs that lack the 3'-OH group or have it substituted with other functional groups (for instance, $N_3$, F, H) not capable of the nucleophilic attack and formation of phosphodiester bond would act as chain terminators.

Termination of DNA or RNA synthesis with nucleoside analogues is a common and one of the most efficient strategies in the treatment of viral infections, regardless of various side effects and cell toxicity. The therapeutically active form of a nucleoside analogue is a nucleoside triphosphate. However, at the physiological pH nucleoside triphosphates are negatively charged molecules and thus they can not penetrate cellular membranes. Hence, RT inhibitors are usually administered as biologically inactive free nucleosides or as monophosphate prodrugs where a phosphate group is masked with a lipophilic group.

There are three steps of kinase-mediated activation of antiviral nucleosides. At first, transformation to a monophosphate derivative takes place through the action of a cytoplasmic nucleoside kinase (for instance, thymidine kinase and deoxycytidine kinase). Furthermore, a nucleoside 5'-monophosphate kinase catalyzes the conversion of a nucleoside monophosphate to a nucleoside diphosphate. Finally, a diphosphate derivative is phosphorylated by a nucleoside 5'-diphosphate kinase (NDK) to provide an anti-viral nucleoside analog in its activated (phosphorylated) form. The efficiency of phosphorylation depends on substrate specificity of kinases. For instance, in the case of the AZT phosphorylation cascade, conversion from the nucleoside monophosphate to the nucleoside diphosphate becomes a rate limiting step as thymidylate kinase (TMPK) catalyzes this conversion significantly slower than in the case of the natural substrate (TMP). The consequences of this inefficiency are accumulation of AZTMP in the cytosol and decreased therapeutic concentration of AZTTP, the activated nucleoside form. However, it was determined that high levels of AZTMP have an inhibitory effect on thymidylate kinase by competing with its natural substrate (TMP) and resulting in reduced levels of TDP and TTP. Moreover, increased levels of AZT and its phosphorylated derivatives also affect other enzymes of the de novo dNTPs synthesis resulting in skewed natural nucleotide concentrations.

Therefore, administration of free NRTIs, which often relies on intracellular phosphorylation and activation, has significant drawbacks. One of the possible solutions is a prodrug or pronucleotide approach. In the prodrug approach, the monophosphate moiety is "masked" with a labile functional group which also serves to facilitate passage of a "masked" nucleotide inside the cell. Once inside the cell, a masking group is removed either enzymatically or through chemical activation. Removal of the masking group affords a free nucleoside monophosphate intracellularly where it can be further phosphorylated by TMPK and NDK. Thus, although the prodrug approach facilitates delivery of an inhibitory nucleoside inside the cell and eliminates the need for initial phosphorylation by a nucleoside kinase, phosphorylation by TMPK and NDK are still required.

Besides delivery and bio-distribution challenges, another drawback that is often associated with anti-viral therapy is emergence of resistant strains. In the case of HIV-1, the drug resistance is developed by appearance of mutations that would allow HIV RT to discriminate NRTIs for natural nucleotides or remove an incorporated unnatural nucleobase by excision reactions. It has also been shown for herpes simplex virus (HSV) that reduction in anti-herpetic activity of acyclovir, a drug activated by thymidine kinase phosphorylation and commonly used for treatment of HSV infections, is mostly associated with thymidine kinase dependent resistance. Established strategies to manage acyclovir-resistant HSV infections include administration of anti-viral drugs acting directly on a viral DNA polymerase (foscarnet, cidifovir) or by modulating immune response of a patient. However, the later approach is not always feasible and the former one could worsen patient's condition since these medications impose a significant level of toxicity.

Therefore, considering all aforementioned aspects of therapy directed to inhibit viral polymerases and reverse transcriptases, a nucleotide analogue that would not depend on activation by nucleoside/nucleotide kinases whilst serving as a natural substrate mimic, would be of a great interest. In particular, there is a need in the art for the development of novel phosphate-modified nucleosides that meet the requirements for successful polymerase recognition, including good chelating properties and spatial features to form stable enzyme-substrate complexes, and whereby their incorporation reaction into oligonucleotides is not stalled.

SUMMARY OF THE INVENTION

The present invention provides novel phosphate-modified nucleosides which can act as substrates of DNA- or RNA-polymerases and/or as antiviral agents.

The present invention provides novel phosphate-modified nucleosides that can be used as alternative (compared to natural NTPs or dNTPs) substrates for DNA- or RNA-polymerases. In a particular embodiment, these phosphate-modified nucleotides are such that the pyrophosphate group of nucleosides/nucleotides is replaced by a good leaving group, more particularly a leaving group in a nucleotidyl transfer mechanism. In a specific embodiment of the present invention, this leaving group is an amino acid coupled by a phosphoramide binding, yet more particularly this amino acid may be Asp (aspartic acid) or His (histidine), or a close variant thereof, as defined below. In another specific embodiment of the present invention, this leaving group is a carboxylic acid containing group coupled by a phosphoramide binding moiety.

DETAILED DESCRIPTION OF THE INVENTION

A first aspect of this invention relates to novel phosphate-modified nucleosides.

According to one first broad embodiment, the present invention encompasses phosphate-modified nucleosides of (i.e. represented by) the general structural formula A below:

$$R^3O-\underset{R^2}{\overset{\overset{W}{\|}}{P}}-Nuc$$

wherein
Nuc is a natural nucleoside or a nucleoside analogue, wherein said natural nucleoside or nucleoside analogue can be substituted or unsubstituted, thereby creating a phosphonate or phosphate comprising compound;
$R^3$ is independently selected from H (hydrogen); $(C_1-C_6)$ alkyl; $(C_3-C_6)$ cycloalkyl; aryl-$(C_1-C_6)$ alkyl; and 2-cyanoethyl; wherein any such alkyl, cycloalkyl or arylalkyl group may optionally be substituted with 1, 2 or 3 halogen, OH, $(C_1-C_6)$alkoxy, trifluoromethyl, trifluoromethoxy, nitro, cyano, or amino substituents;
W is independently selected from O or S; and
$R^2$ is a group represented by the structural formula V $$\begin{array}{c} \vdots \\ Z \\ | \\ (CH_2)_n \\ | \\ CH \\ / \quad \backslash \\ R^5 \quad R^4 \end{array}$$

wherein
n is 0 or 1;
Z is selected from O; S; or NH;
each of $R^4$ and $R^5$ are independently selected from $(CH_2)_m$—$COOR^6$ and $(CH_2)_m$-imidazolyl;
$R^6$ is selected from H (hydrogen) or $(C_1-C_6)$ alkyl;
m is selected from 0, 1, and 2,
and stereoisomers, enantiomers, pharmaceutically acceptable salts and pro-drugs thereof.

According to a more specific embodiment of this invention, said natural Nucleoside (Nuc) is coupled via its 5' position to the phosphorous atom P in the structural formula A.

Another embodiment of the present invention relates to phosphate-modified nucleotides as defined with reference to the structural formula (I):

$$R^3O-\underset{R^2}{\overset{\overset{W}{\|}}{P}}-O-\underset{OH \quad R^1}{\overset{O}{\bigtriangleup}}B$$

wherein
B is a pyrimidine or purine base, or an analogue thereof, optionally substituted with one or two substituents independently selected from the group consisting of halogen, hydroxyl, sulfhydryl, methyl, ethyl, isopropyl, amino, methylamino, ethylamino, trifluoromethyl and cyano;
$R^1$ is H or OH;
$R^3$ is selected from the group consisting of H, $C_{1-6}$ alkyl, $C_{3-6}$ cycloalkyl, aryl-$C_{1-6}$alkyl and 2-cyanoethyl, wherein said $C_{1-6}$ alkyl, $C_{3-6}$ cycloalkyl or aryl-$C_{1-6}$ alkyl is optionally substituted with one or more, preferably 1, 2 or 3, substituents independently selected from the group consisting of halogen, OH, $C_{1-6}$ alkoxy, trifluoromethyl, trifluoromethoxy, nitro, cyano and amino;
W is O or S; and
$R^2$ is a group represented by the structural formula IV:

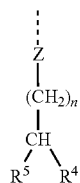

wherein
n is 0 or 1;
Z is selected from the group consisting of O, S, NH and $NCH_3$;
each of $R^4$ and $R^5$ is independently selected from the group consisting of hydrogen, $(CH_2)_m$—$COOR^6$; and $(CH_2)_m$-imidazolyl, provided that $R^4$ and $R^6$ are not both hydrogen;
$R^6$ is H or $C_{1-6}$ alkyl;
m is 0, 1 or 2; and
dotted lines represent the point of attachment of Z to the phosphorous atom P of the structural formula (I);
stereoisomers, enantiomers, pharmaceutically acceptable salts and pro-drugs thereof, provided that said phosphate-modified nucleoside is not:
N-5'-adenylylphosphoramidate L-aspartic acid 1,4-dimethyl ester,
N-5'-uridylylphosphoramidate L-aspartic acid 1,4-dimethyl ester,
N-5'-thimidylylphosphoramidate L-aspartic acid 1,4-dimethyl ester,
N-5'-adenylylphosphoramidate L-aspartic acid 1,4-dimethyl ester, monoammonium salt,
N-5'-guanylylphosphoramidate L-aspartic acid 1,4-dimethyl ester, monoammonium salt,
N-5'-uridylylphosphoramidate L-aspartic acid 1,4-dimethyl ester, monoammonium salt,
N-5'-thymidylylphosphoramidate L-aspartic acid 1,4-dimethyl ester, monoammonium salt,
N-5'-citidylylphosphoramidate L-aspartic acid disodium salt,
N-5'-uridylylphosphoramidate L-histidine
N-5'-uridylylphosphoramidate L-histidine 1-methyl ester,
N-5'-adenylylphosphoramidate L-histidine 1-methyl ester,
N-5'-cytidylylphosphoramidate L-histidine 1-methyl ester, or
N-5'-uridylylphosphoramidate L-aspartic acid.

In the structural formula (I), W is preferably O (oxygen) but it can be replaced by S (sulfur) by chemical reactions well known in the art. According to another embodiment of the present invention, the molecular weight of the group $R_2$ is not above 500.

In a particular embodiment, the present invention also relates to the phosphate-modified nucleosides of the structural formula (I) wherein $R^1$, $R^2$, $R^3$ and W have any of the values or meanings as described herein, and wherein B is adenine; guanine; cytosine; thymine; uracil, or a substituted uracil as described below.

In a particular embodiment, the present invention also relates to the phosphate-modified nucleosides of the structural formula (I) wherein B, $R^1$, $R^2$ and W have any of the values or meanings as described herein, and wherein $R^3$ is H.

In a particular embodiment, the present invention also relates to the phosphate-modified nucleosides of the structural formula (I) wherein B, $R^1$, $R^2$ and $R^3$ have any of the values or meanings as described herein, and wherein W is O.

In a particular embodiment, the present invention also relates to the phosphate-modified nucleosides of the structural formula (I) wherein B, $R^2$, $R^3$ and W have any of the values or meanings as described herein, and wherein $R^1$ is H; and in another particular embodiment, the present invention also relates to the phosphate-modified nucleoside of formula I wherein B, $R^2$, $R^3$ and W have any of the values as described herein, and wherein $R^1$ is OH.

In a particular embodiment, the present invention also relates to the phosphate-modified nucleosides of the structural formula (I) wherein B, $R^1$, $R^2$, $R^3$ and W have any of the values or meanings described herein, and wherein n is 0.

In a particular embodiment, the present invention also relates to the phosphate-modified nucleosides of the structural formula (I) wherein $R^1$, $R^2$, $R^3$ and W have any of the values or meanings described herein, and wherein B is a pyrimidine or purine base analogue as described in the Definitions section below, in particular 5-azapyrimidine, 5-azacytosine, 7-deazapurine, 7-deazaadenine, 7-deazaguanine, or 7-deaza-8-azapurines.

In a particular embodiment of the foregoing, the present invention also relates to the phosphate-modified nucleoside of the structural formula (I) wherein B, $R^1$, $R^3$ and W have any of the values or meanings as described herein, and wherein $R^2$ is a nitrogen-linked natural or synthetic amino acid; and in another particular embodiment, said amino acid is linked via its $\alpha$-$NH_2$ group. In yet another particular embodiment, said amino acid is linked via its $\alpha$-$NH_2$ group, whereby the H group of the NH-linking group is substituted by a methyl group.

In a more particular embodiment of the invention, said amino acid is selected from Asp or His. In another particular embodiment of the invention, said amino acid is selected from the group consisting of L-alanine, D-alanine, beta-alanine and N-methyl beta-alanine (3-(methylamino)propionic acid).

In yet another particular embodiment of the invention, said amino acid is in the L conformation.

In another particular embodiment of the invention, with reference to formula (IV), Z is O; NH or $NCH_3$.

In yet another particular embodiment of the invention, $R^4$ is COOH and $R^5$ is selected from $CH_2$—COOH or $CH_2$-4-imidazolyl.

In a yet more particular embodiment of the invention, $R^3$ is H and $R^2$ is according to formula IV, wherein Z is NH or $NCH_3$, $R^4$ is COOH and $R^5$ is $CH_2$—COOH or $CH_2$-4-imidazolyl.

In yet another particular embodiment, the present invention relates to phosphate-modified nucleosides according to the structural formula (I), wherein $R^3$ is H and $R^2$ is an amino acid coupled to the phosphor atom through its amino function, more particularly said amino acid is Aspartic acid (Asp), Histidine (His) or methyl-aspartic acid.

In a particular embodiment, the novel phosphate-modified nucleoside is 2'-deoxy-adenosine-5'-aspartyl-phosphoramidate (Asp-dAMP), 2'-deoxy-cytidine-5'-aspartyl-phosphoramidate (Asp-dCMP), 2'-deoxy-guanosine-5'-aspartyl-phosphor-amidate (Asp-dGMP), 2'-deoxy-thymidine-5'-aspartyl-phosphoramidate (Asp-dTMP), 2'-deoxy-uridine-5'-aspartyl-phosphoramidate (Asp-dUMP), 2'-deoxyadenosine-5'-N-methylaspartyl-phosphoramidate, 2'-deoxycytidine-5'-N-methylaspartyl-phosphor-amidate, 2'-deoxycytidine-5'-N-methylaspartyl-phosphoramidate, 2'-deoxyguanosine-5'-N-methylaspartyl-phosphoramidate, 2'-deoxythymidine-5'-N-methylaspartyl-phosphoramidate or 2'-deoxyuridine-5'-N-methylaspartyl-phosphoramidate.

In another particular embodiment, the novel phosphate-modified nucleoside is 2'-deoxy-adenosine-5'-histidyl-phosphoramidate (His-dAMP), 2'-deoxy-cytidine-5'-histidyl-phosphoramidate (His-dCMP), 2'-deoxy-guanosine-5'-histidyl-phosphor-amidate (His-dGMP), 2'-deoxy-thymidine-5'-histidyl-phosphoramidate (His-dTMP), 2'-deoxy-uridine-5'-histidyl-phosphoramidate (His-dUMP), 2'-deoxyadenosine-5'-N-methylhistidyl-phosphoramidate, 2'-deoxycytidine-5'-N-methylhistidyl-phosphor-amidate, 2'-deoxycytidine-5'-N-methylhistidyl-phosphoramidate, 2'-deoxyguanosine-5'-N-methylhistidyl-phosphoramidate, 2'-deoxythymidine-5'-N-methylhistidyl-phosphoramidate or 2'-deoxyuridine-5'-N-methylhistidyl-phosphoramidate.

In another particular embodiment, the novel phosphate-modified nucleoside is adenosine-5'-aspartyl-phosphoramidate (Asp-AMP), cytidine-5'-aspartyl-phosphor-amidate (Asp-CMP), guanosine-5'-aspartyl-phosphoramidate (Asp-GMP), 5-methyluridine-5'-aspartyl-phosphoramidate (Asp-m5uMP), uridine-5'-aspartyl-phosphoramidate (Asp-UMP), adenosine-5'-N-methylaspartyl-phosphoramidate, cytidine-5'-N-methylaspartyl-phosphoramidate, cytidine-5'-N-methylaspartylphosphoramidate, guanosine-5'-N-methylaspartyl-phosphoramidate, uridine-5'-N-methyl-aspartyl-phosphoramidate or 5-methyluridine-5'-N-methylaspartyl-phosphoramidate.

In another particular embodiment, the novel phosphate-modified nucleoside is adenosine-5'-histidyl-phosphoramidate (His-AMP), cytidine-5'-histidyl-phosphor-amidate (His-CMP), guanosine-5'-histidyl-phosphoramidate (His-GMP), 5-methyluridine-5'-histidyl-phosphoramidate (His-m5uMP), uridine-5'-histidyl-phosphor-amidate (His-UMP), adenosine-5'-N-methylhistidyl-phosphoramidate, cytidine-5'-N-methylhistidyl-phosphoramidate, cytidine-5'-N-methylhistidyl-phosphoramidate, guanosine-5'-N-methylhistidyl-phosphoramidate, uridine-5'-N-methylhistidyl-phosphoramidate or 5-methyluridine-5'-N-methylhistidyl-phosphoramidate.

According to a second broad embodiment, the present invention encompasses phosphate-modified nucleosides represented by the structural formula A'

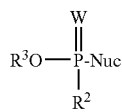

wherein
Nuc is a natural nucleoside or a nucleoside analogue, wherein said natural nucleoside or nucleoside analogue can be substituted or unsubstituted, thereby creating a phosphonate or phosphate comprising compound;

$R^3$ is selected from the group consisting of hydrogen, ($C_1$-$C_6$) alkyl, ($C_3$-$C_6$) cycloalkyl, aryl-($C_1$-$C_6$) alkyl, and 2-cyanoethyl; wherein any of such alkyl, cycloalkyl or arylalkyl may optionally be substituted with 1, 2 or 3 substituents independently selected from the group consisting of halogen, hydroxyl, ($C_1$-$C_6$) alkoxy, trifluoromethyl, trifluoromethoxy, nitro, cyano and amino;

W is O or S;

$R^2$ is a group represented by the structural formula (VI)

wherein
dotted lines represent the point of attachment of Z to the phosphorous atom of formula A';
n is 0, 1 or 2;
Z is selected from the group consisting of O, S, NH and NCH$_3$; and
Ar is an aryl group such as defined below, and stereoisomers, enantiomers, pharmaceutically acceptable salts and pro-drugs thereof.

According to a more specific embodiment of this invention, said natural Nucleoside (Nuc) is coupled via its 5' position to the phosphor atom P in formula A'.

Another embodiment of the present invention relates to phosphate-modified nucleosides with reference to the structural formula (I'):

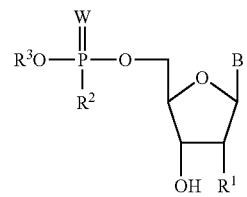

wherein
B is a pyrimidine or purine base, or an analogue thereof, optionally substituted with one or two substituents independently selected from the group consisting of halogen, hydroxyl, sulfhydryl, methyl, ethyl, isopropyl, amino, methylamino, ethylamino, trifluoromethyl and cyano;

$R^1$ is hydrogen or hydroxyl;

$R^3$ is selected from the group consisting of hydrogen, $C_{1-6}$ alkyl, $C_{3-6}$ cycloalkyl, aryl-$C_{1-6}$alkyl and 2-cyanoethyl, wherein said $C_{1-6}$ alkyl, $C_{3-6}$ cycloalkyl or aryl-$C_{1-6}$ alkyl is optionally substituted with one or more, preferably 1, 2 or 3, substituents independently selected from the group consisting of halogen, hydroxyl, $C_{1-6}$ alkoxy, trifluoromethyl, trifluoromethoxy, nitro, cyano and amino;

W is O or S; and
R² is a group represented by the structural formula (VI)

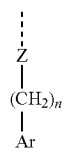
(VI)

wherein
  dotted lines represent the point of attachment of Z to the phosphorous atom of formula (I');
  n is 0, 1 or 2;
  Z is selected from the group consisting of O, S, NH and NCH₃; and
  Ar is an aryl group such as defined below,
and stereoisomers, enantiomers, pharmaceutically acceptable salts and pro-drugs thereof.

In the structural formulae (A') and (I'), W is preferably O but it can be replaced by S by chemical reactions well known in the art. According to a specific embodiment of the invention, the molecular weight of $R_2$ is not above 500.

In a particular embodiment, the present invention also relates to the phosphate-modified nucleosides represented by the structural formula (I') wherein $R^1$, $R^2$, $R^3$ and W may have any of the meanings described herein, and wherein B is adenine, guanine, cytosine, thymine, uracil, or a substituted uracil as described below.

In a particular embodiment, the present invention also relates to the phosphate-modified nucleosides represented by the structural formula (I') wherein B, $R^1$, $R^2$ and W may have any of the meanings described herein, and wherein $R^3$ is hydrogen.

In a particular embodiment, the present invention also relates to the phosphate-modified nucleosides represented by the structural formula (I') wherein B, $R^1$, $R^2$ and $R^3$ may have any of the meanings described herein, and wherein W is O.

In a particular embodiment, the present invention also relates to the phosphate-modified nucleosides represented by the structural formula (I') wherein B, $R^2$, $R^3$ and W may have any of the meanings described herein, and wherein $R^1$ is hydrogen. In another particular embodiment, the present invention also relates to the phosphate-modified nucleoside of formula (I') wherein B, $R^2$, $R^3$ and W have any of the meanings described herein, and wherein $R^1$ is hydroxyl.

In a particular embodiment, the present invention relates to the phosphate-modified nucleosides represented by the structural formula (I') wherein B, $R^1$, $R^2$, $R^3$ and W may have any of the meanings described herein, and wherein n is 1.

In a particular embodiment, the present invention also relates to the phosphate-modified nucleosides represented by the structural formula (I') wherein $R^1$, $R^2$, $R^3$ and W may have any of the meanings described herein, and wherein B is any pyrimidine or purine base analogue as defined below, in particular 5-azapyrimidine, 5-azacytosine, 7-deazapurine, 7-deazaadenine, 7-deazaguanine or 7-deaza-8-azapurine.

In another particular embodiment of the invention, with reference to the structural formula (VI), Z may be O, NH or NCH₃.

In another particular embodiment of the invention, with reference to the structural formula (VI), aryl is a phenyl group optionally substituted with one or more substituents independently selected from the group consisting of halogen, amino, trifluoromethyl, hydroxyl, sulfhydryl, nitro, ($C_1$-$C_6$) alkoxy, trifluoromethoxy, cyano and $(CH_2)_q$—COOR, wherein R is hydrogen or ($C_1$-$C_6$) alkyl, and q is 0, 1 or 2. In a more particular embodiment of the foregoing, said phenyl is substituted with 1, 2, or 3 $(CH_2)_q$—COOR, wherein R is hydrogen or ($C_1$-$C_6$)alkyl, and q is 0, 1 or 2.

In another particular embodiment of the invention, $R^3$ is hydrogen and aryl is a phenyl substituted with 1, 2, or 3 $(CH_2)_q$—COOR, wherein R is hydrogen or ($C_1$-$C_6$) alkyl, and q is 0, 1 or 2.

In a yet more particular embodiment of the invention, $R^3$ is hydrogen and aryl is a phenyl substituted with two carboxylic acid groups, such as 1,2-dicarboxylphenyl or 1,3-dicarboxylphenyl.

In a yet more particular embodiment of the invention, $R^3$ is hydrogen and Ar is 1,2-dicarboxylphenyl or 1,3-dicarboxylphenyl.

In a particular embodiment of the foregoing, the present invention also relates to the phosphate-modified nucleoside represented by the structural formula (I') wherein the pyrimidine analogue B is represented by the structural formula (C):

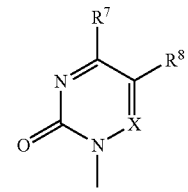

wherein
  $R^7$ is selected from the group consisting of —OH, —SH, —NH₂, —NHCH₃ and —NHC₂H₅;
  $R^8$ is selected from the group consisting of hydrogen, methyl, ethyl, isopropyl, amino, ethylamino, trifluoromethyl, cyano and halogen; and
  X is CH or N.

In yet another particular embodiment of the foregoing, the present invention also relates to phosphate-modified nucleosides of formula (I') wherein the purine analogue B is represented by the structural formula (D):

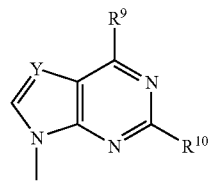

wherein
  $R^9$ is selected from the group consisting of hydrogen, —OH, —SH, —NH₂, and —NHCH₃;
  $R^{10}$ is selected from the group consisting of hydrogen, methyl, ethyl, hydroxyl, amino and halogen; and
  Y is CH or N.

In another particular embodiment, the novel phosphate-modified nucleoside of this invention is 5-O-1,3-dicarboxylphenyl-dAMP, 5-NH-1,3-dicarboxylphenyl-dAMP, 4-O-1,2-dicarboxylphenyl-dAMP, 5-O-1,3-dicarboxylphenyl-dCMP, 5-NH-1,3-dicarboxylphenyl-dCMP, 4-O-1,2-dicarboxylphenyl-dCMP, 5-O-1,3-dicarboxylphenyl-dGMP, 5-NH-1,3-dicarboxylphenyl-dGMP, 4-O-1,2-dicarboxylphenyl-dGMP, 5-O-1,3-dicarboxylphenyl-dTMP, 5-NH-1,3-dicarboxylphenyl-dTMP, 4-O-1,2-dicarboxyl-phenyl-dTMP, 5-O-1,3-dicarboxylphenyl-dUMP, 5-NH-1,3-dicarboxylphenyl-dUMP or 4-O-1,2-dicarboxylphenyl-dUMP.

In another particular embodiment, the novel phosphate-modified nucleoside of this invention is 5-O-1,3-dicarboxylphenyl-AMP, 5-NH-1,3-dicarboxylphenyl-AMP, 4-O-1,2-dicarboxylphenyl-AMP, 5-O-1,3-dicarboxylphenyl-CMP, 5-NH-1,3-dicarboxyl-phenyl-CMP, 4-O-1,2-dicarboxylphenyl-CMP, 5-O-1,3-dicarboxylphenyl-GMP, 5-NH-1,3-dicarboxylphenyl-GMP, 4-O-1,2-dicarboxylphenyl-GMP, 5-O-1,3-dicarboxyl-phenyl-TMP, 5-NH-1,3-dicarboxylphenyl-TMP, 4-O-1,2-dicarboxylphenyl-TMP, 5-O-1,3-dicarboxylphenyl-UMP, 5-NH-1,3-dicarboxylphenyl-UMP or 4-O-1,3-dicarboxyl-phenyl-UMP.

A second aspect of the first and second broad embodiments of the present invention relates to the use of the phosphate-modified nucleosides represented by the structural formulae (I), (I'), (A) and (A'), including any of the above-referred specific embodiments thereof, as a substrate for DNA- or RNA-polymerases, these polymerases being either wild-type (naturally occurring) or mutated according to common knowledge in the art. In a particular embodiment of the present invention, said DNA- or RNA-polymerases may be selected from Therminator DNA polymerase, KF (exo) DNA polymerase, or Reverse Transcriptase (e.g. HIV-RT) or mutated forms of these enzymes. If needed, the enzymes as described herein above can be mutated, using common knowledge in the art, in order to better adapt to the novel phosphate-modified nucleosides disclosed in this invention. Within this second aspect, the invention relates to a method for preparing an oligonucleotide comprising phosphate-modified nucleosides, comprising the step of incorporating at least one of said phosphate-modified nucleosides into a DNA/RNA strand, wherein said phosphate-modified nucleoside is represented by any one of the structural formulae (A), (I), (A') and (I'), including any one of the specific embodiments described herein.

Within the general framework of such a method, one or more of the following embodiments may be particularly useful:
the oligonucleotide may be prepared by DNA/RNA polymerase-dependent amplification;
said DNA/RNA polymerase-dependent amplification is PCR;
the oligonucleotide may be prepared by administering said phosphate-modified nucleosides to bacteriae comprising a DNA/RNA polymerase;
said polymerase may be from a microorganism or from bacterial or viral origin;
said polymerase may be Therminator DNA polymerase; KF (exo$^-$) DNA polymerase or Reverse Transcriptase.

In a particular embodiment, the phosphate-modified nucleosides of this invention being represented by the structural formulae (I), (I'), (A) and (A'), including any of the above-referred specific embodiments thereof, can be used to build in at least 1, 2 or 3 nucleotides in a growing DNA- or RNA-strand.

In another particular embodiment, the phosphate-modified nucleosides of this invention being represented by the structural formulae (I), (I'), (A) and (A'), including any of the above-referred specific embodiments thereof, can be used to build in at maximum 1, 2 or 3 nucleotides in a growing DNA- or RNA-strand.

In another particular embodiment, the phosphate-modified nucleosides of this invention being represented by the structural formulae (I), (I'), (A) and (A'), including any of the above-referred specific embodiments thereof, can be used to build in at most 300 nucleotides in a growing DNA- or RNA-strand.

In yet another particular embodiment, the phosphate-modified nucleosides of this invention being represented by the structural formulae (I), (I'), (A) and (A'), including any one of the above-referred specific embodiments thereof, can be used in combination with a mixture of natural dNTPs or NTPs (ATP,CTP,GTP,UTP,TTP) as a substrate for DNA/RNA-polymerases, more in particular to built in 1-300 (e.g. 2-300) nucleotides in a growing DNA- or RNA-strand.

The present invention also relates to the use of the phosphate-modified nucleosides represented by the structural formulae (I), (I'), (A) and (A'), including any one of the above-referred specific embodiments thereof, for the enzymatic production of oligonucleotides, peptides or proteins.

In a particular embodiment, the phosphate-modified nucleosides of the invention being represented by the structural formulae (I), (I'), (A) and (A'), including any one of the above-referred specific embodiments thereof, can be used for in vitro production of DNA or RNA. In another particular embodiment, the phosphate-modified nucleosides of the invention being represented by the structural formulae (I), (I'), (A) and (A'), including any one of the above-referred specific embodiments thereof, can also be used for in vitro production of peptides or proteins. In another particular embodiment the phosphate-modified nucleosides of the invention being represented by any one of the structural formulae (I), (I'), (A) and (A'), including any one of the above-referred specific embodiments thereof, can be used for PCR (polymerase chain reaction).

In yet another particular embodiment, the phosphate-modified nucleosides of the invention being represented by any one of the structural formulae (I), (I'), (A) and (A'), including any one of the above-referred specific embodiments thereof, can be used as a substrate for the growth of wild type and/or mutated bacteriae. In a particular embodiment, the phosphate-modified nucleosides of the invention being represented by any one of the structural formulae (I), (I'), (A) and (A'), including any one of the above-referred specific embodiments thereof, can be used as a substrate for the growth of bacteriae with mutated DNA/RNA polymerase, preferably wherein the mutation is suitable to better adapt better to the new substrate.

Another aspect of the invention relates to a pharmaceutical or non-pharmaceutical composition comprising the phosphate-modified nucleosides of the invention being represented by any one of the structural formulae (I), (I'), (A) and (A'), including any one of the above-referred specific embodiments thereof. In a particular embodiment, said non-pharmaceutical composition further comprises one or more natural NTPs or dNTPs (e.g. ATP,CTP,GTP,UTP,TTP).

Yet another aspect of the invention relates to a method for the production of oligonucleotides, RNA, DNA, peptides and/or proteins by using the phosphate-modified nucleotides of the invention being represented by any one of the structural formulae (I), (I'), (A) and (A'), including any one of the above-referred specific embodiments thereof.

Another aspect of the present invention relates to compounds (phosphate-modified nucleosides) represented by any one of the structural formulae (I), (I'), (A) and (A'), including any one of the above-referred specific embodiments thereof, having antiviral activity, more specifically to these compounds that inhibit the replication of viruses, even more specifically to these compounds that inhibit the replication of HIV-1.

Another aspect of the present invention relates to the compounds (phosphate-modified nucleosides) being represented by any one of the structural formulae (I), (I'), (A) and (A'), including any one of the above-referred specific embodiments thereof, for use as a medicine to treat or prevent a viral infection in a mammal, even more particularly to treat or prevent a HIV infection in a mammal such as a human being.

Another aspect of the invention relates to pharmaceutical compositions comprising the compounds (phosphate-modified nucleosides) being represented by any one of the structural formulae (I), (I'), (A) and (A'), including any one of the above-referred specific embodiments thereof, in combination with one or more pharmaceutical excipients. The invention further relates to the incorporation of a compound (phosphate-modified nucleoside) being represented by any one of the structural formula (I), (I'), (A) or (A'), including any one of the above-referred specific embodiments thereof, in the manufacture of a medicament useful for the treatment or prevention of viral infections, specifically for the treatment of a retroviral infection, and more specifically for the treatment of a HIV-1 infection. The present invention also relates to a method of treatment or prevention of a viral infection, such as a HIV-1 infection, in a mammal such as a human being by administering to said mammal a therapeutically effective amount, for instance an antiviral amount, specifically an antiretroviral amount, more specifically an anti-HIV-1 amount, of a compound (phosphate-modified nucleoside) being represented by any one of the structural formula (I), (I'), (A) or (A'), including any one of the above-referred specific embodiments thereof.

Still another aspect of the invention relates to a process for the preparation of the phosphate-modified nucleosides of the invention. In one embodiment of said aspect, the method comprises the steps of interacting a nucleotide monophosphate (NMP) with the methyl ester of an amino acid to produce the methyl ester of an amino acid phosphoramidate nucleotide analogue. Deprotection of this nucleoside analogue with an effective amount of a deprotecting agent such as, but not limited to, an alkali hydroxide, e.g. 0.04 M NaOH, provides the desired amino acid phosphoramidate nucleoside of this invention. In an alternative embodiment of said aspect, the process for the preparation of the phosphate-modified nucleosides of the invention comprises the synthetic step as shown in the following Scheme 1:

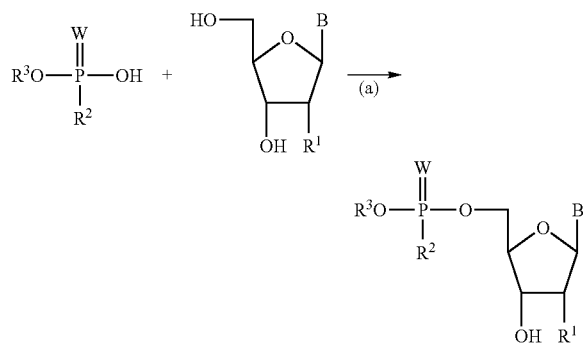

wherein (a) schematically represents the presence in the reaction mixture of an effective amount of a suitable catalyst for the condensation of the 5'-OH and phosphate acid groups. Suitable such catalysts are well known in the art and include, but are not limited to, arylsulfonylhalides, e.g. an optionally substituted phenylsulfonyl chloride.

10⁻⁴ U/μL; time points: 5, 15, 30, 60, 90 and 120 minutes. Blank: 125 nM primer/template (P1/T3), [Therminator]=8× 10⁻⁴ U/μL, no nucleotide substrate.

Figure 12:
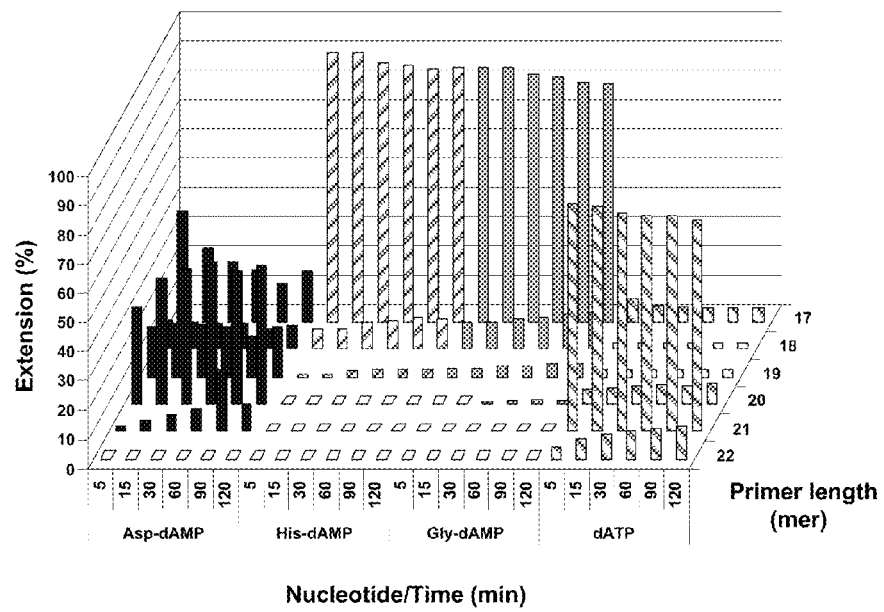

FIG. 12 shows primer extension efficiency of Therminator DNA polymerase. Reactions conditions: Primer (P1) was 5'-labeled with $^{33}$P followed by annealing to a template T3; 125 nM primer/template (P1/T3), [AA-dAMP]=500 μM; [dATP]=50 μM; [Therminator]=8×10⁴ U/μL; time points: 5, 15, 30, 60, 90 and 120 minutes. Blank: 125 nM primer/template (P1/T3), [Therminator]=8×10⁻⁴ U/μL, no nucleotide substrate.

Figure 13:
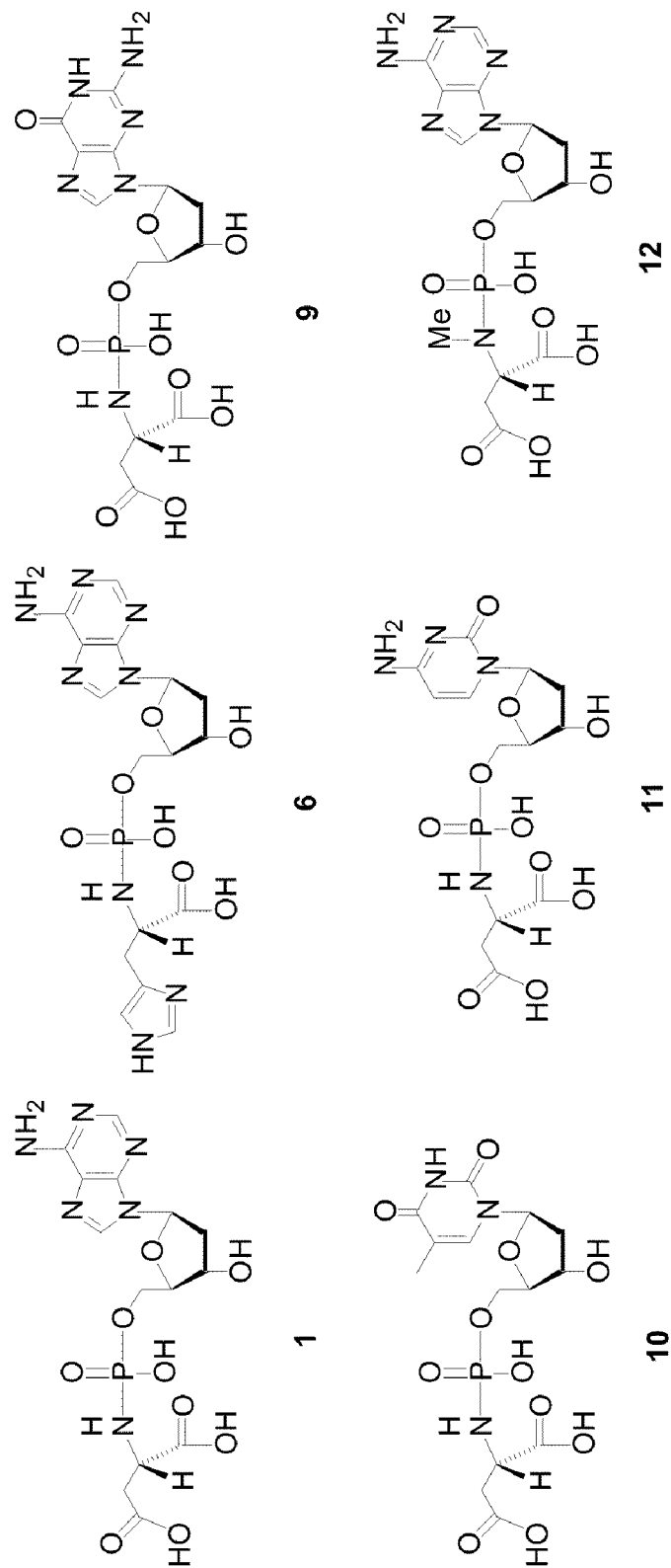

FIG. 13 shows structural representations of a few amino acid 2'-deoxy-nucleoside-5'-monophosphate derivatives used in the HIV RT incorporation assays of the present examples.

Figure 14:
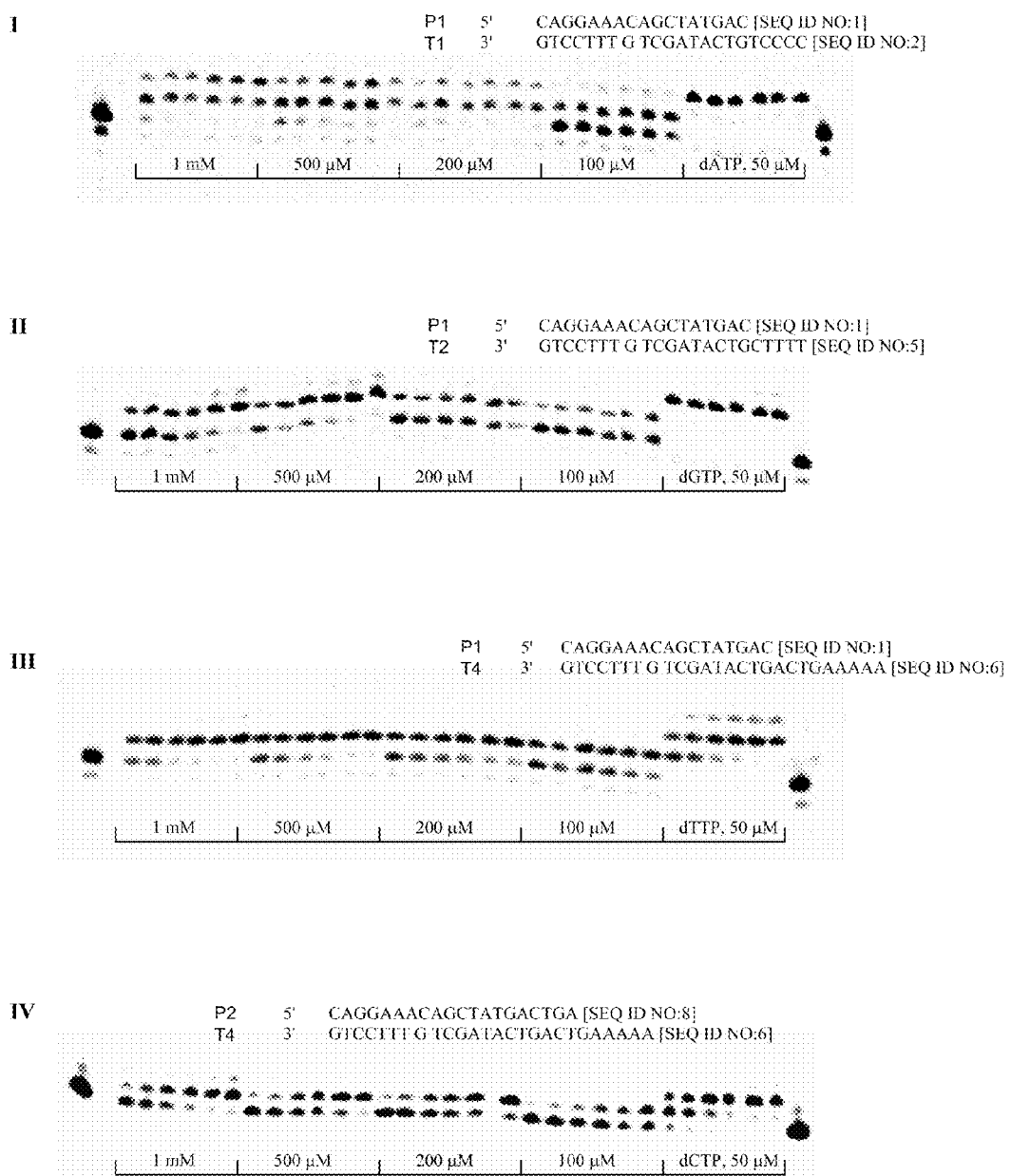

FIG. 14 shows primer extension with amino acid phosphoramidates by HIV RT. Conditions: Primer (P1 or P2) was 5'-labeled with $^{33}$P followed by annealing to a template (T1, T2 or T4). Reactions were carried out with 125 nM primer-template (P1/T1, P1/T2, P1/T4 or P2/T4), [HIV RT]=0.03 UμL⁻¹, time points: 5, 10, 20, 30, 60 and 120 minutes. Panel I shows the incorporation of derivative 12 with P1T1. Panel II shows the incorporation of derivative 9 with P1T2. Panel III shows the incorporation of derivative 10 with P1T4. Panel IV shows the incorporation of derivative 11 with P2T4.

Figure 15:
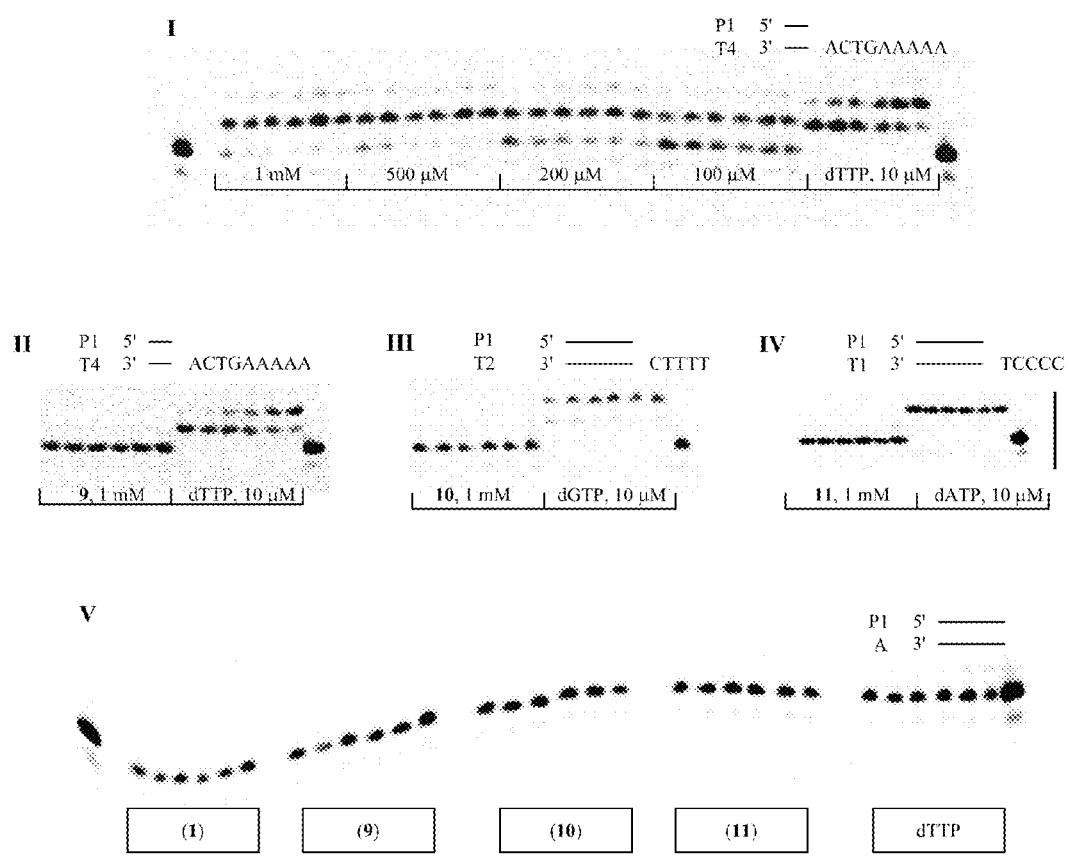

FIG. 15 shows control experiments. Conditions: Primer P1 was 5'-labeled with $^{33}$P followed by annealing to a template (T4, T2, T1 or A). Reactions were carried out with 125 nM primer-template (P1/T4, P1/T2 or P1/T1), [HIV RT]=0.03 UμL⁻¹, time points: 5, 10, 20, 30, 60 and 120 min. Panel I shows N-Me-Asp-dAMP (12) with P1T4 (A against A). Panel II shows L-Asp-dGMP (9) with P1T4 (G against A). Panel III shows L-Asp-dTMP (10) with P1T2 (T against C). Panel IV shows L-Asp-dCMP (11) with P1T1 (C against T). Panel V shows L-Asp-dAMP (1), L-Asp-dGMP (9), L-Asp-dTMP (10), L-Asp-dCMP (11) and dTTP with P1A. [Asp-dNMP]=1 mM UμL⁻¹.

Figure 16:
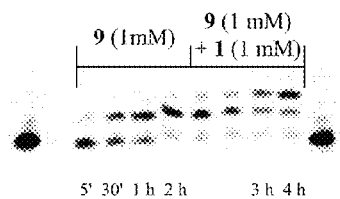
Figure 16:
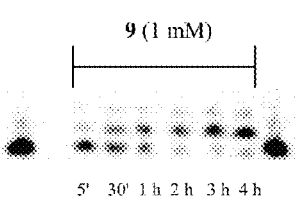

FIG. 16 shows (panel I) the incorporation of compounds 9 and 1 by HIV RT, and (panel II) a control experiment. Incorporation of compound 9 by HIV RT. Reaction conditions: Primer P1 was 5'-labeled with $^{33}$P followed by annealing to a template T2; 125 nM P1T2; [HIV RT]=0.03 UμL⁻¹.

Figure 17:
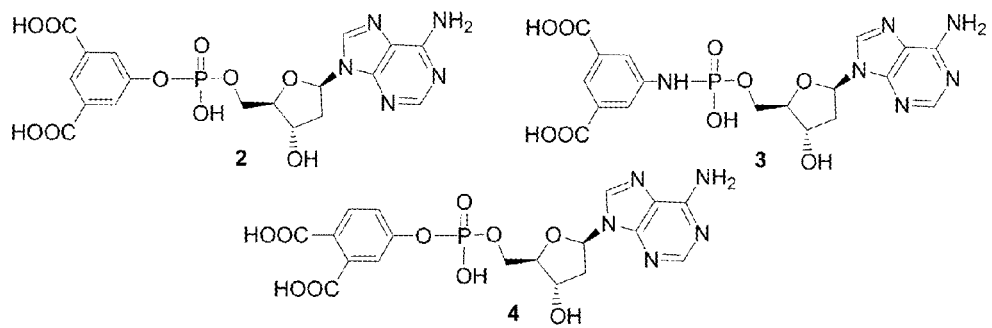

FIG. 17 shows a representation of the chemical structure of 5-O-isophthalic acid-dAMP 22, 5-NH-isophthalic acid-dAMP 23, and 4-O-phthalic acid-dAMP 24.

Figure 18:
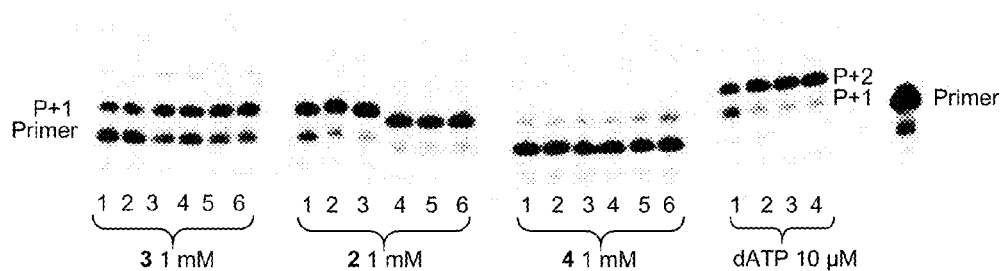

FIG. 18 shows the incorporation of derivatives 22 5-OH-iPA-dAMP, 23 5-NH-iPA-dAMP, and 24 4-OH-PA-dAMP into P1T1 by HIV Reverse Transcriptase. Aliquots were taken at 5, 10, 20, 30, 60 and 120 minutes, indicated as 1, 2, 3, 4, 5 and 6 respectively. For dATP, aliquots were taken at 5, 30, 60 and 120 minutes, indicated as 1, 2, 3 and 4 respectively.

Figure 19:
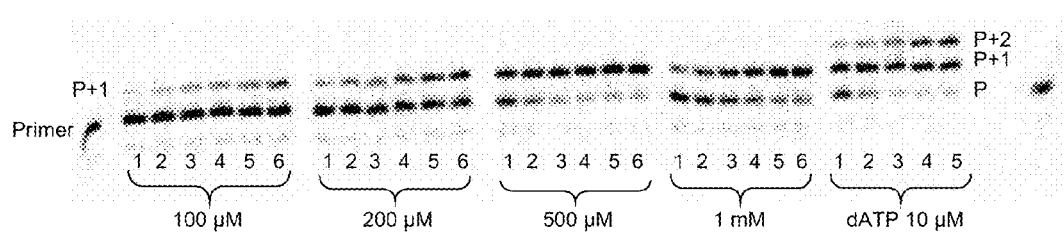

FIG. 19 shows the incorporation of 5-OH-iPA-dAMP (derivative 22) at different concentrations into P1T1 by HIV Reverse Transcriptase. Aliquots were taken at 5, 10, 20, 30, 60 and 120 minutes, indicated as 1, 2, 3, 4, 5 and 6 respectively. For dATP, aliquots were taken at 5, 10, 20, 30 and 60 minutes, indicated as 1, 2, 3, 4 and respectively.

Figure 20:
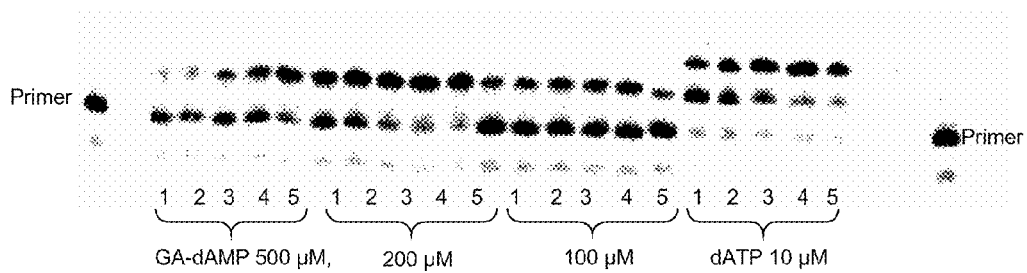

FIG. 20 shows the incorporation of GA-dAMP into P1T1 by HIV-1 Reverse Transcriptase, aliquots were taken at 5, 10, 20, 30 and 60 minutes, indicated as 1, 2, 3, 4 and 5 respectively.

DEFINITIONS

The term "nucleoside analogue" as used herein refers to known nucleoside modifications wherein the sugar ring is modified or removed and therefore also comprises acyclic nucleosides. Nucleoside analogue examples wherein the natural sugar moiety is modified include but are not limited to hexitol nucleic acid (HNA), cyclohexene nucleic acids (CeNA), locked nucleic acids (LNA), altritol nucleic acids (ANA) and peptide nucleic acids (PNA).

The term "pyrimidine and purine bases" as used herein includes, but is not limited to, adenine, thymine, cytosine, uracyl, guanine and 2,6-diaminopurine and analogues thereof. A purine or pyrimidine base as used herein includes a purine or pyrimidine base found in naturally occurring nucleosides as mentioned above. An analogue thereof is a base which mimics such naturally occurring bases in such a way that their structures (the kinds of atoms and their arrangement) are similar to the naturally occurring bases but may either possess additional or lack certain of the functional properties of the naturally occurring bases. Such analogues include those derived by replacement of a CH moiety by a nitrogen atom (e.g. 5-azapyrimidines such as 5-azacytosine) or vice versa (e.g., 7-deazapurines, such as 7-deazaadenine or 7-deazaguanine) or both (e.g., 7-deaza, 8-azapurines). By derivatives of such bases or analogues are meant those bases wherein ring substituents are either incorporated, removed, or modified by conventional substituents known in the art, e.g. halogen, hydroxyl, amino, ($C_1$-$C_6$)alkyl and others. Such purine or pyrimidine bases, and analogues thereof, are well known to those skilled in the art, e.g. as shown at pages 20-38 of WO 03/093290, the content of which is incorporated herein by reference.

In particular purine and pyrimidine analogues B for the purpose of the present invention may be selected from the group comprising pyrimidine bases represented by the structural formula (B):

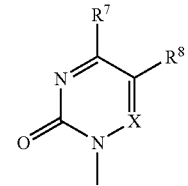

wherein
$R^7$ is selected from the group consisting of —OH, —SH, —NH$_2$, —NHCH$_3$ and —NHC$_2$H$_5$;
$R^8$ is selected from the group consisting of hydrogen, methyl, ethyl, isopropyl, amino, ethylamino, trifluoromethyl, cyano and halogen; and
X is CH or N,
and purine bases represented by the structural formula (D):

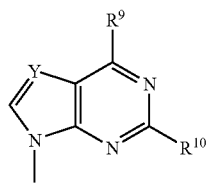

wherein:
$R^9$ is selected from the group consisting of hydrogen, —OH, —SH, —NH$_2$, and —NH-Me;
$R^{10}$ is selected from the group consisting of hydrogen, methyl, ethyl, hydroxyl, amino and halogen; and
X and Y are independently selected from CH and N.

Just as a few non-limiting examples of pyrimidine analogues, can be named substituted uracils with the formula (B) wherein X is CH, $R^7$ is hydroxyl, and $R^8$ is methyl, ethyl, isopropyl, amino, ethylamino, trifluoromethyl, cyano, fluoro, chloro, bromo or iodo.

The term "$(C_1$-$C_6)$ alkyl" as used herein refers to normal, secondary, or tertiary hydrocarbon chains having from 1 to 6 carbon atoms. Examples thereof are methyl, ethyl, 1-propyl, 2-propyl, 1-butyl, 2-methyl-1-propyl(1-Bu), 2-butyl (s-Bu) 2-methyl-2-propyl (t-Bu), 1-pentyl (n-pentyl), 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, n-pentyl, n-hexyl.

As used herein and unless otherwise stated, the term "cycloalkyl" refers to a monocyclic saturated hydrocarbon monovalent radical having from 3 to 6 carbon atoms, such as for instance cyclopropyl, cyclobutyl, cyclopentyl, cyclohexyl, or even up to 10 carbon atoms, such as for instance cycloheptyl, cyclooctyl and the like, or a $C_{7-10}$ polycyclic saturated hydrocarbon monovalent radical having from 7 to 10 carbon atoms such as, for instance, norbornyl, fenchyl, trimethyltricycloheptyl or adamantyl.

The term "$(C_1$-$C_6)$ alkoxy" as used herein refers to substituents wherein a carbon atom of a $(C_1$-$C_6)$ alkyl (such as defined herein), is attached to an oxygen atom through a single bond such as, but not limited to, methoxy, ethoxy, propoxy, isopropoxy, butoxy, iso-butoxy, sec-butoxy, pentoxy, 3-pentoxy, or hexyloxy.

As used herein, and unless otherwise stated, the term "aryl" designates any mono- or polycyclic aromatic monovalent hydrocarbon radical having from 6 up to 30 carbon atoms such as but not limited to phenyl, naphthyl, anthracenyl, phenantracyl, fluoranthenyl, chrysenyl, pyrenyl, biphenylyl, terphenyl, picenyl, indenyl, biphenyl, indacenyl, benzocyclobutenyl, benzocyclooctenyl and the like, including fused benzo-cycloalkyl radicals (the latter being as defined above) such as, for instance, indanyl, tetrahydronaphtyl, fluorenyl and the like, all of the said radicals being optionally substituted with one or more substituents independently selected from the group consisting of halogen, amino, trifluoromethyl, hydroxyl, sulfhydryl, nitro, $(C_1$-$C_6)$alkoxy, trifluoromethoxy, cyano and $(CH_2)_q$—COOR (wherein R is hydrogen or $(C_1$-$C_6)$ alkyl, and q is 0, 1 or 2), such as for instance 1,2-dicarboxylphenyl, 1,3-dicarboxylphenyl, 4-fluorophenyl, 4-chlorophenyl, 3,4-dichlorophenyl, 4-cyanophenyl, 2,6-dichlorophenyl, 2-fluorophenyl, 3-chlorophenyl, 3,5-dichlorophenyl and the like.

As used herein and unless otherwise stated, the term halogen refers to any atom selected from the group consisting of fluorine (F), chlorine (Cl), bromine (Br) and iodine (I).

Any substituent designation that is found in more than one site in a phosphate-modified nucleotide of this invention shall be independently selected.

The term "amino acid" as used herein refers to any "natural amino acid" (Alanine (ala), Arginine (Arg), Asparagine (asn), Aspartic acid (asp), Cysteine (cys), Glutamine (gln), Glutamic acid (glu), Glycine (gly), Histidine (his), Hydroxylysine (Hyl), Hydroxyproline (Hyp), Isoleucine (ile), Leucine (leu), Lysine (lys), Methionine (met), Phenylalanine (phe), Proline (pro), Serine (ser), Threonine (thr), Tryptophan (trp), Tyrosine (tyr), Valine (val)) in D or L conformation (but, within the context of this invention, preferably the L conformation), as well as to "unnatural (or synthetic) amino acids" (e.g., but not limited to, phosphoserine, phosphothreonine, phosphotyrosin, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, alpha-methyl-alanine, para-benzoylphenylalanine, phenylglycine, propargylglycine, sarcosine, and tert-butylglycine). This term also comprises natural and unnatural amino acids being protected at their carboxylic terminus (e.g. as a $(C_1$-$C_6)$ alkyl, phenyl or benzyl ester or as an amide, such as for example, a mono-$(C_1$-$C_6)$ alkyl or di-$(C_1$-$C_6)$ alkyl amide). Other suitable carboxy protecting groups are known to those skilled in the art (See for example, T. W. Greene, Protecting Groups In Organic Synthesis; Wiley: New York, 1981, and references cited therein).

It will be appreciated by those skilled in the art that phosphate-modified nucleotides of the invention having a chiral center may exist in and be isolated in optically active and racemic forms. Some phosphate-modified nucleotides may exhibit polymorphism. It is to be understood that the present invention encompasses any racemic, optically-active, polymorphic, or stereoisomeric form, or mixtures thereof, of a phosphate-modified nucleotide of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

The term "salt" as used herein, refers to the ionic product of a reaction between an acid and a base, and embraces the "pharmaceutically acceptable salts" as described in details below. Salts of the phosphate-modified nucleosides represented by any one of the structural formulae (I), (I'), (A) and (A'), including any one of the particular embodiments thereof, may be formed at any acid or base functionality within the compound, in particular, $R^3$, $R^4$ and $R^5$ may represent or comprise an acid or base functionality. In particular, salts of the phosphate-modified nucleosides represented by any one of the structural formulae (I), (I'), (A) and (A') may be formed as follows. When $R^3$ is hydrogen, it is acidic and may therefore engage in salt formation with an inorganic or organic base. $R^4$ and $R^5$ may comprise acidic functionalities such as carboxylic groups (COOH), which can equally engage in salt formation with an organic or inorganic base. Alternatively, $R^4$ and $R^5$ may comprise base functionalities, such as imidazolyl, which in turn can engage in salt formation with an organic or inorganic acid.

Certain of the phosphate-modified nucleosides described herein are capable of acting as prodrugs when substituted with appropriately selected functional groups. These are labile functional groups which separate from an active inhibitory phosphate-modified nucleoside during metabolism, systemically, inside a cell, by hydrolysis, enzymatic cleavage, or by some other process (see e.g. Bundgaard et al., Design and Application of Prodrugs in "Textbook of Drug Design and Development" (1991), Eds. Harwood Academic Publishers, pp. 113-191), the content of which is incorporated herein by reference. These prodrug moieties can serve to enhance solubility, absorption and lipophilicity to optimize drug delivery, bioavailability and efficacy. A "prodrug" may thus be a covalently modified analogue of a therapeutically active phosphate-modified nucleoside as defined herein, and can be therapeutically active in its own right.

The term "prodrug", as used herein, more specifically relates to an inactive or significantly less active derivative of a phosphate-modified nucleoside represented by any one of the structural formulae (I), (I'), (A) and (A'), including any one of the particular embodiments thereof, which undergoes spontaneous or enzymatic transformation within the body of a mammal (e.g. a human being) in order to release the pharmacologically active form of the compound. For a comprehensive review, see Rautio J. et al. in "Prodrug design and clinical applications, Nature Reviews Drug Discovery" (2008) doi: 10.1038/nrd2468), the content of which is incorporated herein by reference. In particular for the purpose of the present invention, prodrugs of the phosphate-modified nucleosides represented by any one of the structural formulae (I), (I'), (A) and (A'), including any one of the particular embodiments thereof, may be formed as follows. When $R_3$ is hydrogen, a free phosphate acid function is available for prodrug formation as described in detail by Hecker S. J. et al in "Prodrugs of phosphates and phosphonates, Journal of Medicinal Chemistry" (2008) doi: 10.1021/jm701260b). $R^4$ and $R^5$ comprise acid functionalities such as carboxylic acid groups (COOH) which may be used for the formation of a prodrug. Such carboxylic acid prodrug may occur in the form of an ester, in particular acyloxyalkylesters such as, but not limited to, a pivaloyloxymethyl ester (POM), an isopropyloxy-carbonyloxymethyl ester (POC) or a S-acyl-2-thioethyl (SATE) ester, a carbonate, a carbamate, or an amide, such as may be derived from amino acids.

The term "peptide" as used herein refers to a sequence of 2 to 50 amino acids (e.g. as defined hereinabove) or peptidyl residues. The sequence may be linear or cyclic. Preferably a peptide comprises 2 to 25, or 5 to 20 amino acids.

The term "oligonucleotide" as used herein refers to a polynucleotide formed by a plurality of linked nucleotide units. The nucleotide units each include a nucleoside unit linked together via a phosphate linking group. These nucleotides can be natural or modified in their phosphate, sugar or nucleobase group. The oligonucleotide may be naturally occurring or non naturally occurring.

The term "polymerase" as used herein refers to an enzyme that can synthesize DNA or RNA from a DNA or RNA template and includes but is not limited to Therminator DNA polymerase, KF(exo−)DNA polymerase and HIV Reverse Transcriptase.

Biological Applications of the Invention

Amino acid phosphoramidates, phospho-esters and phospho-thioesters according to this invention may be used as alternative substrates and biotechnology tools.

Fast emerging applications of modified nucleosides as biotechnology tools also require new and efficient ways to synthesize DNA and RNA building blocks such as nucleoside triphosphates and amidites for the use, for example, in PCR, labeling, or enzymatic incorporation of nucleotides, and in the automated DNA synthesis, respectively. Furthermore, some biotechnology applications require incorporation of a nucleotide by enzymatic means using DNA or RNA polymerases. However, at times, due to chemical nature and modifications present in the modified nucleosides, triphosphate synthesis is not always feasible and/or provides insufficient and low yields.

Thus, the invention relates to a method for preparing an oligonucleotide comprising phosphate-modified nucleosides, comprising the step of incorporating at least one of said phosphate-modified nucleosides into a DNA/RNA strand, wherein said phosphate-modified nucleoside is represented by any one of the structural formulae (A), (I), (A') and (I'), including any one of the specific embodiments described herein. Within the general framework of such a method, one or more of the following embodiments may be particularly useful:

the oligonucleotide may be prepared by DNA/RNA polymerase-dependent amplification;

said DNA/RNA polymerase-dependent amplification is PCR;

the oligonucleotide may be prepared by administering said phosphate-modified nucleosides to bacteriae comprising a DNA/RNA polymerase;

said polymerase may be from a microorganism or from bacterial or viral origin;

said polymerase may be Therminator DNA polymerase; KF (exo−) DNA polymerase or Reverse Transcriptase.

Therefore, an amino acid (such as, but not limited to, aspartic acid) coupled to a nucleoside monophosphate through a phosphoramidate (P—N) bond can serve as an alternative or substitute group to a pyrophosphate moiety. However, fitting into an active site and the subsequent nucleotidyl transfer may be less efficient for an amino acid phosphoramidate (e.g. Asp-dAMP) compared to the natural substrates/dNTPs (e.g. dATP) for the natural polymerase/enzyme. In this situation, mutated polymerases can be used to increase the efficiency of recognition and incorporation of amino acid phosphoramidate nucleotides. Such an embodiment of the invention with mutated polymerases can be used to specifically select or grow bacteriae by using these amino acid phosphoramidate nucleosides as a substrate. An additional advantage of this application is that polymerases that demonstrated efficient recognition and incorporation of amino acid phosphoramidate nucleosides in our studies are also shown to tolerate various sugar modifications and unnatural nucleobases quite well. Therefore, the enzymatic synthesis of DNA and, RNA sequences containing unnatural nucleobases can be accomplished whilst avoiding at times cumbersome nucleoside triphosphate synthesis and purification.

The amino acid phosphoramidates, phospho-esters and phospho-thioesters of this invention are also useful as antiviral compounds The compounds of the invention can be employed for the treatment of viral infections, more particularly Human Immunodeficiency Virus (HIV) infections, in particular of Human Immunodeficiency Virus type 1 (HIV-1). When using one or more derivatives represented by any one of the structural formulae (I), (I'), (A) and (A'), including any one of the particular embodiments thereof, as defined herein:

the active ingredients of the compound(s) may be administered to the mammal (including a human being) to be treated by any means well known in the art, i.e. orally, intranasally, subcutaneously, intramuscularly, intradermally, intravenously, intra-arterially, parenterally or by catheterization.

the therapeutically effective amount of the preparation of the compound(s), especially for the treatment of viral infections in humans and other mammals, preferably is a HIV enzyme inhibiting amount. More preferably, it is a HIV replication inhibiting amount or a HIV enzyme (in particular reverse transcriptase) inhibiting amount of the derivative(s) represented by any one of the structural formulae (I), (I'), (A) and (A'), including any one of the particular embodiments thereof, corresponds to an amount which ensures a plasma level of between 1 μg/ml and 100 mg/ml, optionally of 10 mg/ml. Depending upon the pathologic condition to be treated and the patient's condition, the said effective amount may be divided into several sub-units per day or may be administered at more than one day intervals.

The present invention further relates to a method for preventing or treating a viral infection in a subject or patient by administering to the patient in need thereof a therapeutically effective amount of the compounds of the present invention. The therapeutically effective amount of the compound(s), especially for the treatment of viral infections in humans and other mammals, preferably is a HIV enzyme inhibiting amount. More preferably, it is a HIV replication inhibiting amount or a HIV enzyme (in particular reverse transcriptase) inhibiting amount of the derivative(s) represented by any one of the structural formulae (I), (I'), (A) and (A'), including any one of the particular embodiments thereof. Depending upon the pathologic condition to be treated and the patient's condition, the said effective amount may be divided into several sub-units per day or may be administered at more than one-day intervals.

The present invention also relates to a combination of different antiviral drugs of the invention or to a combination of the antiviral drugs of the invention with one or more other drugs that exhibit anti-HIV activity.

The invention also relates to a combined preparation of antiviral drugs which may be either:
A) a composition comprising
  (a) a combination of two or more of the compounds of the present invention, and
  (b) optionally one or more pharmaceutical excipients or pharmaceutically acceptable carriers,
for simultaneous, separate or sequential use in the treatment or prevention of a viral infection, or
B) a composition comprising
  (c) one or more anti-viral agents, and
  (d) at least one compound of the present invention, and
  (e) optionally one or more pharmaceutical excipients or pharmaceutically acceptable carriers,
for simultaneous, separate or sequential use in the treatment or prevention of a viral infection.

Suitable anti-viral agents (c) for inclusion into the antiviral combined preparations of this invention include for instance, inhibitors of BVDV or HCV replication respectively, such as interferon-alfa (either pegylated or not), ribavirin and other selective inhibitors of the replication of HCV, such as a compound disclosed in EP1162196, WO 03/010141, WO 03/007945, WO 03/010140 and WO 00/204425 and/or an inhibitor of flaviviral protease and/or one or more additional flavivirus polymerase inhibitors.

The pharmaceutical composition or combined preparation with activity against viral infection according to this invention may contain a compound of the present invention over a broad content range depending on the contemplated use and the expected effect of the preparation. Generally, the content of the compound of the present invention in the combined preparation is within the range of 0.1 to 99.9% by weight, preferably from 1 to 99% by weight, more preferably from 5 to 95% by weight.

When using a pharmaceutical composition of combined preparation:
  the active ingredients may be administered to the mammal (including a human) to be treated by any means well known in the art, i.e. orally, intranasally, subcutaneously, intramuscularly, intradermally, intravenously, intra-arterially, parenterally or by catheterization; and/or
  the therapeutically effective amount of each of the active agents, especially for the treatment of viral infections in humans and other mammals, particularly is a HIV enzyme inhibiting amount.

When applying a combined preparation, the active ingredients may be administered simultaneously but it is also beneficial to administer them separately or sequentially, for instance within a relatively short period of time (e.g. within about 24 hours) in order to achieve their functional fusion in the body to be treated.

The invention also relates to the compounds of the formulae described herein being used for inhibition of the proliferation of other viruses than HIV-1, particularly for the inhibition of other members of the family of the retroviruses.

The present invention further provides veterinary compositions comprising at least one active ingredient as above defined together with a veterinary carrier therefor. Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

More generally, the invention relates to the compounds represented by any one of the structural formulae (I), (I'), (A) and (A'), including any one of the particular embodiments thereof, being useful as agents having biological activity (particularly antiviral activity) or as diagnostic agents.

The compounds of the invention optionally are bound covalently to an insoluble matrix and used for affinity chromatography separations, depending on the nature of the groups of the compounds, for example compounds with pendant aryl are useful in hydrophobic affinity separations.

Those of skill in the art will also recognize that the compounds of the invention may exist in many different protonation states, depending on, among other things, the pH of their environment. While the structural formulae provided herein depict the compounds in only one of several possible protonation states, it will be understood that these structures are illustrative only, and that the invention is not limited to any particular protonation state—any and all protonated forms of the compounds are intended to fall within the scope of the invention.

The term "pharmaceutically acceptable salts" as used herein means the therapeutically active non-toxic salt forms which the compounds (phosphate-modified nucleosides) represented by any one of the structural formulae (I), (I'), (A) and (A'), including any one of the particular embodiments thereof, are able to form. Therefore, the compounds of this invention optionally comprise salts of the compounds herein, especially pharmaceutically acceptable non-toxic salts containing, for example, $Na^+$, $Li^+$, $K^+$, $Ca^{2+}$ and $Mg^{2+}$. Such salts may include those derived by combination of appropriate cations such as alkali and alkaline earth metal ions or ammonium and quaternary amino ions with an acid anion moiety, typically a carboxylic acid. The compounds of the invention may bear multiple positive or negative charges. The net charge of the compounds of the invention may be either positive or negative. Any associated counter ions are typically dictated by the synthesis and/or isolation methods by which the compounds are obtained. Typical counter ions include, but are not limited to ammonium, sodium, potassium, lithium, halides, acetate, trifluoroacetate, etc., and mixtures thereof. It will be understood that the identity of any associated counter ion is not a critical feature of the invention, and that the invention encompasses the compounds in association with any type of counter ion. Moreover, as the compounds can exist in a variety of different forms, the invention is intended to encompass not only forms of the compounds that are in association with counter ions (e.g., dry salts), but also forms that are not in association with counter ions (e.g., aqueous or organic solutions). Metal salts typically are prepared by reacting the metal hydroxide with a compound of this invention. Examples of metal salts which are prepared in this way are salts containing $Li^+$, $Na^+$, and $K^+$. A less soluble metal salt can be precipitated from the solution of a more soluble salt by addition of the suitable metal compound. In addition, salts may be formed from acid addition of certain organic and inorganic acids to basic centers, typically amines, or to acidic groups. Examples of such appropriate acids include, for instance, inorganic acids such as hydrohalic acids, e.g. hydrochloric or hydrobromic acid, sulfuric acid, nitric acid, phosphoric acid and the like; or organic acids such as, for example, acetic, propanoic, hydroxyacetic, 2-hydroxypropanoic, 2-oxopropanoic, lactic, pyruvic, oxalic (i.e. ethanedioic), malonic, succinic (i.e. butanedioic acid), maleic, fumaric, malic, tartaric, citric, methanesulfonic, ethanesulfonic, benzene-sulfonic, p-toluenesulfonic, cyclohexanesulfamic, salicylic (i.e. 2-hydroxybenzoic), p-aminosalicylic and the like. Furthermore, this term also includes the solvates which the compounds represented by any one of the structural formulae (I), (I'), (A) and (A'), including any one of the particular embodiments thereof, as well as their salts are able to form, such as for example hydrates, alcoholates, nitriles and the like. Finally, it is to be understood that the compositions herein may comprise compounds of the invention in their unionized, as well as zwitterionic form, and combinations with stoichiometric amounts of water as in hydrates.

Also included within the scope of this invention are the salts of the parental compounds with one or more amino acids, especially the naturally-occurring amino acids found as protein components, as well as known non-natural analogues thereof. The amino acid typically is one bearing a side chain with a basic or acidic group, e.g., lysine, arginine or glutamic acid, or a neutral group such as glycine, serine, threonine, alanine, isoleucine, or leucine.

The compounds (phosphate-modified nucleosides) of the invention also include physiologically acceptable salts thereof. Examples of physiologically acceptable salts of the compounds (phosphate-modified nucleosides) of the invention include salts derived from an appropriate base, such as an alkali metal (for example, sodium), an alkaline earth (for example, magnesium), ammonium and $NA_4^+$ (wherein A is $C_1$-$C_4$ alkyl). Physiologically acceptable salts of an hydrogen atom or an amino group include salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids. Physiologically acceptable salts of a compound containing a hydroxy group include the anion of said compound in combination with a suitable cation such as $Na^+$ and $NA_4^+$ (wherein A typically is independently selected from H or a $C_1$-$C_4$ alkyl group). However, salts of acids or bases which are not physiologically acceptable may also find use, for example, in the preparation or purification of a physiologically acceptable compound. All salts, whether or not derived form a physiologically acceptable acid or base, are within the scope of the present invention.

As used herein and unless otherwise stated, the term "enantiomer" means each individual optically active form of a compound of the invention, having an optical purity or enantiomeric excess (as determined by methods standard in the art) of at least 80% (i.e. at least 90% of one enantiomer and at most 10% of the other enantiomer), preferably at least 90% and more preferably at least 98%.

The term "isomers" as used herein means all possible isomeric forms, including tautomeric and stereochemical forms, which the compounds of formula I may possess, but not including position isomers. Typically, the structures shown herein exemplify only one tautomeric or resonance form of the compounds, but the corresponding alternative configurations are contemplated as well. Unless otherwise stated, the chemical designation of compounds denotes the mixture of all possible stereochemically isomeric forms, said mixtures containing all diastereomers and enantiomers (since the compounds of formula I may have at least one chiral center) of the basic molecular structure, as well as the stereochemically pure or enriched compounds. More particularly, stereogenic centers may have either the R- or S-configuration, and multiple bonds may have either cis- or trans-configuration. Pure isomeric forms of the said compounds are defined as isomers substantially free of other enantiomeric or diastereomeric forms of the same basic molecular structure. In particular, the term "stereoisomerically pure" or "chirally pure" relates to compounds having a stereoisomeric excess of at least about 80% (i.e. at least 90% of one isomer and at most 10% of the other possible isomers), preferably at least 90%, more preferably at least 94% and most preferably at least 97%. The terms "enantiomerically pure" and "diastereomerically pure" should be understood in a similar way, having regard to the enantiomeric excess, respectively the diastereomeric excess, of the mixture in question. Separation of stereoisomers is accomplished by standard methods known to those in the art. One enantiomer of a compound of the invention can be separated substantially free of its opposing enantiomer by a method such as formation of diastereomers using optically active resolving agents (see e.g. "Stereochemistry of Carbon Compounds" (1962) by E. L. Eliel, McGraw Hill; and Lochmuller in *J. Chromatogr.* (1975) 113:(3) 283-302). Separation of isomers in a mixture can be accomplished by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure enantiomers, or (3) enantiomers can be separated directly under chiral conditions. Under method (1), diastereomeric salts can be formed by reaction of enantiomerically pure chiral bases such as brucine, quinine, ephedrine, strychnine, a-methyl-b-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts. Alternatively, by method (2), the substrate to be resolved may be reacted with one enantiomer of a chiral compound to form a diastereomeric pair (Eliel et al in *Stereochemistry of Organic Compounds* (1994) John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the free, enantiomerically enriched xanthene. A method of determining optical purity involves making chiral esters, such as a menthyl ester or Mosher ester, a-methoxy-a-(trifluoromethyl)phenyl acetate (Jacob III. (1982) J. Org. Chem. 47:4165), of the racemic mixture, and analyzing the NMR spectrum for the presence of the two atropisomeric diastereomers. Stable diastereomers can be separated and isolated by normal- and reverse-phase chromatography following methods for separation of atropisomeric naphthyl-isoquinolines (Hoye, T., WO96/15111). Under method (3), a racemic mixture of two asymmetric enantiomers is separated by chromatography using a chiral stationary phase. Suitable chiral stationary phases are, for example, polysaccharides, in particular cellulose or amylose derivatives. Commercially available polysaccharide based chiral stationary phases are ChiralCel™ CA, OA, OB5, OC5, OD, OF, OG, OJ and OK, and Chiralpak™ AD, AS, OP(+) and OT(+). Appropriate eluents or mobile phases for use in combination with said polysaccharide chiral stationary phases are hexane and the like, modified with an alcohol such as ethanol, isopropanol and the like.

The terms cis and trans are used herein in accordance with Chemical Abstracts nomenclature and include reference to the position of the substituents on a ring moiety. The absolute stereochemical configuration of the compounds of formula I may easily be determined by those skilled in the art while using well-known methods such as, for example, X-ray diffraction.

The compounds of the invention may be formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. Formulations optionally contain excipients such as those set forth in the "Handbook of Pharmaceutical Excipients" (1986) and include ascorbic acid and other antioxidants, chelating agents such as EDTA, carbohydrates such as dextrin, hydroxyalkylcellulose, hydroxyalkylmethylcellulose, stearic acid and the like.

Subsequently, the term "pharmaceutically acceptable carrier" as used herein means any material or substance with which the active ingredient is formulated in order to facilitate its application or dissemination to the locus to be treated, for instance by dissolving, dispersing or diffusing the said composition, and/or to facilitate its storage, transport or handling without impairing its effectiveness. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, suspensions, ointments, creams, tablets, pellets or powders.

Suitable pharmaceutical carriers for use in the said pharmaceutical compositions and their formulation are well known to those skilled in the art, and there is no particular restriction to their selection within the present invention. They may also include additives such as wetting agents, dispersing agents, stickers, adhesives, emulsifying agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals. The pharmaceutical compositions of the present invention may be prepared in any known manner, for instance by homogeneously mixing, coating and/or grinding the active ingredients, in a one-step or multi-steps procedure, with the selected carrier material and, where appropriate, the other additives such as surface-active agents. They may also be prepared by micronisation, for instance in view to obtain them in the form of microspheres usually having a diameter of about 1 to 10 μm, namely for the manufacture of microcapsules for controlled or sustained release of the active ingredients.

Suitable surface-active agents, also known as emulgent or emulsifier, to be used in the pharmaceutical compositions of the present invention are non-ionic, cationic and/or anionic materials having good emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher fatty acids ($C_{10}$-$C_{22}$), e.g. the sodium or potassium salts of oleic or stearic acid, or of natural fatty acid mixtures obtainable form coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates are the sodium, calcium or alcanolamine salts of dodecylbenzene sulphonic acid or dibutyl-naphtalenesulphonic acid or a naphtalenesulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanyiphosphatidyl-choline, dipalmitoylphosphatidyl-choline and their mixtures.

Suitable non-ionic surfactants include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with polypropylene glycol, ethylenediamino-polypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxypolyethoxyethanol, polyethyleneglycol and octylphenoxypoly-ethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants include quaternary ammonium salts, particularly halides, having 4 hydrocarbon radicals optionally substituted with halo, phenyl, substituted phenyl or hydroxy; for instance quaternary ammonium salts containing as N-substituent at least one $C_8$-$C_{22}$ alkyl radical (e.g. cetyl, lauryl, palmityl, myristyl, oleyl and the like) and, as further substituents, unsubstituted or halogenated lower alkyl, benzyl and/or hydroxy-lower alkyl radicals.

A more detailed description of surface-active agents suitable for this purpose may be found for instance in "McCutcheon's Detergents and Emulsifiers Annual" (MC Publishing Crop., Ridgewood, N.J., 1981), "Tensid-Taschenbucw", 2 d ed. (Hanser Verlag, Vienna, 1981) and "Encyclopaedia of Surfactants" (Chemical Publishing Co., New York, 1981), the contents of which is incorporated herein by reference.

Compounds of the invention and their physiologically acceptable salts (hereafter collectively referred to as the active ingredients) may be administered by any route appropriate to the condition to be treated, suitable routes including oral, rectal, nasal, topical (including ocular, buccal and sublingual), vaginal and parenteral (including subcutaneous, intramuscular, intravenous, intradermal, intrathecal and epidural). The preferred route of administration may vary with for example the condition of the recipient.

While it is possible for the active ingredients to be administered alone it is preferable to present them as pharmaceutical formulations. The formulations, both for veterinary and for human use, of the present invention comprise at least one active ingredient, as above described, together with one or more pharmaceutically acceptable carriers therefore and optionally other therapeutic ingredients. The carrier(s) optimally are "acceptable" in the sense of being compatible with the other ingredients of the formulation and not deleterious to the recipient thereof. The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein. For infections of the eye or other external tissues e.g. mouth and skin, the formulations are optionally applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base. If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG400) and mixtures thereof. The topical formulations may desirably include a compound which enhances absorption or penetration of the active ingredient through the skin or other affected areas. Examples of such dermal penetration enhancers include dimethylsulfoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Optionally, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

The choice of suitable oils or fats for the formulation is based on achieving the desired cosmetic properties, since the solubility of the active compound in most oils likely to be used in pharmaceutical emulsion formulations is very low. Thus the cream should optionally be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is optionally present in such formulations in a concentration of 0.5 to 20%, advantageously 0.5 to 10% particularly about 1.5% w/w. Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate. Formulations suitable for nasal administration wherein the carrier is a solid include a coarse powder having a particle size for example in the range 20 to 500 microns (including particle sizes in a range between 20 and 500 microns in increments of 5 microns such as 30 microns, 35 microns, etc), which is administered in the manner in which snuff is taken, i.e. by rapid inhalation through the nasal passage from a container of the powder held close up to the nose. Suitable formulations wherein the carrier is a liquid, for administration as for example a nasal spray or as nasal drops, include aqueous or oily solutions of the active ingredient. Formulations suitable for aerosol administration may be prepared according to conventional methods and may be delivered with other therapeutic agents.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavoring agents.

This invention includes controlled release pharmaceutical formulations containing as active ingredient one or more compounds of the invention ("controlled release formulations") in which the release of the active ingredient can be controlled and regulated to allow less frequency dosing or to improve the pharmacokinetic or toxicity profile of a given invention compound. Controlled release formulations adapted for oral administration in which discrete units comprising one or more compounds of the invention can be prepared according to conventional methods.

Additional ingredients may be included in order to control the duration of action of the active ingredient in the composition. Control release compositions may thus be achieved by selecting appropriate polymer carriers such as for example polyesters, polyamino acids, polyvinyl pyrrolidone, ethylene-vinyl acetate copolymers, methylcellulose, carboxymethylcellulose, protamine sulfate and the like. The rate of drug release and duration of action may also be controlled by incorporating the active ingredient into particles, e.g. microcapsules, of a polymeric substance such as hydrogels, polylactic acid, hydroxymethylcellulose, polymethyl methacrylate and the other above-described polymers. Such methods include colloid drug delivery systems like liposomes, microspheres, microemulsions, nanoparticles, nanocapsules and so on. Depending on the route of administration, the pharmaceutical composition may require protective coatings. Pharmaceutical forms suitable for injectionable use include sterile aqueous solutions or dispersions and sterile powders for the extemporaneous preparation thereof. Typical carriers for this purpose therefore include biocompatible aqueous buffers, ethanol, glycerol, propylene glycol, polyethylene glycol and the like and mixtures thereof.

In view of the fact that, when several active ingredients are used in combination, they do not necessarily bring out their joint therapeutic effect directly at the same time in the mammal to be treated, the corresponding composition may also be in the form of a medical kit or package containing the two ingredients in separate but adjacent repositories or compartments. In the latter context, each active ingredient may therefore be formulated in a way suitable for an administration route different from that of the other ingredient, e.g. one of them may be in the form of an oral or parenteral formulation whereas the other is in the form of an ampoule for intravenous injection or an aerosol.

Figure 2:
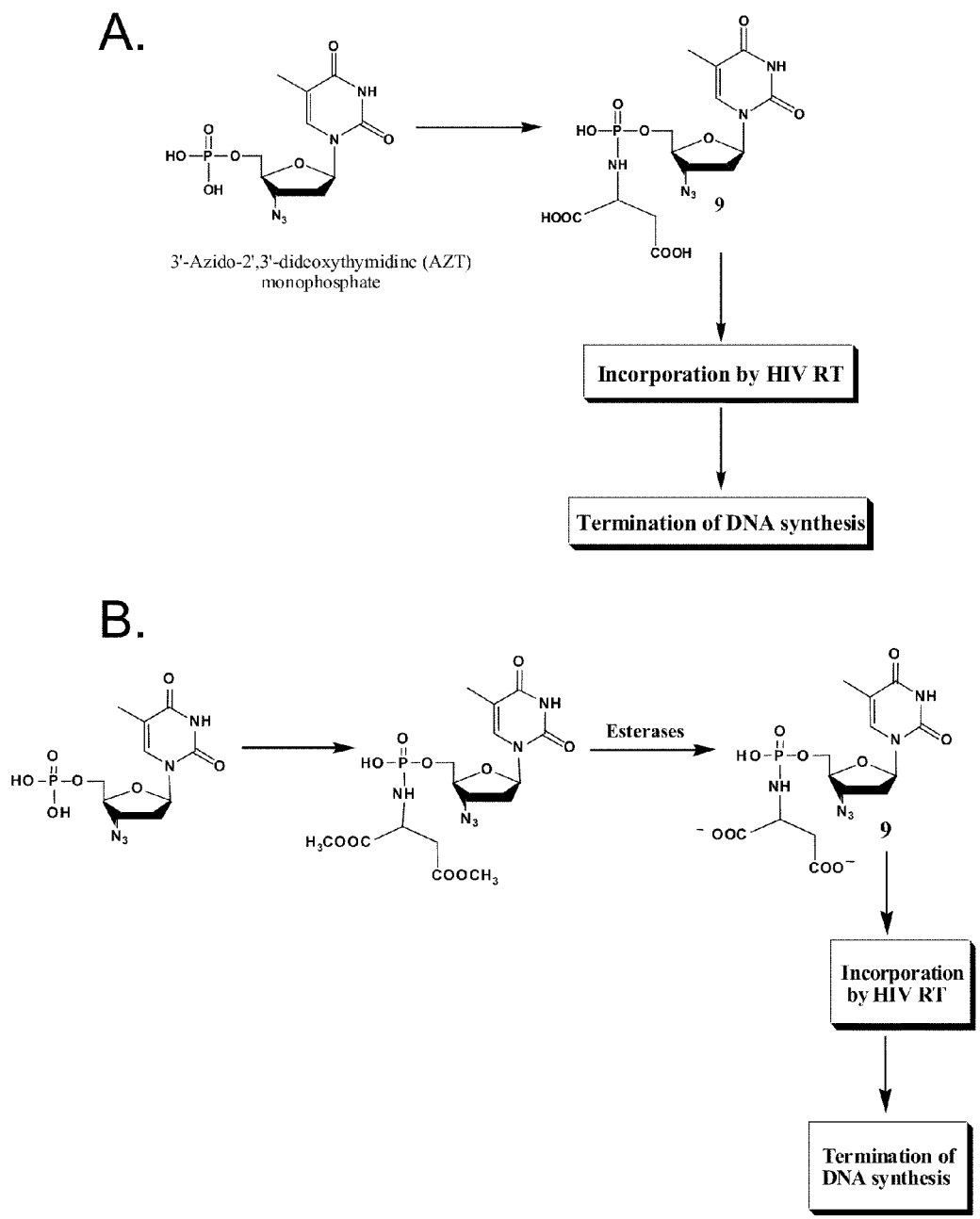
FIG. 2A schematically shows a possible activation of AZT monophosphate by aspartyl.
FIG. 2B schematically shows a possible application of aspartyl phosphoramidate moiety for in vivo delivery and activation of AZT monophosphate.

The presented invention shows that a phosphate-modified nucleoside represented by any one of the structural formulae (I), (I'), (A) and (A'), including any one of the particular embodiments thereof, such as but not limited to 2'-deoxyadenine-5'-aspartyl-phosphoramidate is successfully recognized and efficiently incorporated into a growing DNA strand by HIV RT and Therminator DNA polymerase. This means that an aspartyl-phosphoramidate moiety can mimic a pyrophosphate group and behave as a good leaving group in a nucleotidyl transfer. Incorporation of phosphoramidate analogues, although to a lesser extent, was also observed for histidyl and glycinyl phosphoramidates, respectively. Therefore, it is feasible to use chain-terminating nucleotides coupled to aspartic acid through a phosphoramidate linkage for a direct inhibition of HIV RT or other viral polymerases as depicted in FIG. 2A. Effective inhibition of HIV RT or other viral polymerases by a modified nucleoside requires its activation by cellular nucleoside kinases and conversion into a corresponding nucleoside triphosphate. Administration of AZT phosphoramidate 9 as a substitute for AZT nucleoside triphosphate can therefore eliminate a requirement for kinase activation. However, it is important to assess the ability of HIV RT to recognize and insert AZT phosphoramidate 9 with satisfactory efficiency. A potential drawback of this approach could be the charged nature of aspartyl phosphoramidate nucleotides. As a charged molecule, the aspartyl phosphoramidate of AZT is not likely to pass through a cellular membrane unless active transport is involved. However, intracellular diffusion is likely facilitated by masking the negative charges of carboxylate moieties by means of esterification as shown in FIG. 2B. Once a protected amino acid phosphoramidate analogue is in the cytosol, it can be transformed back to a charged, acidic form through the action of cellular esterases. These principles of monophosphate activation and subsequent inhibition of viral polymerases, as shown in FIGS. 2A and 2B for AZT, equally apply to other chain-terminating nucleotides known in the art.

Manufacture of the Compounds of the Invention

The synthesis of amino acid phosphoramidate nucleotide analogues of this invention may be accomplished according to the method illustrated by scheme 2, starting from a nucleoside monophosphate, which itself can be tailor-made by phosphorylation of a suitable nucleoside.

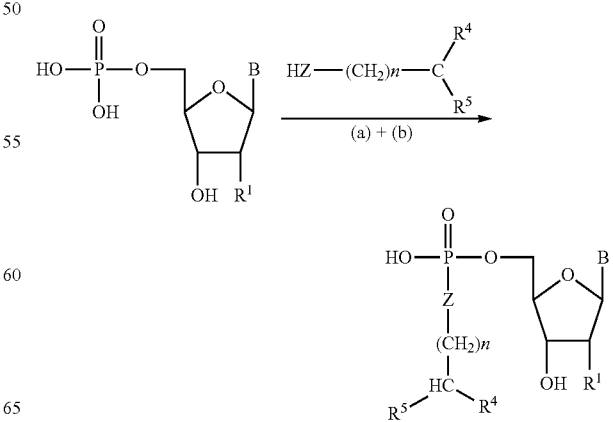

Scheme 2

The compounds according to the invention may be synthesized by derivatisation of the 5'-mono-phosphate nucleoside precursor molecule as illustrated in Scheme 2. In a first step (a), the phosphate group of the 5'-mono-phosphate nucleoside is coupled with the Z-group of the reagent represented by the structural formula (E)

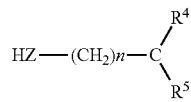
(E)

wherein Z, $R^4$ and $R^5$ are the same as defined in the structural formula (IV). Said coupling reaction results in the formation of a phosphate ester (when Z=O), phosphate amide (when Z=NH or N—R) or phosphate thioester (when Z=S). Said coupling reaction may be performed using any coupling agent (also referred to as dehydrating agent) known in the art for esterification or amide formation, in particular using a carbodiimide coupling agent, more particularly dicyclohexylcarbodiimide (DCC). The coupling reaction is preferably performed at a temperature between room temperature and reflux temperature of the solvent. Depending upon the nature of $R_4$ and $R_5$, additional acid, hydroxy or amine functionalities in reagent (E) may be transiently protected to prevent these functionalities from interfering with the condensation reaction between the phosphate acid and Z. Therefore, the synthetic route may provide for an optional subsequent step of deprotecting such functionalities.

Schemes 3 and 4 below illustrate synthetic routes for the synthesis of pyrimidine and purine derived compounds according to the present invention respectively.

Scheme 3

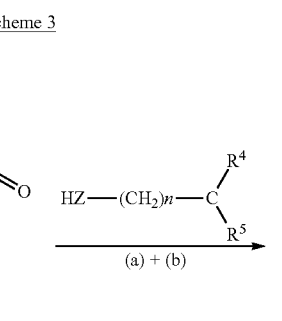

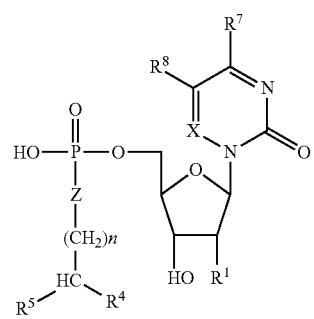

Scheme 4

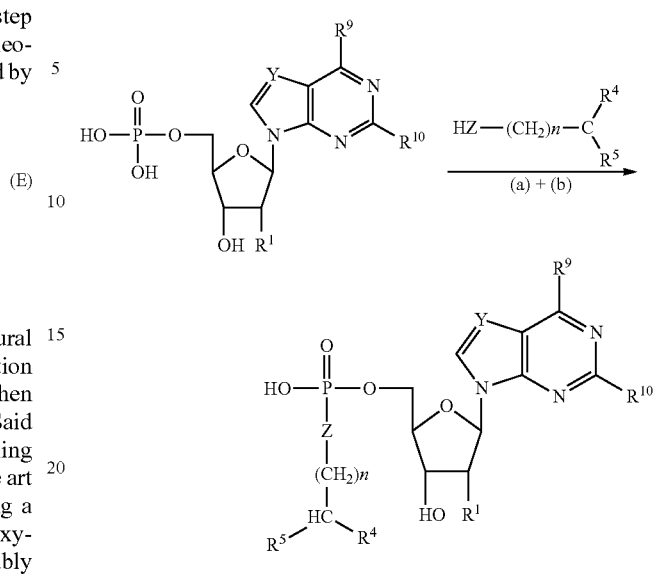

Alternatively, the compounds according to the structural formula (I), or any specific embodiments thereof, may be obtained using a synthetic procedure as illustrated by scheme 1 herein above.

The following examples are provided for illustrative purpose only, and should not be considered as limiting the scope of the present invention.

Example 1

Synthesis

Figure 1:
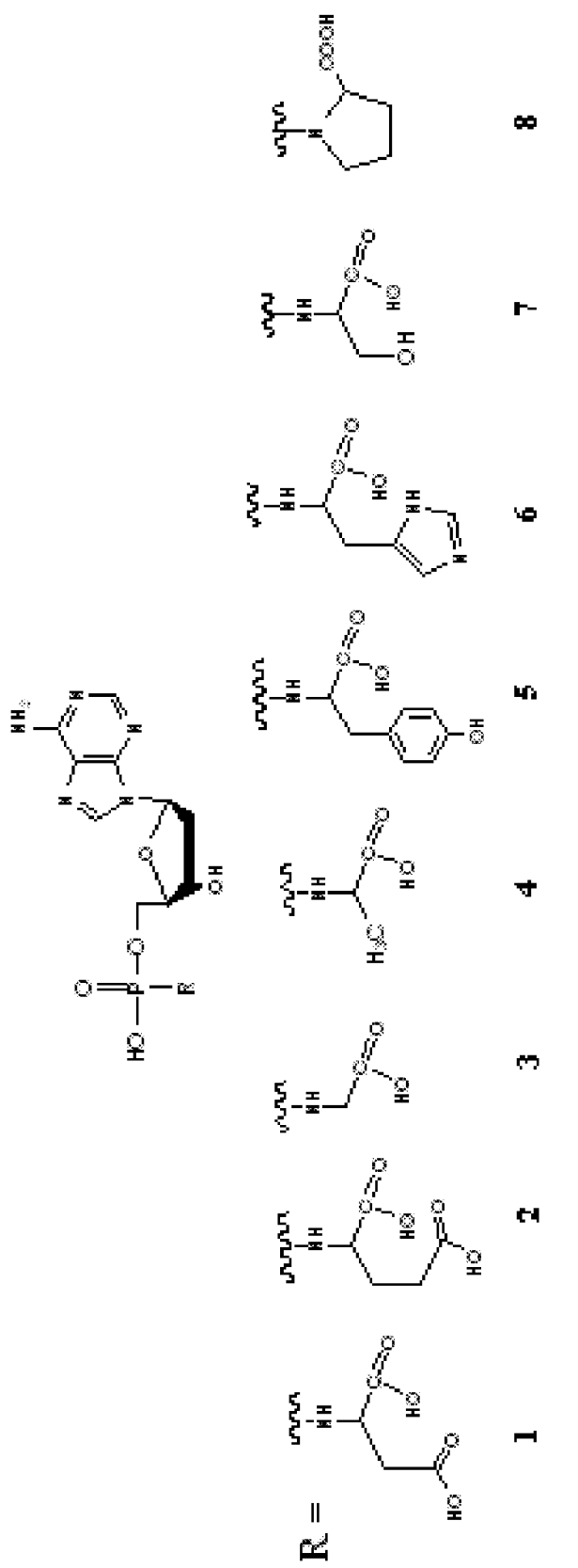
FIG. 1 shows structural representations of a few amino acid phosphoramidates prepared in the following examples as follows: 1 Asp-dAMP, 2 Glu-dAMP, 3 Gly-dAMP, 4 Ala-dAMP, 5 Tyr-dAMP, 6 His-dAMP, 7 Ser-dAMP, and 8 Pro-dAMP.

Scheme 5 below depicts 16 specific phosphate-modified nucleosides, but is applicable to other phosphate-modified nucleosides disclosed in this invention by introducing other substituents for $R^1$ and $R^2$ (i.e. using other alkyl residues instead of methyl). L-amino acids were used for synthesis of all phosphoramidate analogues of the examples wherein said amino acid is coupled to the phosphor atom with its α-amino function. However, this procedure is applicable to all D- and L-amino acids (both natural and unnatural) and organic phosphate-modified nucleotides that contain an amino group. The deprotection of the amino acid moiety was carried out with 0.4 M sodium hydroxide in methanol-water solution. For the isolation of the pure analogue phosphate-modified nucleotides, silica gel column chromatography was employed with iPrOH—$NH_3$—$H_2O$ mixture as an elution system. A series of phosphoramidate analogues coupled to a variety of natural L-amino acids synthesized as examples in this study is shown in Scheme 5 and FIG. 1. Step (a) of the synthesis illustrated by scheme 5 was performed with the use of DCC as a coupling agent in a mixture of water and tert-butanol under reflux temperature. Step (b) illustrates an optional saponification using 0.4M NaOH in a mixture of water and methanol.

Scheme 5

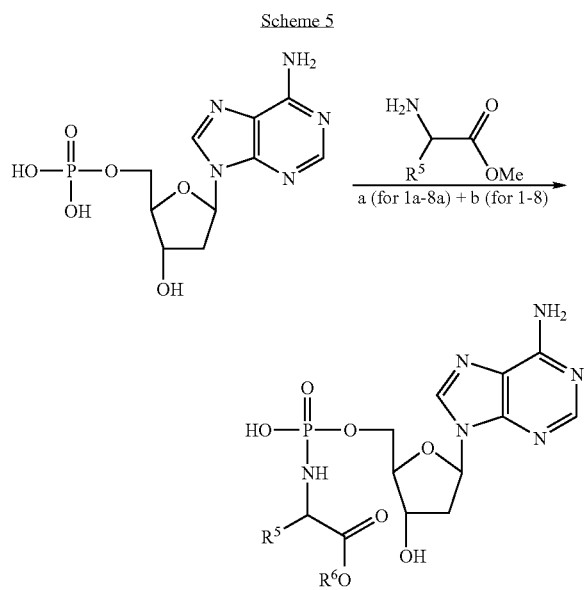

TABLE 1

| | $R^6$ | $R^5$ | | $R^6$ | $R^5$ |
|---|---|---|---|---|---|
| 1 | H | —$CH_2$—COOH | 1a | $CH_3$ | —$CH_2$—COOH |
| 2 | H | —$CH_2$—$CH_2$—COOH | 2a | $CH_3$ | —$CH_2$—$CH_2$—COOH |
| 3 | H | —H | 3a | $CH_3$ | —H |
| 4 | H | —$CH_3$ | 4a | $CH_3$ | —$CH_3$ |
| 5 | H | —$CH_2$-Ph-OH | 5a | $CH_3$ | —$CH_2$-Ph-OH |
| 6 | H | —$CH_2$-(imidazole) | 6a | $CH_3$ | —$CH_2$-(imidazole) |
| 7 | H | —$CH_2$—OH | 7a | $CH_3$ | —$CH_2$—OH |
| 8 | H | (pyrrolidine-COOH) | 8a | $CH_3$ | (pyrrolidine-COOMe) |

A typical experimental procedure for the synthesis of 5'-amino acid phosphoramidates of 2'-deoxyadenine, which is also generally applicable to other phosphoramidates of the invention, is presented below.

Nuclear magnetic resonance (NMR) spectral analyses were carried out on Brucker Avance™ II 300 MHz or 500 MHz with PAXTI probe. The Brucker Topspin™ 2.1 software was used to process spectra. Chemical shifts are expressed in parts per million (ppm) by frequency. $^1H$ and $^{13}C$ NMR chemical shifts are referenced to an internal TMS signal ($\delta$=0.00 ppm), $^{31}P$ NMR chemical shifts are referenced to an external 85% $H_3PO_4$ standard ($\delta$=0.00 ppm).

Standard mass spectra (MS) were measured with a Finnigan LCQ DuO (Thermo Fischer Scientific) using the ionization by electron impact technique, data were acquired with the LAC/E$^{32}$ system (Waters).

Exact mass spectra (MS) were obtained with a Q-T of 2™ (Micromass Ltd.) coupled to a CapLC™ system (Waters).

Chemicals of analytical or synthetic grade were obtained from commercial sources (dAMP: Sigma Aldrich; DCC: Fluke; thionyl chloride, phthalic acids and triethylamine: Acros) and were used as received.

Dimethyl esters of dicarboxylic acids were either obtained from commercial sources or prepared according to standard procedures.

Flash silica chromatography was performed on Davisil® silica gel 60, 0.040-0.063 mm (Grace Davison).

Thin Layer Chromatography was performed on Alugram® silica gel 60 mesh, 0.20 mm (Macherey-Nagel).

Synthesis of 2'-deoxy-adenosine-5'-dimethylaspartyl-phosphoramidate (1a)

In a two neck flask, 2'-deoxyadenosine-5'-monophosphoric acid hydrate (200 mg, 0.572 mmole) and L-aspartic acid dimethyl ester hydrochloride (791 mg, 4 mmoles) were dissolved in a mixture of tert-butanol (9 ml) and $H_2O$ (2 ml). A few drops of triethylamine ($Et_3N$) were added to the solution to facilitate dissolution. An appropriate amount of N,N'-dicyclohexylcarbodiimide (DCC) (826 mg, 4 mmoles, 7 equiv.) was dissolved under argon in 1 ml of tert-butanol and was dropwise added to the reaction mixture. The reaction mixture was refluxed carefully for 3-4 hours while stirring under argon. The progress of the reaction was monitored by TLC (PrOH:$NH_3$:$H_2O$). Upon completion, the reaction mixture was cooled down and the solvent was removed by rotary evaporation. The product was isolated by silica column chromatography eluting with $CHCl_3$:MeOH:$H_2O$ gradient affording the product as a white solid (238 mg, 87.8% yield) that was characterised as follows:

$^1H$ NMR (300 MHz, DMSO-$d_6$): $\delta$ 8.42 (s, 1H), 8.14 (s, 1H), 7.30 (s, 2H $NH_2$), 6.36 (t, J=7.0, 1H, H1'), 4.44 (s, 1H, H3'), 4.06-3.87 (m, 2H, H4', CHCOO$CH_3$), 3.81-3.69 (m, 2H, H5'), 3.57 (s, 3H, CHCOO$CH_3$), 3.55 (s, 3H, $CH_2$COO$CH_3$), 2.79-2.58 (m, 3H, H2', $CH_2$), and 2.35-2.19 (m, 1H, H2') ppm;

$^{13}C$ (500 MHz, DMSO-$d_6$): $\delta$ 174.04 (d, J(C,P)=25), 171.59 (d, J(C,P)=15.0), 156.46, 153.09, 149.71, 139.80, 119.31, 86.81 (d, J(C,P)=30.0), 83.51, 71.83, 64.61, 52.26, 51.84, 50.71, 39.08, and 35.88 ppm;

$^{31}P$ NMR (300 MHz, $H_2O$): $\delta$ 5.73; and

MS (ESI): [M–H]=473.4 High resolution MS (ESI): m/z calculated for $C_{16}H_{23}N_6O_9P$ 475.13, actual 475.13.

Synthesis of 2'-deoxy-adenosine-5'-aspartyl-phosphoramidate (1)

A solution (4-5 ml) of 0.4 M NaOH (MeOH:$H_2O$ 4:1) was added to 2'-deoxy-adenine-5'-dimethoxyaspartyl phosphoramidate (238 mg, 0.507 mmoles) and a deprotection reaction was carried out at room temperature while stirring under argon for 2-4 hours. The course of the reaction was monitored by TLC (PrOH:$NH_3$:$H_2O$) until the disappearance of the starting material. Once the starting material has disappeared, the reaction mixture was neutralized by addition of 2M TEAA. The solvent was removed under reduced pressure and the resulting residue was dried by lyophilization. The desired product was purified by silica column chromatography eluting with iPrOH:$NH_3$:$H_2O$ gradient. The product was isolated and concentrated by lyophilization to provide a white solid (137 mg, 61% yield) that was characterised as follows:

$^1H$ NMR (300 MHz, $D_2O$): $\delta$ 8.39 (s, 1H), 8.15 (s, 1H), 6.39 (t, J=7.2, 1H, H1'), 4.61 (dd, J=8.7, 5.7, 1H, H3'), 4.16 (s, 1H, CHCOO$CH_3$), 3.99-3.76 (m, 2H, H5'), 3.75-3.605 (m, 1H, H4'), 2.80-2.64 (m, 1H, H2'), and 2.56-2.30 (m, 3H, H2', $CH_2$) ppm;

$^{13}C$ (300 MHz, $D_2O$): $\delta$ 177.50, 174.14, 155.33, 152.40, 148.38, 139.38, 86.11 (d, J(C,P)=39.0), 83.66 (d, J (C,P)=

18.0), 71.32 (d, J(C,P)=9.0), 63.98 (d, J(C,P)=21.0), 52.19, 39.13 (d, J(C,P)=30), and 36.48 ppm;

$^{31}$P NMR (300 MHz, D$_2$O): δ 6.71; and

MS (ESI): [M−H]=445.1 High resolution MS (ESI): m/z calculated for C$_{14}$H$_{16}$N$_6$O$_9$P 445.0872, actual 445.0864.

Amino acid phosphoramidates 2 to 8 and 2a to 8a were synthesized similarly to 1 and 1a using the same experimental procedure:

2'-deoxy-adenosine-5'-dimethylglutamyl-phosphoramidate (2a) (MW=488.39, C$_{17}$H$_{26}$N$_6$O$_9$P, yield 80.2%) was characterised as follows:

$^1$H NMR (300 MHz, DMSO-d$_6$): δ 8.39 (s, 1H), 8.13 (s, 1H), 7.287 (s, 2H NH$_2$), 6.34 (t, J=6.9, 1H, H1'), 4.41 (s, 1H, H3'), 3.92 (s, 1H, CHCOOCH$_3$), 3.73-3.66 (m, 3H, H4', H5'), 3.55 (s, 3H, CHCOOCH$_3$), 3.52 (s, 3H, CH$_2$COOCH$_3$), 2.77-2.60 (m, 1H, H2'), 2.42-2.18 (m, 3H, H2', CH$_2$), and 1.93-1.58 (m, 2H, CH$_2$) ppm;

$^{13}$C (300 MHz, D$_2$O) δ 176.38 (d, J=15), 175.74, 155.38, 152.56, 148.59, 140.27, 139.75, 118.50, 85.96 (J(C,P)=36.0), 83.60, 71.72, 63.89 (d, J(C,P)=21.0), 53.88, 52.52, 52.05, 38.85, 29.66, and 28.46 (d, J(C,P)=27);

$^{31}$P NMR (300 MHz, D$_2$O): δ 6.19; and

MS (ESI): [M+Na]=459.5 High res. MS (ESI): m/z calculated for C$_{17}$H$_{26}$N$_6$O$_9$P 487.1342 [M−H], actual 487.1319.

2'-deoxy-adenosine-5'-glutamyl-phosphoramidate (2) (MW=460.33, C$_{16}$H$_{21}$N$_6$O$_9$P, yield 61%) was characterised at follows:

$^1$H NMR (300 MHz, D$_2$O): δ 8.39 (s, 1H), 8.13 (s, 1H), 6.40 (t, J=6.9, 1H, H1'), 4.58 (s, 1H, H3'), 4.15 (s, 1H, CHCOOCH$_3$), 3.94-3.76 (m, 2H, H5'), 3.47-3.33 (m, 1H, H4'), 2.78-2.61 (m, 1H, H2'), 2.55-2.41 (m, 1H, H2'), 2.17-2.03 (m, 2H, CH$_2$), and 1.85-1.61 (m, 2H, CH$_2$) ppm;

$^{31}$P NMR (300 MHz, D$_2$O): δ 7.17;

$^{13}$C (500 MHz, D$_2$O) δ 182.88, 181.57, 155.34, 152.50, 148.49, 140.27, 139.77, 118.38, 86.06, 83.56 (d, J(C,P)=40), 71.39, 63.93, 56.71, 39.15, 33.76, and 31.90 ppm; and MS (ESI): [M−H]=459.1 High resolution MS (ESI): m/z calculated for C$_{16}$H$_{21}$N$_6$O$_9$P 459.1029 [M−H], actual 459.1029.

2'-deoxy-adenosine-5'-methylglycidyl-phosphoramidate (3a) (MW 402,29, C$_{13}$H$_{19}$N$_6$O$_7$P, yield 69.8%) was characterised as follows:

$^1$H NMR (300 MHz, DMSO-d$_6$): δ 8.41 (s, 1H), 8.13 (s, 1H), 7.25 (s, 2H, NH$_2$), 6.34 (t, J=6.6), 4.44 (s, 1H, H3'), 3.98-3.88 (m, 1H, H4'), 3.82-3.69 (m, 2H, H5'), 3.55 (s, 3H, CHCOOCH$_3$), 3.50 (d, J 3, 2H, CH$_2$), 2.77-2.61 (m, 1H, H2'), and 2.34-2.17 (m, 1H, H2') ppm;

$^{31}$P NMR (300 MHz, DMSO-d$_6$): δ 4.44 ppm; and

MS (ESI): [M−H]=401.1 High resolution MS (ESI): m/z calculated for C$_{13}$H$_{19}$N$_6$O$_7$P 401.0974 [M−H], actual 401.0987.

2'-deoxy-adenosine-5'-glycidyl-phosphoramidate (3) (MW=388.27, C$_{12}$H$_{17}$N$_6$O$_7$P, yield 22.2%) was characterised as follows:

$^1$H NMR (300 MHz, D$_2$O): δ 8.29 (s, 1H), 8.02 (s, 1H), 6.32 (br s, 1H, H1'), 4.58 (s, 1H, H3'), 4.15 (s, 1H, H4'), 3.87 (s, 2H, H5'), 3.24 (d, J=8.4, 2H, CH$_2$), 2.80-2.60 (m, 1H, H2'), and 2.57-2.38 (m, 1H, H2') ppm;

$^{31}$P NMR (300 MHz, D$_2$O): δ 8.15 ppm; and

MS (ESI): [M−H]=387.1 High resolution MS (ESI): m/z calculated for C$_{12}$H$_{17}$N$_6$O$_7$P 387.0818 actual 387.0810.

2'-deoxy-adenosine-5'-methylalanyl-phosphoramidate (4a) (MW=416.32, C$_{14}$H$_{21}$N$_6$O$_7$P, yield 94.2%) was characterised as follows:

$^1$H NMR (300 MHz, DMSO-d$_6$): δ 8.41 (s, 1H), 8.13 (s, 1H), 7.26 (s, 2H, NH$_2$), 6.35 (t, J=6.6, 1H, H1'), 4.44 (t, J=2.7, 1H, H3'), 3.98-3.88 (m, 1H, H4'), 3.83-3.69 (m, 3H, H5', CHCOOH), 3.51 (s, 3H, CHCOOCH$_3$), 2.77-2.61 (m, 1H, H2'), 2.34-2.20 (m, 1H, H2'), and 1.14 (d, J=1.9, 3H, CH$_3$) ppm;

$^{31}$P NMR (300 MHz, DMSO-d$_6$): δ 3.37; and

MS (ESI): [M−H]=415.1 High resolution MS (ESI): m/z calculated for C$_{14}$H$_{21}$N$_6$O$_7$P 415.1131 actual 415.1143.

2'-deoxy-adenosine-5'-alanyl-phosphoramidate (4) (MW=402.29, C$_{13}$H$_{19}$N$_6$O$_7$P, yield 94.9%) was characterised as follows:

$^1$H NMR (300 MHz, DMSO-d$_6$): δ 8.44 (s, 1H), 8.13 (s, 1H), 7.29 (br s, 2H, NH$_2$), 6.35 (t, J=6.7, 1H, H1'), 4.45 (s, 1H, H3'), 3.96 (s, 1H, H4'), 3.43-3.25 (m, 2H, H5'), 3.45-3.25 (m, 1H, CHCOOH), 2.78-2.60 (m, 1H, H2'), 2.35-2.19 (m, 1H, H2'), and 1.08 (d, J=6.8, 3H, CH$_3$) ppm;

$^{31}$P NMR (300 MHz, D$_2$O): δ 8.15; and

MS (ESI): [M−H]=401.1 High res. MS (ESI): m/z calculated for C$_{13}$H$_{19}$N$_6$O$_7$P 401.0974 actual 401.0957.

2'-deoxy-adenosine-5'-methyltyrosinyl-phosphoramidate (5a) (MW=508.42, C$_{20}$H$_{25}$N$_6$O$_8$P, yield 45%) was characterised as follows:

$^1$H NMR (300 MHz, DMSO-d$_6$): δ 9.46 (s, 1H, OH), 8.42 (s, 1H), 8.12 (s, 1H), 7.27 (s, 2H, NH$_2$), 6.87 (d, J=8.4, 2H, Ar), 6.61 (d, J=8.1, 2H, Ar), 6.34 (t, J=6.9, 1H, H1'), 5.74 (br s, 1H, 3'-OH), 4.39 (s, 1H, H3'), 3.97-3.75 (m, 2H, H4', CHCOOCH$_3$), 3.74-3.59 (m, 2H, H5'), 3.45 (s, 3H, CHCOOCH$_3$), 2.82-2.60 (m, 3H, H2', CH$_2$), and 2.32-2.18 (m, 1H, H2') ppm;

$^{13}$C (300 MHz, D$_2$O) δ 176.53 (d, J(C,P)=18), 155.39, 154.01, 152.52, 148.58, 139.63, 130.20, 128.38, 114.94, 85.88 (J(C,P)=36.0), 83.49, 71.15, 63.78, 56.28, 52.31, 38.92, 38.87, 38.87;

$^{31}$P NMR (300 MHz, DMSO): δ 3.09; and

MS (ESI): [M+H]=509.1 High resolution MS (ESI): m/z calculated for C$_{20}$H$_{25}$N$_6$O$_8$P 509.1549 actual 509.1547.

2'-deoxy-adenosine-5'-tyrosinyl-phosphoramidate (5) (MW=494.39, C$_{19}$H$_{23}$N$_6$O$_8$P, yield 92.1%) was characterised as follows:

$^1$H NMR (300 MHz, DMSO-d$_6$): δ 8.42 (s, 1H), 8.13 (s, 1H), 7.27 (s, 2H, NH$_2$), 6.94 (d, J=8.4, 2H, Ar), 6.56 (d, J=8.4, 2H, Ar), 6.33 (t, J=6.3, 1H, Ht), 5.41 (br s, 1H, 3'-OH), 4.36-4.26 (m, 1H, H3'), 3.83-3.74 (m, 1H, H4'), 3.57-3.56 (m, 2H, H5'), 3.19-3.05 (m, 1H, CHCOOH), 3.45 (s, 3H, CHCOOCH$_3$), 2.45 (d, J=8.3, CH$_2$), 2.60-2.52 (m, 1H, H2'), and 2.28-2.18 (m, 1H, H2');

$^{31}$P NMR (300 MHz, D$_2$O): δ 6.23; and

MS (ESI): [M−H]=493.2 High resolution MS (ESI): m/z calculated for C$_{19}$H$_{23}$N$_6$O$_8$P 493.1237 actual 493.1212.

2'-deoxy-adenosine-5'-methylhistidyl-phosphoramidate (6a) (MW=482.39, C$_{17}$H$_{23}$N$_6$O$_7$P, yield 49.5%) was characterised as follows:

$^1$H NMR (300 MHz, DMSO-d$_6$): δ 8.40 (s, 1H), 8.17 (s, 1H), 8.13 (s, 1H), 7.26 (s, 2H, NH$_2$), 7.05 (s, 1H), 6.35 (t, J=6.6, 1H, H1'), 4.41 (t, J=2.7, 1H, H3'), 3.94-3.92 (s, 1H, CHCOOCH$_3$), 3.83-3.65 (m, 2H, CH$_2$), 3.53 (s, 3H, COOCH$_3$), 2.89 (ddd, J=5.1, 15.0, 33.0, 2H, H5'), 2.75-2.61 (m, 1H, H2'), and 2.33-2.19 (m, 1H, H2');

$^{31}$P NMR (300 MHz, DMSO-d$_6$): δ 3.77; and

MS (ESI): [M+H]=483.0

2'-deoxy-adenosine-5'-histidyl-phosphoramidate (6) (MW=468.36, C$_{16}$H$_{21}$N$_8$O$_7$P, yield 72.9%) was characterised as follows:

$^1$H NMR (300 MHz, D$_2$O): δ 8.30 (d, 1H, J=1.5), 8.29 (s, 1H), 8.03 (s, 1H), 6.95 (s, 1H), 6.33 (t, J=6.9, 1H, H1'), 4.57 (dt, J=3.3, 6.3, 1H, H3'), 4.14 (s, 1H, H3'), 3.94-3.78 (m, 2H, H5'), 3.71-3.59 (m, 1H, CHCOOH), 2.85-2.64 (m, 3H, H2', CH$_2$), and 2.55-2.42 (m, 1H, H2');

$^{13}C$ (600 MHz, DMSO-$d_6$): δ 178.29 (d, J(C,P)=33.7), 155.02, 152.32, 148.42, 139.55, 132.34, 129.21, 118.14, 116.12, 85.67 (d, J(C,P)=36.4), 83.26, 70.93, 63.59 (d, J(C,P)=19.3), 55.86, 38.32, 29.34 (d, J(C,P)=11.2), and 23.52;

$^{31}P$ NMR (300 MHz, $D_2O$): δ 6.44; and

MS (ESI): [M−H]=467.1 High resolution MS (ESI): m/z calculated for $C_{16}H_{21}N_8O_7P$ 467.1193 actual 467.1191.

2'-deoxy-adenosine-5'-methylserinyl-phosphoramidate (7a) (MW=432.32, $C_{14}H_{21}N_6O_8P$, yield 77.8%) was characterised as follows:

$^1H$ NMR (300 MHz, DMSO-$d_6$): δ 8.41 (s, 1H), 8.14 (s, 1H), 7.26 (s, 2H $NH_2$), 6.35 (t, J=6.6, 1H, H1'), 4.50-4.39 (m, 1H, H3'), 4.00-3.89 (m, 1H, H4'), 3.85-3.65 (m, 3H, H5', $CHCOOCH_3$), 3.57 (s, 3H, $CHCOOCH_3$), 3.52 (d, J=4.8, 2H, $CH_2OH$), 2.77-2.60 (m, 1H, H2'), and 2.33-2.02 (m, 1H, H2');

$^{13}C$ (300 MHz, $D_2O$) δ 174.79 (d, J=18), 155.28, 155.45, 148.42, 152.56, 139.64, 118.43, 85.89 (J(C,P)=36.0), 83.61, 71.11 (d, J(C,P)=18), 64.03 (d, J(C,P)=21), 63.55 (d, J(C,P)=24.0), 60.11, 57.38, 52.60, 38.87, and 16.75;

$^{31}P$ NMR (300 MHz, DMSO-$d_6$): δ 4.19; and

MS (ESI): [M−H]=431.1 High resolution MS (ESI): m/z calculated for $C_{14}H_{21}N_6O_8P$ 431.1080 [M−H], actual 431.1109.

2'-deoxy-adenosine-5'-serinyl-phosphoramidate (7) (MW=418.29, $C_{13}H_{19}N_6O_8P$, yield 75.3%) was characterised as follows:

$^1H$ NMR (300 MHz, $D_2O$): δ 8.36 (s, 1H), 8.13 (s, 1H), 6.39 (t, J=7.2, 1H, H1'), 4.578 (dt, J=2.7, 5.4, 1H, H3'), 4.20-4.13 (m, 1H, CHCOOH), 3.90-3.84 (m, 2H, H5'), 3.60-3.42 (m, 3H, H4', $CH_2OH$), 2.78-2.63 (m, 1H, H2'), and 2.55-2.44 (m, 1H, H2');

$^{13}C$ (300 MHz, $D_2O$) δ 174.79 (d, J(C,P)=18), 155.28, 155.45, 148.42, 152.56, 139.64, 118.43, 85.89 (J(C,P)=36.0), 83.61, 71.11 (d, J(C,P)=18), 64.03 (d, J(C,P)=21), 63.55 (d, J(C,P)=24.0), 60.11, 57.38, 52.60, 38.87, and 16.75;

$^{31}P$ NMR (300 MHz, $D_2O$): δ 7.28; and

MS (ESI): [M−H]=417.1 High resolution MS (ESI): m/z calculated for $C_{13}H_{19}N_6O_8P$ 417.0923 [M−H], actual 417.0912.

2'-deoxy-adenosine-5'-dimethylprolinyl-phosphoramidate (8a) (MW=442.36, $C_{16}H_{23}N_6O_7P$, yield 38.9%) was characterised as follows:

$^1H$ NMR (300 MHz, DMSO-$d_6$): δ 8.43 (s, 1H), 8.13 (s, 1H), 7.28 (s, 2H $NH_2$), 6.35 (t, J=6.9, 1H, H1'), 4.44 (s, 1H, H3'), 4.14-4.00 (s, 1H, H4'), 3.88-3.64 (m, 3H, H5', $CHCOOCH_3$), 3.53 (s, 3H, $CHCOOCH_3$), 3.25-3.10 (m, 2H, $CH_2$), 3.10-2.98 (m, 2H, $CH_2$), 2.97-2.83 (m, 2H, $CH_2$), 2.81-2.64 (m, 1H, H2'), 2.37-2.198 (m, 1H, H2'), and 2.11-1.85 (m, 1H, H2'); and MS (ESI): [M−1]=441.1. High resolution MS (ESI): m/z calculated for $C_{16}H_{23}N_6O_7P$ 441.1287 actual 441.1266.

2'-deoxy-adenosine-5'-prolinyl-phosphoramidate (8) (MW=428.23, $C_{16}H_{21}N_6O_7P$, yield 64.5%) was characterised as follows:

$^1H$ NMR (300 MHz, DMSO-$d_6$): δ 8.32 (s, 1H), 8.13 (s, 1H), 6.37 (t, J=6.3, 1H, H1'), 4.65-4.55 (m, 1H, H3'), 4.19-4.07 (m, 1H, H4'), 3.96-3.72 (m, 3H, H5', CHCOOH), 3.02-2.84 (m, 2H, $CH_2$), 2.83-2.60 (m, 1H, $CH_2$), 2.60-2.47 (m, 1H, $CH_2$), 2.04-1.83 (m, 1H, H2'), and 1.76-1.47 (m, 3H, H2', $CH_2$);

MS (ESI): [M−1]=427.1. High resolution MS (ESI): m/z calculated for $C_{16}H_{21}N_6O_7P$ 427.1131 actual 427.1116.

Example 2

Biological Assay

RT and DNA Polymerase Assays

Primers and templates used in this study (an underlined region is a sequence complementary to the primer) were as follows:

SEQ ID NO: 1
5'-$^{33}$P-CAGGAAACAGCTATGAC-3'
(P1)

SEQ ID NO: 2
5'-CCCCT<u>GTCATAGCTGTTTCCTG</u>-3'
(T1)

SEQ ID NO: 3
5'-CCTTT<u>GTCATAGCTGTTTCCT</u>CCCTTT<u>GTCATAGCTGTTTCCTG</u>-3'
(T3)

SEQ ID NO: 4
5'-CTTTTTTT<u>GTCATAGCTGTTTCCTGC</u>-3'
(T5)

$^{33}$P 5'-Labeling of a Primer (P1)

Labeling of a primer (200 pmol, P1) was accomplished with 5'-[γ-$^{33}$P]ATP (GE Healthcare) and T4 Polynucleotide kinase (NEB) and purified using Illustra™ MicroSpin™ G-25 columns (GE Healthcare).

Single Nucleotide Incorporation by HIV Reverse Transcripates (HIV RT)

A typical single nucleotide incorporation and primer extension assays using HIV RT polymerase was carried out similar to one described in the literature. HIV RT polymerase was purchased from GE Healthcare and was supplied as either 12 or 30 U/μL stock solution. The final concentration of HIV RT in a reaction mixture was 0.03-0.003 U/μL. A primer/template duplex mixture was prepared by combining appropriate amounts of a 5'-$^{33}$P-labeled primer (P1) and a template in 1:2 molar ratio to provide a 4× solution with 0.5 μM primer concentration. The polymerase reactions were carried out in a 5×RT buffer containing 250 mM TRIS.HCL, 250 mM KCl, 50 mM $MgCl_2$, 2.5 mM spermidine, 50 mM DTT, pH 8.3. For the single nucleotide incorporation assay, a P1/T1 primer-template pair was used whereas the primer extension study was performed with P1/T3 and P1/T5 primer-template pairs.

Briefly, a mixture containing 5 μL of the 4× primer/DNA duplex solution and 5 μL of 4× polymerase solution was pre-incubated at 37° C. for 2 minutes to ensure formation a DNA polymerase/DNA duplex complex. Simultaneously, 2× solutions of dNTP to provide final concentrations of 100 μM, 200 μM, 500 μM and 1 mM were also pre-incubated at 37° C. for 2 minutes as well. The polymerase reaction in a total volume of 20 μL was initiated by addition of 10 μL of the 2× dNTP solution to the DNA polymerase/DNA duplex mixture. The reactions were run at 37° C. and aliquots (2.5 μL) were removed at specified time points and mixed with 10 μL of a quenching buffer containing 80% formamide, 2 mM EDTA, 1×TBE. Quenched reactions were analyzed by loading 2 μL of a reaction sample onto a 20% denaturing polyacrylamide: gel (19:1 acrylamide:bisacrylamide, 7M urea, 0.4 mm×30 cm×40 cm) made in 1×TBE buffer (90 mM Tris-borate, 2 mM EDTA, pH 8.3). The gel was pre-equilibrated for 2 hours before loading and the reactions were run along with a tracking dye marker containing bromophenol blue (BB) and xylene cyanol (XC) until the BB dye had run ⅔ of the total gel length. For visualization, gels were scanned using a Cyclone Phosphoroimager.

Primer extension study with HIV RT and Therminator DNA polymerase was performed in a fashion similar to the single nucleotide incorporation experiments. Two sets of primer/template complexes were used: P1/T3 and P1/T5.

Single Nucleotide Incorporation by Therminator DNA Polymerase

In the case of Therminator DNA polymerase, the enzyme was obtained from Westburg (NEB) (2 U/μL) and the reactions were carried out in a 10× Thermopol reaction buffer containing 20 mM TRIS.HCl, 10 mM KCl, 2 mM MgSO$_4$, 0.1% Triton X-100, pH 8.8. The final concentration of the Therminator DNA pol in the reaction mixture was $8.33 \times 10^{-4}$ U/μL. The polymerase reaction involving Therminator DNA polymerase or any other thermostable polymerase (Vent (exo$^-$), Taq DNA polymerase) was carried out in a similar way as the HIV RT reaction with some modifications. The dNTP solutions and the primer/template/DNA polymerase mixture solutions were topped with mineral oil (30-60 μL) and pre-incubated at 70° C. for 2 minutes. The polymerase reactions were performed at 70° C. as well.

Steady State Kinetics of Single Nucleotide Incorporation

The steady steate kinetics of a single nucleotide incorporation of an amino acid phosphoramidate (AA-dAMP) and of a natural nucleoside triphosphate (dATP) was determined by the gel-based polymerase assay. In all the experiments, the template T1 and the primer P1 were used (Table 1). The primer and template in 1:2 molar ratio were hybridized in a buffer containing 20 mM TRIS.HCl, 10 mM KCl, 2 mM MgSO$_4$, 0.1% Triton X-100, pH 8.8 and used in an amount to provide 125 nM concentration of the primer in each 12 μL reaction. The range of concentrations for amino acid phosphoramidates was optimized according to a $K_m$ value for the incorporation of an individual nucleotide. In the case of HIV RT (Amersham Bioscience (GE Healthcare), 30 U/μL), reaction mixtures containing the enzyme in concentration to attain 5-20% conversion and appropriate substrate concentration (nucleoside phosphoramidate or natural dNTP) were incubated at 37° C. and run for 8-10 different time intervals. Kinetic analysis of single nucleotide incorporation by Therminator DNA polymerase (NEB, 2 U/μL) was performed similarly except the incubations and polymerase reactions, which were carried out at 70° C. To prevent solvent condensation/evaporation, the reaction mixtures were topped with mineral oil. The reactions were quenched by addition of the buffer containing 80% formamide, 2 mM EDTA, 1×TBE buffer. The analysis of polymerase reactions was performed by polyacrylamide gel electrophoresis (20% (19:1 mono:bis), 7M urea, 30 cm×40 cm×0.4 mm). The relative band intensities were measured using OptiQuant software. The rates of incorporation (V) were calculated based on the percentage of the extension production (n+1 band). The kinetic parameters ($V_{max}$ and $K_m$) were determined by plotting V (pmol/min·U) versus substrate concentration and fitting the data point to a rectangular hyperbola using GraphPad Prism software.

Example 3

Synthesis of Oligonucleotides

Single Nucleotide Incorporation by HIV RT

HIV reverse transcriptase is involved in the copying of the HIV genome and uses deoxy- and ribonucleotides as substrates. Furthermore, HIV RT is an error-prone polymerase and has high mutation rate. Therefore, the essential role of the HIV RT in viral replication and its flexibility and tolerance toward modified nucleotides renders this enzyme a primary target in treatment of HIV infection. In the presented study, the ability of HIV RT to incorporate a series of amino acid phosphoramidate nucleoside analogs was investigated by the gel-based single nucleotide incorporation assay.

Figure 3:
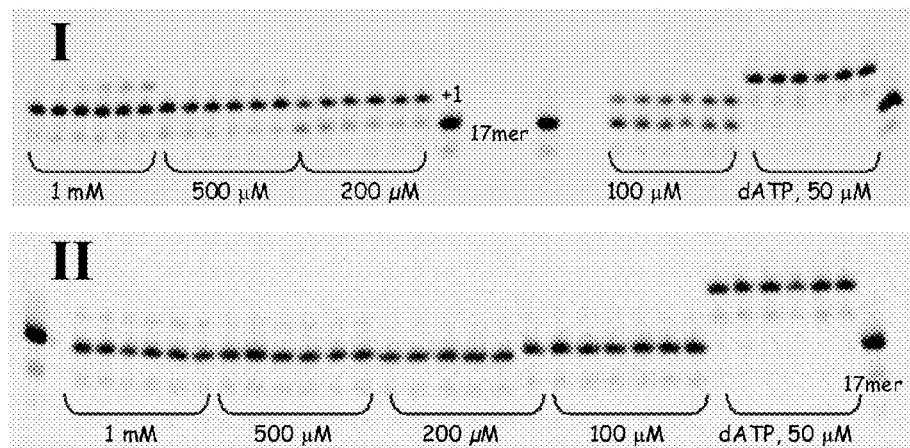
FIG. 3 shows (panel I) the incorporation of Asp-dAMP (1) by HIV RT in comparison with (panel II) the incorporation of methyl ester Asp-dAMP (1a) by HIV RT. Reaction conditions: Primer (P1) was 5'-labeled with $^{33}$P followed by annealing to a template T1; 125 nM primer/template (P1/T1), [HIV-RT]=0.03 U/μL, time intervals: 5, 15, 30, 60, 90 and 120 minutes.

Among amino acid phosphoramidate nucleosides (1-6 and 1a-6a), unexpected and remarkable results were observed with Asp-dAMP (1) (FIG. 3).

Figure 4:
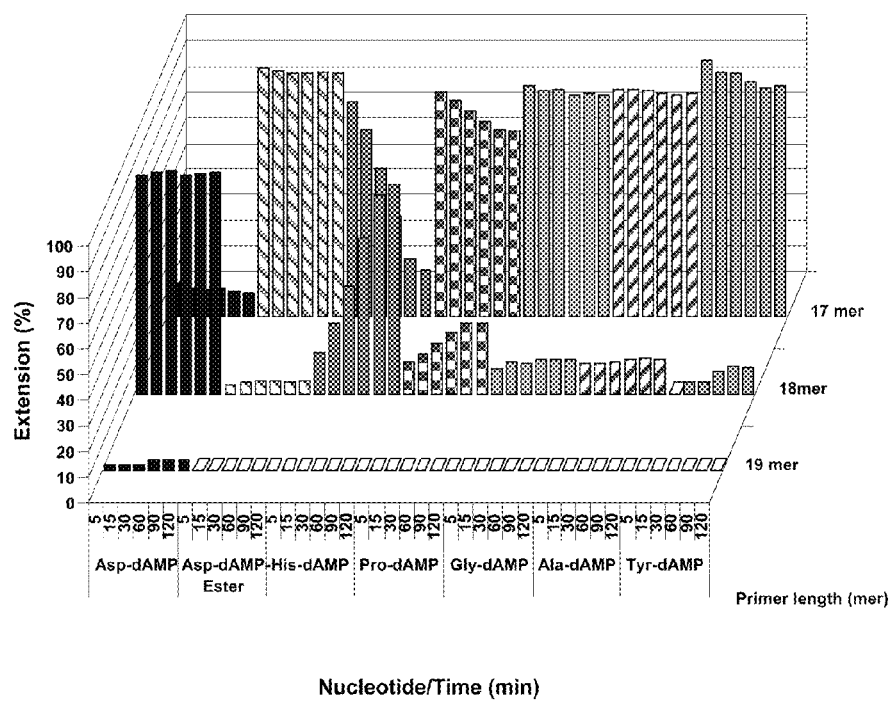
FIG. 4 shows the efficiency of phosphoramidate incorporation by HIV RT. Reaction conditions: Primer (P1) was 5'-labeled with $^{33}$P followed by annealing to a template T1; 125 nM primer/template (P1/T1), [HIV-RT]=0.03 U/μL, time intervals: 5, 15, 30, 60, 90 and 120 minutes.

This phosphoramidate analog was recognized by HIV RT and efficiently incorporated into a growing primer strand resulting in 90% conversion to a (n+1) strand in 60 min (500 μM nucleotide concentration). At the same conditions, incorporation of His-dAMP(6), Gly-dAMP (3), and Pro-dAMP (8) was 1.5, 6.5, and 3.7 fold less efficient, respectively. Efficient incorporation of Asp-dAMP (24.1%) was also observed when the substrate concentration was decreased 10 fold. However, significantly lesser incorporation of amino acid phosphoramidate was detected for nucleosides coupled to non-polar, hydrophobic amino acids. Ala-dAMP and Tyr-dAMP behaved as poor substrates leading to merely 7- and 10-fold reduction in primer extension, respectively (FIG. 4).

Interestingly, no incorporation occurred when respective methyl ester derivatives 1a-8a were used as substrates in the polymerase reaction. Another unexpected result was observed with Glu-dAMP analog (2) that also acted very poorly as a HIV RT substrate. These observations suggest that recognition and incorporation of AA dAMPs are likely to be dictated by the chemical structure and electrostatics of the amino acid moiety.

Single Nucleotide Incorporation by Therminator DNA Polymerase

Figure 5:
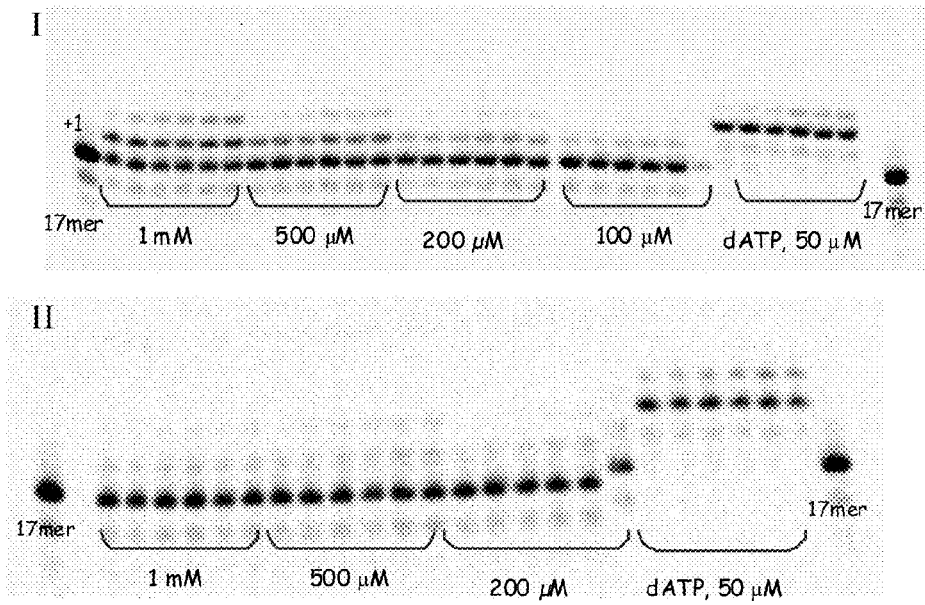
FIG. 5 shows (panel I) the incorporation of Asp-dAMP (1) by Therminator DNA polymerase in comparison with (panel II) the incorporation of methyl ester Asp-dAMP (1a) by Therminator DNA polymerase. Reaction conditions: Primer (P1) was 5'-labeled with $^{33}$P followed by annealing to a template T1; 125 nM primer/template (P1/T1), [Therminator]=0.03 U/μL, [primer]=0.125 μM, time intervals: 5, 15, 30, 60, 90 and 120 minutes.
Figure 6:
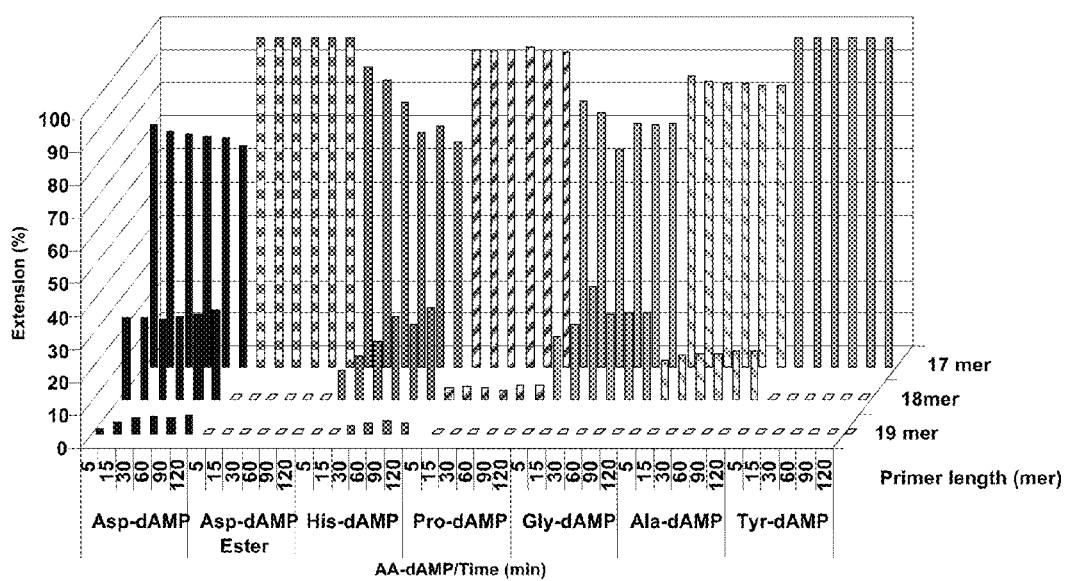
FIG. 6 shows the efficiency of phosphoramidate incorporation by Therminator DNA polymerase. Reaction conditions: Primer (P1) was 5'-labeled with $^{33}$P followed by annealing to a template T1; 125 nM primer/template (P1/T1), [Therminator]=0.03 U/μL, [primer]=0.125 μM, time intervals: 5, 15, 30, 60, 90 and 120 minutes.

Yet another polymerase enzyme that demonstrates similar trends in recognition and utilization of AA-dAMPs is Therminator DNA polymerase, a variant of (9° N-7) Thermococcus sp. DNA polymerase. This enzyme demonstrated effective recognition and incorporation of a number of nucleotides bearing unnatural nucleobase and sugar moieties. Likewise, probing of AA-dAMP incorporation directed by Therminator DNA polymerase revealed property of analogs 1, 3, and 6 to act effectively as alternative substrates in the DNA polymerization reaction (FIGS. 5 and 6).

Yet again, the best results were obtained with Asp-dAMP, which led to 25.2% primer extension over 60 min at 500 μM nucleoside concentration. At the same conditions, the similar results were obtained for Gly-dAMP and His-dAMP (26% and 25.4% primer extension, respectively). In the case of Glu-dAMP and methyl protected AA-dAMPs, Therminator DNA polymerase displays selectivity analogous to HIV reverse transcriptase and fails to direct incorporation of those phosphoramidate analogs (FIG. 6).

Single Nucleotide Incorporation by Other DNA Polymerases

Figure 7:
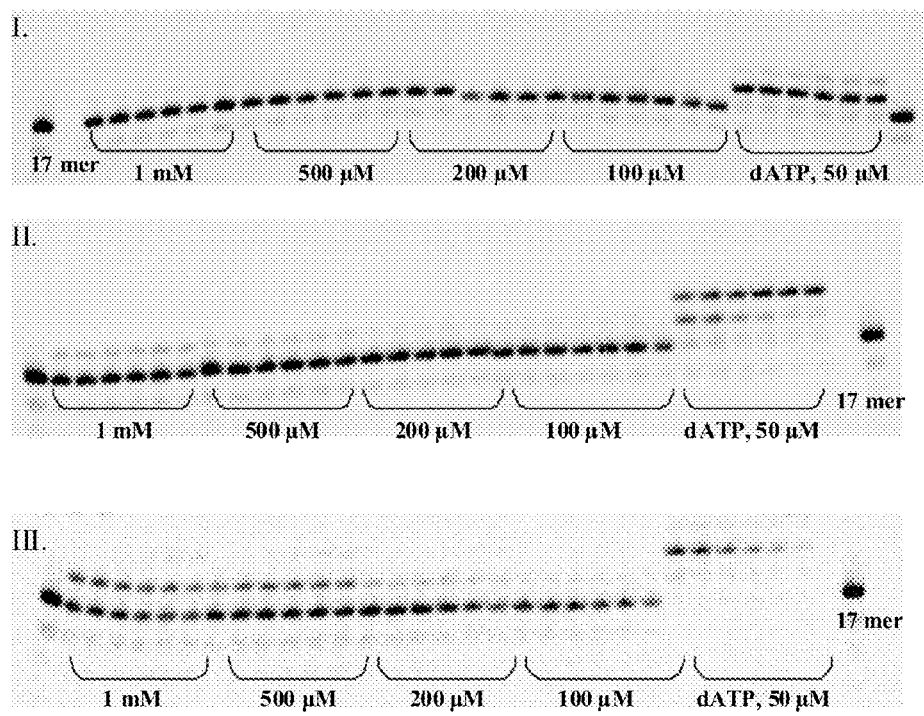
FIG. 7 shows (panel I) the incorporation of Asp-dAMP (1) by Taq DNA polymerase, then (panel II) the incorporation of Asp-dAMP (1) by Vent (exo) DNA polymerase, and (panel III) the incorporation of Asp-dAMP (1) by Klenow Fragment (KF) (exo$^-$) DNA polymerase. Reaction conditions: Primer (P1) was 5'-labeled with $^{33}$P followed by annealing to a template T1; 125 nM primer/template (P1/T1), [Taq]=0.005 U/μL, [Vent]=0.005 U/μL, [KF]=0.05 U/μL; time intervals: 5, 15, 30, 60, 90 and 120 minutes.

The remarkable property of Asp-dAMP encouraged further investigation and testing 1 as a substrate for other DNA polymerases. However, in the case of Taq, Vent (exo$^-$), and KF (exo$^-$) DNA polymerases, recognition and incorporation efficiency were significantly less appealing. Incorporation and primer extension were observed only in the case of KF (exo$^-$) DNA pol demonstrating 32.5% conversion of the primer strand in 60 minutes. This is in contrast to Taq and Vent (exo$^-$) DNA polymerases that failed to insert 1 into a growing primer strand. The diversity in incorporation selectivity that are observed among the polymerases (Therminator, Taq, Vent (exo$^-$), KF (exo$^-$), and HIV reverse transcriptase) could indicate the differences in the active site flexibility and tolerance to the triphosphate modifications (FIG. 7).

Primer Extension by HIV RT

The further investigation of Asp-dAMP recognition by the reverse transcriptase focused on ability of HIV RT to direct template dependent incorporation of more than one phosphoramidate nucleosides. For this purpose, template T3 containing a string of three thymidine nucleobases flanked with cytidine nucleobases at the 3' end and the template T5 that has an overhang of seven thymidine residues were used. Ability to HIV RT to synthesize a DNA sequence using phosphoramidate nucleotides as substrates was tested among Asp-dAMP, His-dAMP, Gly-dAMP, and Pro-dAMP.

Figure 8:
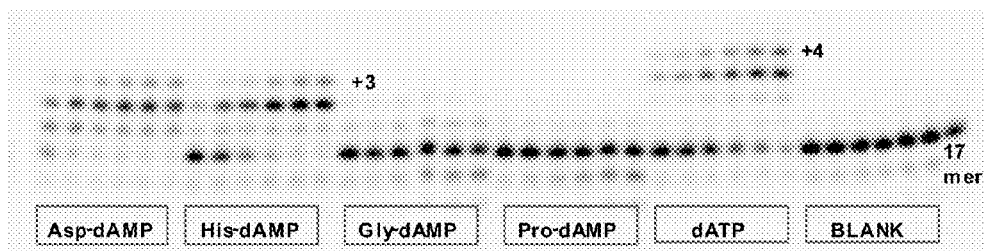
FIG. 8 shows primer extension with amino acid phosphoramidates by HIV RT. Reaction conditions: Primer (P1) was 5'-labeled with $^{33}$P followed by annealing to a template T3; 125 nM primer/template (P1/T3), [AA-dAMP]=500 μM; [dATP]=50 μM; [HIV RT]=0.03 U/μL; time intervals: 5, 15, 30, 60, 90 and 120 minutes. Blank: 125 nM primer/template (P1/T3), [HIV RT]=0.03 U/μL, no nucleotide substrate.
Figure 9:
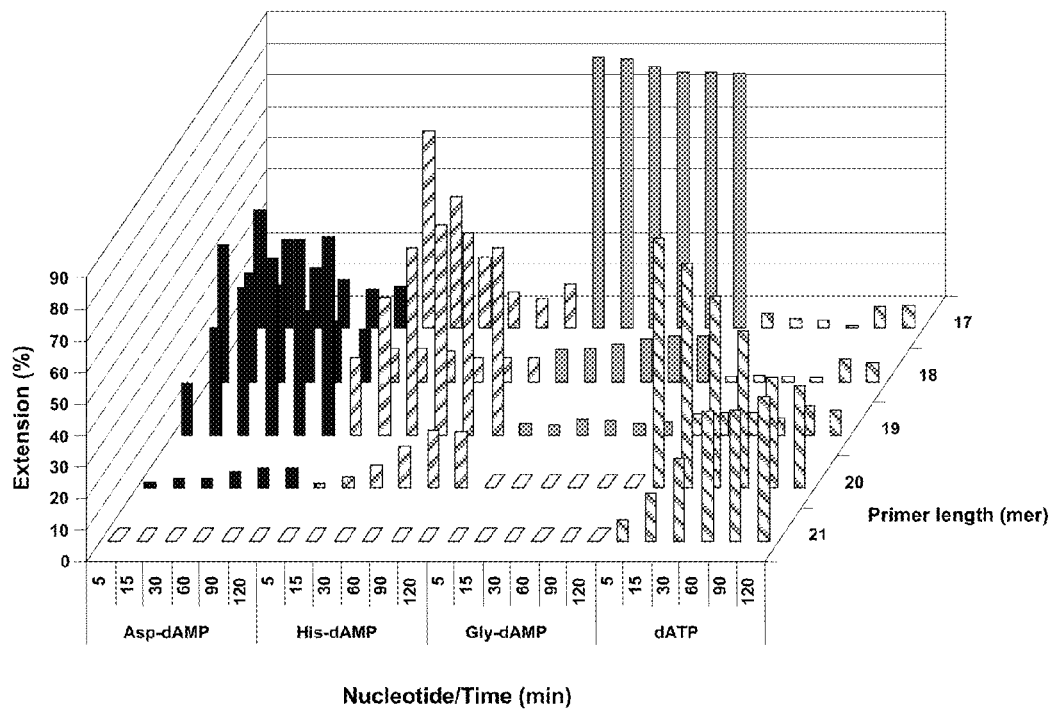
FIG. 9 shows the extension efficiency of HIV reverse transcriptase. Reaction conditions: Primer (P1) was 5'-labeled with $^{33}$P followed by annealing to a template T3; 125 nM primer/template (P1/T3), [AA-dAMP]=500 μM; [dATP]=50 μM; [HIV RT]=0.03 U/μL; time points: 5, 15, 30, 60, 90 and 120 minutes. Blank: 125 nM primer/template (P1/T3), [HIV RT]=0.03 U/μL, no nucleotide substrate.

Among this series of phosphoramidate nucleoside, the most encouraging results using T3 template were observed with Asp-dAMP and His-dAMP which were used by HIV RT to extend a primer with three adenine nucleobases (n+3 product) (FIGS. 8 and 9).

However, after 60 minutes of the polymerase reaction the (n+2) product predominates over the (n+3) product (56.3% vs. 5.2% for Asp-dAMP and 67.1% vs. 13.5% for His-dAMP). Interestingly, efficiency of DNA synthesis with His-dAMP at 500 µM substrate concentration is similar or better to that when Asp-dAMP serves as the substrate (67.1% vs. 56.3%, respectively, for the synthesis of the (n+2) primer). This is in contrast to the single nucleotide incorporation results that indicate that His-dAMP is worse than Asp-dAMP as a substrate for HIV RT.

Figure 10:
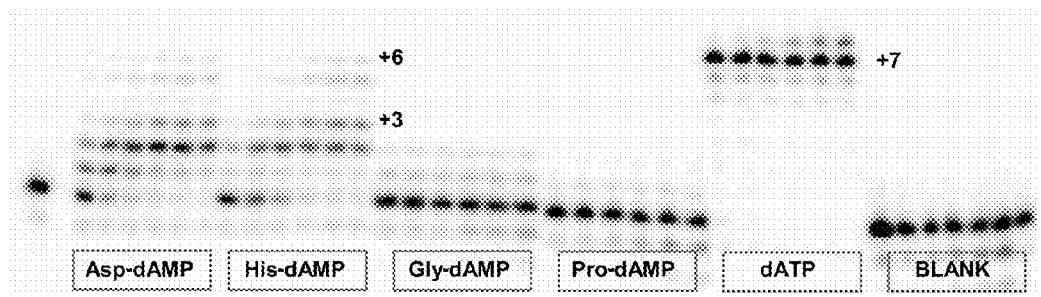
FIG. 10 shows primer extension with amino acid phosphoramidates by HIV RT. Reaction conditions: Primer (P1) was 5'-labeled with $^{33}$P followed by annealing to a template T5; 125 nM primer/template (P1/T5), [AA-dAMP]=500 μM; [dATP]=50 μM; [HIV RT]=0.03 U/μL; time points: 5, 15, 30, 60, 90 and 120 minutes. Blank: 125 nM primer/template (P1/T5), [HIV RT]=0.03 U/μL, no nucleotide substrate.

In the case of the T5 template with the overhang of seven thymidine nucleobases, HIV RT indeed generates (n+6) and (n+7) products at a very little extent while the (n+2) and (n+3) products are prevalent (FIG. 10). The obvious stalling of the HIV RT polymerase after incorporation of two adenine nucleobases might indicate substrate inhibition or a template sequence effect. The primer strand extension for one hour with 500 µM of Gly-dAMP or Pro-dAMP takes place with low efficiency and does not result in the formation of the full-length extension products.

Primer Extension by Therminator DNA Polymerase

Figure 11:
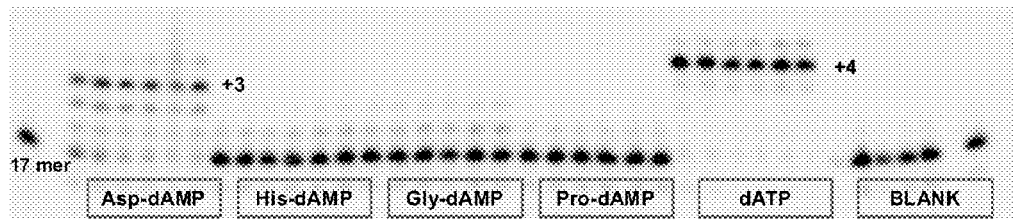
FIG. 11 shows primer extension with amino acid phosphoramidates by Therminator DNA polymerase. Reactions conditions: Primer (P1) was 5'-labeled with $^{33}$P followed by annealing to a template T3; 125 nM primer/template (P1/T3), [AA-dAMP]=500 μM; [dATP]=50 μM; [Therminator]=8×

The Therminator DNA pol mediated addition of amino acid phosphoramidate nucleosides instead of natural dNTPs at the 3' terminal end was investigated for several AA-dAMPs. Similarly, to the case of HIV RT, the best results were observed with AspdAMP phosphoramidate, which was successfully incorporated across from a string of thymidine residues (T3 template) to provide a (n+3) product (FIG. 11). However, when His-dAMP and Gly-dAMP were used as substrates for Therminator DNA polymerase, the primer extension took place with significantly lesser efficiency (13.6% and 18.1% of primer extension, respectively) with the (n+1) product being predominant and halted after addition of two nucleoside phosphoramidate residues (FIG. 12). The primer extension with Pro-dAMP was very ineffective and resulted only in addition of one nucleoside phosphoramidate residue at the primer's end.

In the case of the T5 template with the overhang of seven thymidine residues, the predominant product of the primer extension was the (n+2) oligonucleotide. Nonetheless, Therminator DNA polymerase was able to carry out the extension of the T5 primer with Asp-dAMP phosphoramidate and incorporate up to five adenine residues.

HIV Reverse Transcriptase

Steady state kinetics for single nucleotide incorporation was determined by the gel based polymerase assay. The kinetics analysis (Table 1) shows that $V_{max}$ for incorporation of 1 is only 3 fold lower than that for a HIV RT natural substrate (dATP), however, the $K_m$ value for Asp-dAMP is 400 fold higher as compared to dATP. Therefore, as a result, the specificity, or a $V_{max}/K_m$ value, for insertion of amino acid phosphoramidate against a natural nucleobase is reduced 1300 fold. The significantly higher $K_m$ value for an unnatural amino acid phosphoramidate analog than one for the natural substrate suggests that the phosphoramidate substrate dissociates from the active site more readily and faster. However, small difference in $V_{max}$ values (3 fold) indicates that once the amino acid phosphoramidate substrate is bound at the active site nucleotidyl transfer takes place with the efficiency and the rate slightly lower than in the case of the natural substrate. It probably also indicates that the bound Asp-dAMP fits the polymerase active site well and adapts geometry and orientation that closely resembles dATP.

TABLE 2 steady state kinetics of Asp-dAMP incorporation by HIV RT

| Substrate | $V_{max}$ (pmol/min · U) | $K_M$ (µM) | $V_{max}/K_M$ (×10$^6$) |
|---|---|---|---|
| dATP | 8.39 ± 0.82 | 0.46 ± 0.15 | 18.1 |
| 1 | 2.63 ± 0.13 | 185.3 ± 24.55 | 0.014 |

Example 4

Primer Extension Experiments with Other Aspartic Acid Phosphoramidate Nucleotides Highly purified 2'-deoxynucleoside triphosphates used in DNA polymerase reactions were purchased from Pharmacia.

Synthesis of Aspartic Acid Phosphoramidate Nucleosides

2'-Deoxynucleoside 5'-monophosphate (1.00 mmol) and L-aspartic acid methyl ester/N-Me-L-aspartic acid methyl ester (7.00 mmol) were dissolved in $^t$BuOH (9.1 mL) and water (3.1 mL). A few drops of triethylamine were added to facilitate dissolution. Then, a solution of DCC (5.00 mmol) in $^t$BuOH (6.7 mL) was added and the reaction mixture was refluxed for 2-3 hours while stirring under argon. The progress of the reaction was followed by TLC using a iPrOH:NH$_3$:H$_2$O (7:1:2) mixture. Upon completion, the reaction mixture was cooled down and the solvents were removed by rotatory evaporation. The residue was resuspended in water and extracted with diethyl ether. The aqueous phase was then lyophilized. The residue was subjected to column chromatography on silica gel using the following solvent gradient: CHCl$_3$:MeOH (5:1), CHCl$_3$:MeOH:H$_2$O (5:2:0.25), CHCl$_3$:MeOH:H$_2$O (5:3:0.5), and finally CHCl$_3$:MeOH:H$_2$O (5:4:1). The product obtained was treated with 1.4 M K$_2$CO$_3$ (20 eq.) in MeOH:H$_2$O (1:2) and the reaction mixture was allowed to stir at room temperature. The course of the reaction was monitored by TLC using a iPrOH:NH$_3$:H$_2$O (6:3:1) mixture until disappearance of the starting material. Then, the solvents were removed under reduced pressure. The residue was subjected to column chromatography on silica gel using the following solvent gradient: iPrOH, iPrOH:NH$_3$:H$_2$O (7:1:1).

2'-Deoxyadenosine-5'-N-methylaspartyl phosphoramidate (12)

The above general procedure was followed using 2'-deoxyadenosine 5'-monophosphate (80 mg, 0.24 mmol) and N-Me-L-aspartic acid methyl esther. After 2 hours at reflux, the solid obtained was treated with 2.8 mL of 1.4M K$_2$CO$_3$ in MeOH—H$_2$O for 3 days. 2'-deoxyadenosine-5'-methylaspartyl phosphoramidate (12, 58 mg, 52% yield for two steps) was obtained as a white solid which was characterised as follows:

$^1$H NMR (300 MHz, D$_2$O) δ 8.49 (1H, s), 8.24 (1H, s), 6.50 (1H, m), 4.72 (1H, m), 4.42-4.26 (2H, m), 3.99-3.97 (2H, m), 2.88-2.56 (2H, m), 2.52-2.35 (3H, m), and 2.46 (3H, d, J=9.2);

$^{13}$C NMR (75 MHz, D$_2$O) δ 180.2, 179.8 (d, J=5.1), 155.3, 152.5, 148.4, 139.7, 118.4, 86.0 (d, J=9.1), 83.5, 71.1, 63.9 (d, J=5.5), 59.5 (d, J=3.7), 39.0, 38.6, and 29.1 (d, J=4.1);

$^{31}$P NMR (121 MHz, D$_2$O): δ 9.03; and

HRMS calculated for C$_{15}$H$_{20}$N$_6$O$_9$P (M−H$^+$) 459.10294, found 459.10365.

2'-Deoxyguanosine-5'-aspartyl phosphoramidate (9)

The above general procedure was followed using 2'-deoxyguanosine 5'-monophosphate (130 mg, 0.37 mmol) and L-aspartic acid methyl ester. After 2 hours at reflux, the solid obtained was treated with 4.9 mL of 1.4M K$_2$CO$_3$ in MeOH—H$_2$O for 3 days. 2'-Deoxyguanosine-5'-aspartyl phosphoramidate (9, 104 mg, 60% yield for two steps) was obtained as a white solid which was characterised as follows:

$^1$H NMR (300 MHz, D$_2$O) δ 7.98 (1H, s), 6.16 (1H, m), 4.56 (1H, m), 4.10 (1H, m), 3.94-3.82 (2H, m), 3.67 (1H, m), 2.64 (1H, m), and 2.52-2.35 (3H, m);

$^{13}$C NMR (75 MHz, D$_2$O) δ 180.5 (d, J=4.4), 178.5, 158.8, 153.8, 151.3, 137.4, 116.0, 85.9 (d, J=9.9), 83.4 (d, J=3.0), 71.4, 64.0 (d, J=5.1), 54.2, 42.2 (d, J=5.5), and 38.6;

$^{31}$P NMR (121 MHz, D$_2$O): δ 6.82; and

HRMS calculated for C$_{14}$H$_{20}$N$_6$O$_{10}$P (M+H$^+$) 463.0979, found 463.09544.

2'-Deoxythymidine-5'-aspartyl phosphoramidate (10)

The above general procedure was followed using 2'-deoxythymidine 5'-monophosphate (125 mg, 0.39 mmol) and L-aspartic acid methyl ester. After 2 hours at reflux, the solid obtained was treated with 5.3 mL of 1.4M K$_2$CO$_3$ in MeOH—H$_2$O for 3 days. 2'-deoxythymidine-5'-aspartyl phosphoramidate (10μ, 127 mg, 75% yield for two steps) was obtained as a white solid which was characterised as follows:

$^1$H NMR (500 MHz, D$_2$O) δ 7.72 (1H, s), 6.27 (1H, m), 4.48 (1H, m), 4.07 (1H, m), 3.94-3.84 (2H, m), 3.71 (1H, m), 2.51-2.41 (2H, m), 2.30-2.24 (2H, m), and 1.85 (3H, s);

$^{13}$C NMR (125 MHz, D$_2$O) δ 180.5, 178.5, 166.2, 151.4, 137.1, 111.4, 85.5 (d, J=9.1), 84.6, 70.9, 63.6, 54.2, 44.7, 38.2, and 11.3;

$^{31}$P NMR (202 MHz, D$_2$O): δ 6.54; and

HRMS calculated for C$_{14}$H$_{21}$N$_3$O$_{11}$P (M+H$^+$) 438.09137, found 438.08937.

2'-Deoxycytidine-5'-aspartyl phosphoramidate (11)

The above general procedure was followed using 2'-deoxycytidine 5'-monophosphate (130 mg, 0.40 mmol) and L-aspartic acid methyl ester. After 2 hours at reflux, the solid that was obtained was treated with 4.7 mL of 1.4M K$_2$CO$_3$ in MeOH—H$_2$O for 3 days. 2'-deoxycytidine-5'-aspartyl phosphoramidate (11, 117 mg, 70% yield for two steps) was obtained as a white solid which was characterised as follows:

$^1$H NMR (300 MHz, D$_2$O) δ 7.96 (1H, d, J=7.6), 6.32 (1H, t, J=6.6), 6.13 (1H, d, J=7.6), 4.53 (1H, m), 4.17 (1H, m), 4.00-3.98 (2H, m), 3.77 (1H, m), 2.62-2.48 (2H, m), 2.41 (1H, ddd, J=3.7, J=6.6, J=14.0), and 2.29 (1H, ddd, J=6.6, J=7.1, J=14.0);

$^{13}$C NMR (75 MHz, D$_2$O) δ 180.8 (d, J=4.1), 179.0, 165.5, 156.8, 141.8, 96.4, 85.9, 85.7, 70.8, 63.8 (d, J=5.0), 54.5, 42.8 (d, J=6.2), and 39.4;

$^{31}$P NMR (121 MHz, D$_2$O): δ 6.87; and

HRMS calculated for C$_{13}$H$_{18}$N$_4$O$_{10}$P (M−H$^+$) 421.07606, found 421.07665.

Oligodeoxyribonucleotides

Primers and templates used to study the chain elongation reaction with different amino acid phosphoramidate derivatives.

| | | |
|---|---|---|
| SEQ ID NO: 1 | 5'-$^{33}$P-CAGGAAACAGCTATGAC-3' | (P1) |
| SEQ ID NO: 8 | 5'-$^{33}$P-CAGGAAACAGCTATGACTGA-3' | (P2) |
| SEQ ID NO: 2 | 5'-CCCCTGTCATAGCTGTTTCCTG-3' | (T1) |
| SEQ ID NO: 5 | 5'-TTTTCGTCATAGCTGTTTCCTG-3' | (T2) |
| SEQ ID NO: 6 | 5'-AAAAAGTCAGTCATAGCTGTTTCCTG-3' | (T4) |
| SEQ ID NO: 7 | 5'-GTCATAGCTGTTTCCTG-3' | (A) |

Oligodeoxyribonucleotides P1, P2, T1, T2, T4 and A were purchased from Sigma Genosys. The concentrations were determined using a Varian Cary 300 Bio UV-spectrophotometer.

The lyophilized oligonucleotides were dissolved in DEPC-treated water and stored at ±20° C. The primer oligonucleotides were 5'-$^{33}$P-labeled with 5'-[γ$^{33}$P]ATP (GE Healthcare) using T4 Polynucleotide kinase (NEB) following standard procedures. Labeled oligonucleotides were further purified using Illustra™ Microspin™ G-25 columns (GE Healthcare).

DNA Polymerase Reactions

End-labeled primers were annealed to their template by combining primer and templates in a molar ratio of 1:2 and heating the mixture to 70° C. for 10 minutes, followed by slow cooling to room temperature over a period of 2.5 hours. For the incorporation of L-Asp-dGMP (9), L-Asp-dTMP (10), L-Asp-dCMP (11), and N-Me-Asp-dAMP (12) (see FIG. 13), the primer P1 was annealed to templates T1, T2, T4 or A and P2 was annealed to T4. A series of 20 μL reactions was performed for the enzyme HIV reverse transcriptase (GE Healthcare, 30 U/4 stock solution). The final mixture contained 125 nM primer-template complex, RT buffer (250 mM TrisHCl, 250 mM KCl, 50 mM MgCl$_2$, 2.5 mM spermidine, 50 mM DTT, pH 8.3), 0.03 U/μL HIV RT and different amino acid phosphoramidates building blocks concentrations. In the control reaction with the natural nucleotide, 10 μM or 50 μM dGTP, dTTP, dATP or dCTP were used. The mixture was incubated at 37° C. for 3 minutes and aliquots were quenched after 5, 10, 20, 30, 60 and 120 minutes respectively.

Kinetics Experiments

To determine the kinetic parameters of the incorporation of Asp-dGMP (9), Asp-dTMP (10), Asp-dCMP (11) or dGTP, dTTP, dCTP, a steady-state kinetic assay was carried out. The reaction mixture was started by adding HIV reverse transcriptase to P1-T2, P1-T4 or P2T4 complex, buffer and Asp-dGMP, Asp-dTMP, Asp-dCMP or dGTP, dTTP, dCTP. The final mixture (20 μL) contained 0.015 or 0.0075 U/μL HIV reverse transcriptase, buffer, 125 nM primer-template complex and various concentrations of Asp-dNMP or dNTP. A concentration range of 0.01-1 mM was used for Asp-dNPM and a concentration range of 0.1-10 μM was used for dNTP. Reactions were incubated at 37° C. Reaction times were between 1 and 120 minutes. The kinetic constants V$_{max}$ and K$_M$ were determined from a Michaëlis-Menten plot, using GraphPad Prism version 3.02.

Electrophoresis

All polymerase reactions (3 μL) were quenched by the addition of 10 μL of loading buffer (90% formamide, 0.05% bromophenol blue, 0.05% xylene cyanol and 50 mM EDTA). Samples were heated at 70° C. for 5 minutes prior to analysis by electrophoresis for 2-3 hours at 2000 V on a 0.4 mm 20% denaturing gel in the presence of a 100 mM Tris-borate, 2.5 mM EDTA buffer, pH 8.3. Products were visualized by phosphor imaging. The amount of radioactivity in the bands corresponding to the products of enzymatic reactions was determined by using the Optiquant image analysis software (Perkin Elmer).

In this example 4, we demonstrate that the L-aspartyl (1) and the L-histidyl (6) derivatives of dAMP can function as a substrate for human immunodeficiency virus reverse transcriptase type 1 (HIV-RT) and that chain elongation is possible. These experiments demonstrate that the polymerase enzyme is able to catalyse the cleavage of the relatively stable P—N bond and that an amino acid can be used as leaving group during the polymerization reaction.

In order to further characterize the potentiality of this leaving group, we studied the substrate properties L-Asp-dGMP (9), L-Asp-dTMP(10) and L-Asp-dCMP(11) for HIV-RT. Thus, the present work focuses on the ability of HIV RT to incorporate aspartic acid derivatives of 2'-deoxyguanosine-5'-monophosphate, 2'-deoxythymidine-5'-monophosphate, and 2'-deoxycytidine-5'-monophosphate into a growing DNA chain.

Kinetic analysis of L-Asp-dAMP (1) incorporation (in example 3) showed that the incorporation efficiency of this substrate by HIV RT was lower than that for the natural substrate (dATP). Therefore, we considered the possibility of activating the nucleoside monophosphate with modified aspartic acid derivatives. In this regard, we focused first attention on N-methyl-L-aspartic acid as leaving group. Thus, 2'-deoxyadenosine-5'-N-methylaspartyl phosphoramidate (12) was synthesized from 2'-deoxyadenosine-5'-monophosphate and N-methyl-L-aspartic acid methyl ester according a method well known in the art.

The ability of HIV RT to incorporate 5'-N-methylaspartyl phosphoramidate 12 into a growing DNA chain was explored in a first series of gel-based single-nucleotide-incorporation assays with primer P1 and template T1 (FIG. 14, panel I). Compound 12 is incorporated into the growing DNA strand but without base-pairing selectivity, since it is easily misincorporated opposite a cytosine base to form the corresponding n+2 product. The same infidelity in incorporation profile was found using lower polymerase concentration. The behavior of 12 is in contrast with that of the L-aspartic acid derivative 1, which inserted selectively against thymine to give the n+1 product (as shown in example 3). When we carried out a control experiment with 12 and a mismatch sequence (A against A, P1T4, see FIG. 15, panel I), phosphoramidate 12 misincorporated against adenine. Compound 12 is a good substrate for HIV-RT, but it shows reduced selectivity compared to other L-aspartic acid derivatives in these experiments. However, the incorporation of this compound 12 resembles most the properties of the natural substrate (dATP); thus compounds like 2'-deoxyadenosine-5'-N-methylaspartyl phosphoramidate (12) could be the best phosphate-modified nucleosides of the invention.

L-Asp-dGMP (9), L-Asp-dTMP (10), and L-Asp-dCMP (11) were synthesized according to a previously reported method. A series of gel-based single-nucleotide-incorporation assays was carried out (FIG. 14), by using primer P1 and template T2 for guanine (9, Panel II), P1 and T4 for thymine (10, Panel III), and P2 and T4 for cytidine (11, Panel IV). As shown before for L-Asp-dAMP (1) in example 3, these three phosphoramidate analogues are recognized by HIV RT and are efficiently incorporated with base-pairing selectivity into the corresponding growing strand, resulting in 92% (9), 95% (10), and 82% (11) conversion to a n+1 strand in 60 min (500 µM nucleotide concentration). It is interesting to note that no incorporation was observed when HIV RT was replaced for M-MLV reverse transcriptase, AMV reverse transcriptase and Φ-DNA polymerase.

In order to confirm that the former observations were due to a true base-pair extension instead to an extendase/terminal transferase activity we tried to extend a blunt ended duplex. With this purpose we carried out a third series of gel-based single-nucleotide-incorporation experiments with primer P1, template A (see FIG. 15) and phosphoramidates 1, 9, 10 and 11. As expected, none of these compounds incorporated at all into the growing DNA strand. Furthermore, control experiments with a mismatch sequence (G against A, P1T4, 9; T against C, P1T2, 10; C against T, P1T1, 11; see FIG. 15) confirmed a true base-pair extension, since primer elongation was not observed.

The efficiency of incorporation by HIV RT of compounds 9, 10, and 11 was investigated by determination of the kinetic parameters $K_M$ and $V_{max}$. As observed for 1 before (as described in example 3), steady-state kinetic analysis (Table 3) of 9, 10 and 11 incorporation indicated that, although $K_M$ for the aspartic acid phosphoramidate analogues is significantly higher than for the natural substrates, the measured $V_{max}$ is only 9-13 fold lower. These data suggest fast and efficient nucleophilic displacement of the amino acid moiety once the aspartic acid phosphoramidate is bound at the active site.

TABLE 3 kinetics of incorporation of phophoramidates 9, 10 and 11 by HIV RT

| Substrate | $V_{max}$ (pmolmin$^{-1}$U) | $K_M$ (µM) | $V_{max}/K_M$ (×10$^6$) |
|---|---|---|---|
| dGTP | 28.81 ± 1.55 | 0.54 ± 1.55 | 53.4 |
| 9 | 2.143 ± 0.13 | 168.8 ± 27.93 | 0.013 |
| dTTP | 30.82 ± 1.44 | 0.53 ± 0.07 | 58.2 |
| 10 | 2.33 ± 0.22 | 288.2 ± 61.72 | 0.008 |
| dCTP | 5.62 ± 0.80 | 3.74 ± 0.95 | 1.5 |
| 11 | 0.59 ± 0.04 | 130.8 ± 19.8 | 0.005 |

Next, we analyzed the ability of HIV RT to direct template dependent selective incorporation of more than one different phosphoramidate nucleosides. For this purpose, primer P1 and template T2 containing an overhang of one cytidine and four thymine nucleobases at the 3' end were used. The ability of HIV RT to synthesize a DNA sequence with L-Asp-dGMP (9) and L-Asp-dAMP (1) was tested (FIG. 16). We carried out first the incorporation of 9 into the growing primer DNA strand. After complete conversion to the n+1 product (two hours), compound 1 was added and the reaction was followed for two more hours. At this time, the n+2 product predominated over the n+1 product (80% vs 20%). In these experiments, stalling of the HIV RT appeared after incorporation of two nucleotides. To confirm that the n+2 product formation is due to adenine incorporation instead of guanine misincorporation a control experiment was carried out. Primer P1, template T2 and compound 9 were used and the reaction was followed for four hours. As expected, no misincorporation was observed, the n+1 conversion at 4 hours is the same as observed at 2 hours (95% incorporation).

Example 5

Synthesis of Phosphoramidates and Phosphodiesters

The synthesis of the methyl esters of the phosphate-modified nucleosides of the invention was accomplished according to the method described by Wagner et al. in *Mini-Rev. Med.*

*Chem.* (2004) 4:409, starting from a nucleoside monophosphate. Deprotection of the methyl esters was carried out with potassium carbonate in methanol-water solution.

The synthesis of compounds 22-24, the structural representation of which is shown in FIG. 17, was carried out in two steps involving the production of ester intermediates according to the following detailed procedure.

Synthesis of an ester intermediate, e.g. 2'-deoxyadenosine-5'-(dimethyl 5-amino-isophthalic acid) phosphoramidate In a two-neck flask, 2'-deoxyadenosine-5'-monophosphoric acid hydrate (50 mg, 0.1 mmole), 5-amino-isophthalic acid dimethyl ester hydrochloride (245 mg, 1 mmole) and dicyclohexylcarbodiimide (DCC) (147 mg, 0.7 mmol) were dissolved under argon atmosphere in a mixture of tent-butanol (3 mL) and $H_2O$ (1 mL). A few drops of triethylamine ($Et_3N$) were added to facilitate dissolution. The reaction mixture was refluxed carefully for 6 hours while stirring under argon atmosphere. The progress of the reaction was monitored by thin layer chromatography (TLC) (using a iPrOH:$H_2O$:$NH_3$ 7:2:1 eluent mixture). The reaction mixture was cooled down and the solvent was removed by rotary evaporation at 37° C. The resulting product was isolated by silica column chromatography eluting with a $CHCl_3$:MeOH:$H_2O$ mixture:gradient (5:1; 5:2:0.25; 5:3:0.5) affording a white solid (35 mg, 47% yield) which was characterized as follows:

$^1$H NMR (300 MHz, $D_2O$): 7.97 (s, 1H, $H_8$), 7.94 (s, 1H, $H_{iPA}$), 7.61 (s, 1H, $H_2$), 7.44 (s, 2H, $H_{iPA}$), 6.25 (t, $J_{H1'-H2'}$=6.6 Hz, 1H, $H_{1'}$), 4.67 (m, 1H, $H_{3'}$), 4.32 (m, 1H, $H_{4'}$), 4.08 (m, 2H, $H_{5'}$), 3.9 (s, 6H, $CH_3$), 2.85 (m, 1H, $H_{2'}$), and 2.53 (m, 1H, $H_{2''}$);

$^{13}$C NMR (75 MHz, $D_2O$): 167.8, 154.6, 151.8, 147.9, 142.4, 139.7, 129.6, 121.7, 86.1, 83.9, 71.1, 65.2, 58.8, 52.7, 46.6, and 38.2;

$^{31}$P NMR (121 MHz, $D_2O$): 0.22 ppm; and
MS (ESI): [M-H]=521.8, calculated for $C_{20}H_{23}N_6O_9P$=522.4.

Synthesis of 2'-deoxyadenosine-5'(5-aminoisophthalic acid) phosphoramidate (23) by deprotecting the ester intermediate A solution (1 mL) of 1.3 M $K_2CO_3$ (MeOH:$H_2O$ 2:1) was added to 2'-deoxyadenine-5'-(dimethyl 5-aminoisophthalic acid) phosphoramidate (35 mg, 67 nmoles) and the deprotection reaction was carried out at room temperature while stirring under argon atmosphere for 4 hours. The course of the reaction was monitored by TLC (using a iPrOH:$H_2O$:$NH_3$ 7:2:1 eluent mixture). Once the starting material has disappeared, the reaction mixture was neutralised by addition of 2M TEAB. The solvent was removed under reduced pressure and the resulting residue was dried by lyophilisation. The resulting product was purified by silica column chromatography eluting with (iPrOH:$H_2O$:$NH_3$) gradient, isolated and concentrated by lyophilisation to provide a white solid (20 mg, 60% yield) which was characterized as follows:

$^1$H NMR (300 MHz, $D_2O$): 8.08 (s, 1H, $H_8$), 8.00 (s, 1H, $H_2$), 7.59 (s, 1H, $H_{iPA}$), 7.31 (s, 2H, $H_{iPA}$), 6.29 (t, $J_{H1'-H2'}$=6.6 Hz, 1H, $H_{1'}$), 4.55 (m, 1H, $H_{3'}$), 4.22 (m, 1H, $H_{4'}$), 4.00 (m, 2H, $H_{5'}$), 2.80 (m, 1H, $H_{2'}$), and 2.45 (m, 1H, $H_{2''}$);

$^{13}$C NMR (75 MHz, $D_2O$): 172.7, 153.7, 150.4, 148.0, 141.4, 140.0, 135.1, 121.0, 119.9, 85.9, 84.0, 71.0, 64.3, and 38.4;

$^{31}$P NMR (121 MHz, $D_2O$): -0.83 ppm; and calculated for $C_{18}H_{19}N_8O_8P$=494.4, MS (ESI) found: [M-H]=493.6.

2'-deoxyadenosine-5'-(dimethyl 5-hydroxy-isophthalic acid) phosphodiester

This ester intermediate was obtained (62 mg, 79% yield) by a similar synthetic procedure as above, and was characterized as follows:

$^1$H NMR (300 MHz, $D_2O$): 8.23 (s, 1H, $H_8$), 8.06 (s, 1H, $H_2$), 8.00 (s, 1H, $H_{iPA}$) 7.68 (s, 2H, $H_{iPA}$), 6.40 (t, $J_{H1'-H2'}$=6.7 Hz, 1H, $H_{1'}$), 4.4 (m, 1H, $H_{3'}$), 4.27 (m, 1H, $H_{4'}$), 4.00 (m, 2H, $H_{5'}$), 3.9 (s, 3H, $CH_3$), 3.8 (s, 3H, $CH_3$), 2.90 (m, 1H, $H_{2'}$), and 2.56 (m, 1H, $H_{2''}$);

$^{13}$C NMR (75 MHz, $D_2O$): 166.9, 151.8, 151.6, 151.6, 139.9, 130.6, 125.6, 125.3, 85.9, 83.9, 71.2, 65.9, 52.9, and 38.2;

$^{31}$P NMR (121 MHz, $D_2O$): -5.05 ppm; and
MS (ESI): [M-H]=522.3, calculated for $C_{20}H_{22}N_5O_{10}P$ 523.11, found 522.20.

2'-deoxyadenosine-5'-(5-hydroxy-isophthalic acid) phosphodiester (22)

This compound was obtained (25 mg, 66% yield) from the above ester intermediate, and was characterized as follows:

$^1$H NMR (300 MHz, $D_2O$): 8.23 (s, 1H, H8), 8.1 (s, 1H, H2), 7.7 (s, 1H, $H_{iPA}$), 7.6 (s, 2H, $H_{iPA}$), 6.46 (t, $J_{H1'-H2'}$=6.7 Hz, 1H, $H_{1'}$), 4.65 (m, 1H, $H_{3'}$), 4.32 (m, 1H, $H_{4'}$), 4.19 (t, 2H, $H_{5'}$), 2.84 (m, 1H, $H_{2'}$), and 2.56 (m, 1H, $H_{2''}$);

$^{13}$C NMR (75 MHz): 173.7, 155.0, 151.8, 151.7, 149.0, 140.6, 137.5, 125.3, 123.4, 119.0, 96.5, 84.7, 71.8, 66.1, and 38.8;

$^{31}$P NMR (121 MHz, solvent): -4.4 ppm; and
MS (ESI): [M-H]=494.3, calculated for $C_{18}H_{19}N_6O_9P$ 495.08.

2'-deoxyadenosine-5'-(dimethyl 4-hydroxy-phthalic acid) phosphodiester

This ester intermediate was obtained (70 mg, 93% yield) by a similar synthetic procedure as above, and was characterized as follows:

$^1$H NMR (300 MHz, $D_2O$): 8.12 (s, 1H, $H_3$), 8.09, (s, 1H, $H_2$), 7.48 (d, 1H, $H_{PA}$), 7.16 (d, 1H, $H_{PA}$), 7.13 (s, 1H, $H_{PA}$), 6.4 (t, $J_{H1'-H2'}$=6.8 Hz, 1H, $H_{1'}$), 4.70 (m, 1H, $H_{3'}$), 4.31 (m, 1H, $H_{4'}$), 4.21 (m, 2H, $H_{5'}$), 3.9 (s, 3H, $CH_3$), 3.8 (s, 3H, $CH_3$), 2.81 (m, 1H, $H_{2'}$), and 2.54 (m, 1H, $H_{2''}$);

$^{13}$C NMR (75 MHz, $D_2O$): 169.4, 168.5, 154.3, 154.2, 150.4, 148.2, 140.2, 133.1, 130.8, 124.7, 122.6, 119.9, 118.4, 85.9, 84.0, 71.0, 65.8, 53.3, 53.1, and 38.5;

$^{31}$P NMR (121 MHz, $D_2O$): -5.42 ppm; and
MS (ESI): [M-H]=522.3.

2'-deoxyadenosine-5'-(4-hydroxy-phthalic acid) phosphodiester (24)

This compound was obtained (25 mg, 66% yield) from the above ester intermediate, and was characterized as follows:

$^1$H NMR (300 MHz, $D_2O$): 8.32 (s, 1H, $H_8$), 8.21 (s, 1H, $H_2$), 7.33 (d, 1H, $H_{PA}$), 7.12 (s, 1H, $H_{PA}$), 6.92 (d, 1H, $H_{PA}$), 6.49 (t, $J_{H1'-H2'}$=6.7 Hz, 1H, $H_{1'}$), 4.68 (m, 1H, $H_{3'}$), 4.30 (m, 1H, $H_{4'}$), 4.17 (m, 2H, $H_{5'}$), 2.88 (m, 1H, $H_{2'}$), and 2.61 (m, 1H, $H_{2''}$);

$^{13}$C NMR (75 MHz, $D_2O$): 176.0, 175.2, 155.5, 152.42, 148.7, 139.8, 129.5, 119.5, 118.8, 85.6, 83.9, 71.2, 65.7, and 38.6;

$^{31}$P NMR (121 MHz, D$_2$O): −4.6 ppm; and
High resolution MS (ESI): m/z calculated for C$_{18}$H$_{19}$N$_6$O$_9$P 495.08, found 496.83.

Example 6

Single Incorporation

HIV-1 Reverse Transcriptase serves, in the HIV-1 viral replication process, as a catalyst and uses deoxynucleotides as substrates. This polymerase is error-prone and thus has a high mutation rate. Here, we evaluated the capacity to incorporate a deoxyadenosine nucleoside into the primer-template complex P1T1 using HIV-1 RT, and some of the above described illustrative compounds of the invention, carrying different leaving groups, as substrates. The initial screening was carried out using a template with an overhang of one thymidine nucleotide followed by three non-pyrimidine bases (Table 1). Incorporation efficiency was analysed by the polyacrylamide gel-based single nucleotide incorporation assay.

TABLE 1 primer-template complexes used in DNA polymerase reactions. bold letters indicate the template overhang in the hybridized primer-template duplex.

Single nucleotide incorporation and Kinetic experiments

SEQ ID NO: 1    P1    5'-CAGGAAACAGCTATGAC-3'

SEQ ID NO: 2    T1    3'-GTCCTTTGTCGATACTGTCCCC-5'

The isophthalic acid-derived phosphodiester (22) was recognized by HIV-1 RT and efficiently incorporated into a growing primer strand (as shown in FIG. 18) with a conversion to an n+1 strand 90-92% (22) over a period of 2 hours at 1 mM concentration. The corresponding anilino-derived phosphate nucleoside (23) was less well recognized as substrate. Finally, little incorporation (13% n+1 product after 2 hours) was observed with the phthalic acid dAMP derivative (24).

A few interesting observations can be drawn from this first panel. Despite the geometric constraint brought by the aromatic ring, dicarboxylated phenol and dicarboxylated aniline can still function as leaving groups in a polymerase catalyzed reaction. A phenolate is a better leaving group than the corresponding aniline anion, although it is unclear whether protonation of the nitrogen atom of the anilino group may be involved in the catalytic mechanism.

Among the two substituted phenol moieties, the one carrying both carboxyl substituents in meta position (22) is more successful than the one carrying the carboxyl substituents in meta and para positions respectively (24). This indicates that the orientation of both carboxyl functions is important, which might be attributed to steric hindrance in the active site of the polymerase, or to more specific chelating properties. Compound (22) was further evaluated at different concentrations (as shown in FIG. 19). At 500 μM compound 2 displayed 75% of n+1 formation, which represents 88% of L-Asp-dAMP capacity.

We also tested the possibility of a polymerase independent incorporation, but no compound was incorporated in the absence of the enzyme.

Example 7

Oligodeoxyribonucleotides P1, T1, T2 and T3 were purchased from Sigma Genosys. The concentrations were determined with a Varian Cary-300-Bio UV Spectrophotometer.

The lyophilized oligonucleotides were dissolved in diethylpyrocarbonate (DEPC)-treated water and stored at −20° C. The primer oligonucleotides were 5'-$^{33}$P-labeled with 5'-[γ$^{33}$P]-ATP (Perkin Elmer) using T4 polynucleotide kinase (New England Biolabs) according to standard procedures. The labeled oligonucleotide was further purified using Illustra™ Microspin™ G-25 columns (GE Healthcare).

DNA Polymerase Reactions

End-labeled primer was annealed to its template by combining primer and template in a molar ratio of 1:2 and heating the mixture to 70° C. for 10 minutes followed by slow cooling to room temperature over a period of 1.5 hour. For the incorporation of 1, 2, 3, 4, 5 and 6, a series of 20 μL-batch reactions was performed with the enzyme HIV-1 RT (Ambion, 10 U/μL stock solution, specific activity 8.095 U/mg, concentration 1.2 mg/mL). The final mixture contained 125 nM primer template complex, RT buffer (250 mM Tris.HCl, 250 mM KCl, 50 mM MgCl$_2$, 2.5 mM spermidine, 50 mM dithiothreitol (DTT); pH 8.3), 0.025 U/μL HIV-1 RT, and different concentrations of phosphoramidate or phosphodiester building blocks (1 mM, 500 μM, 200 μM and 100 μM respectively). In the case of the aromatic phosphate-modified nucleosides 23 and 24, the range of concentrations was limited to 1 mM. In the control reaction with the natural nucleotide, a 10 μM dATP concentration was used. The mixture was incubated at 37° C. and 2.5 μL aliquots were quenched after 5, 10, 20, 30, 60 and 120 minutes. Results are shown in FIG. 18.

Example 8

In an attempt to further simplify the structure of the leaving group, we investigated the pyrophosphate mimicking ability of a group carrying only one carboxylic acid unit, for both the phosphoramidate nucleoside β-Ala-dAMP (a) and the phosphodiester nucleoside glycolic acid-dAMP (b) structurally shown below.

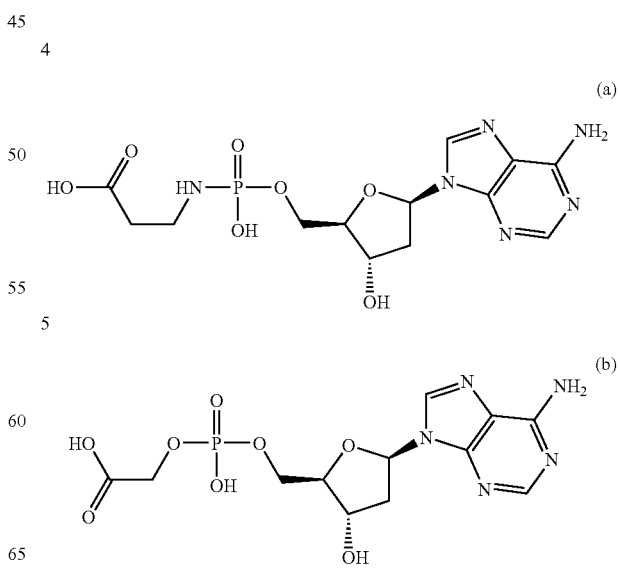

Synthesis of Phosphoramidates and Phosphodiesters

For the synthesis of glycolic acid dAMP (b), a method of divalent cation assisted coupling, as shown in the scheme below (wherein NEM stands for N-ethyl morpholine) and previously suggested by Sawai in *Bull. Chem. Soc.* (1990) 63:692-696, was used. In this approach, the carboxyl acid moiety does not need to be protected since it serves as a ligand for the divalent metal-ion during the nucleotidyl transfer, thus requiring one single synthetic step. The desired phosphodiester nucleoside was obtained in a 41% yield (after high performance liquid chromatography purification).

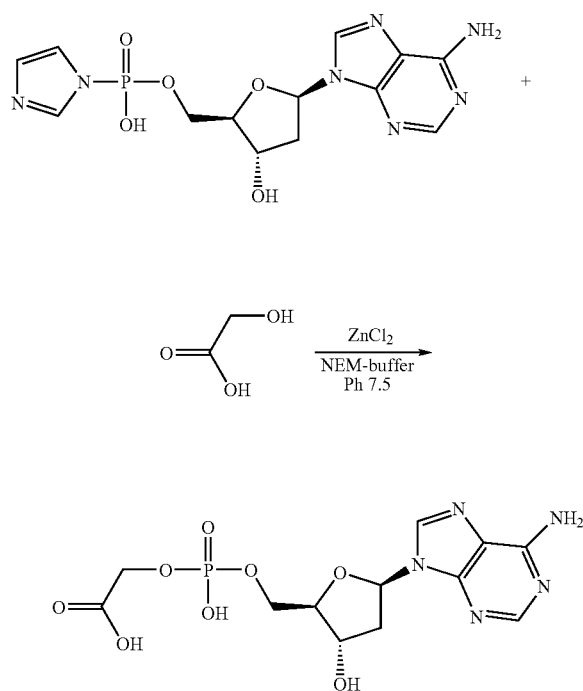

Example 9

Single Incorporation

Using the glycolic acid dAMP phosphodiester (b) of example 8 (GA-dAMP), the incorporation efficiency into P1T1 by HIV-1 reverse Transcriptase was moderate, as n+1 formation was observed up to 68% at a concentration of 500 µM as shown in FIG. 20. This shows that, in the case of a phosphodiester bond between the nucleoside monophosphate and the leaving group, one carboxylic acid function on the leaving group is enough to enable the nucleotidyl transfer reaction.

Example 10

2'-deoxyadenosine-5'-β-alanine phosphoramidate methyl ester

This compound was obtained (172 mg, 81% yield) and characterized as follows:

$^1$H NMR (500 MHz, CD$_3$OD): 8.5 (s, 1H, H$_8$); 8.2 (s, 1H, H$_2$); 6.5 (t, $^3J_{H1'-H2'}$=7.0 Hz, 1H, H$_{1'}$); 4.7 (m, 1H, H$_{3'}$); 4.2 (m, 1H, H$_{4'}$); 4.08-3.98 (m, 2H, H$_{5'}$); 3.64 (s, 3H, —O—CH$_3$); 3.14-3.10 (m, 2H, CH$_{2L}$); 2.84-2.80 (m, 1H, H$_{2'}$); and 2.47-2.45 (m, 3H, H$_2$'', CH$_{2L}$) ppm;

$^{13}$C NMR (125 MHz, CD$_3$OD): 173.3, 155.9, 152.4, 149.0, 139.7, 118.7, 86.6, 83.9, 71.7, 64.1, 50.6, 39.9, 37.2, and 35.9 ppm;

$^{31}$P NMR (202 MHz, CD$_3$OD): 7.53 ppm; and high resolution MS (ESI): m/z calculated for C$_{14}$H$_{21}$N$_8$O$_7$P 416.12, found 415.11.

2'-deoxyadenosine-5'-β-alanine phosphoramidate (a)

This compound was obtained (15 mg, 87% yield) and characterized as follows:

$^1$H NMR (500 MHz, D$_2$O): 8.2 (s, 1H, H$_8$), 7.8 (s, 1H, H$_2$), 6.2 (t, $^3J_{H1'-H2'}$=6.6 Hz, 1H, H$_{1'}$), 4.6 (m, 1H, H$_3$—), 4.1 (m, 1H, H$_{4'}$), 3.8 (m, 2H, H$_{5'}$), 2.8 (m, 2H, CH$_{2\beta}$), 2.7 (m, 1H, H$_{2'}$), 2.5 (m, 1H, H$_{2''}$), and 2.1 (t, J$_{H\alpha-H\beta}$6.0 Hz, 2H, CH$_{2\alpha}$) ppm;

$^{13}$C NMR (125 MHz, D$_2$O): 178.1, 154.3, 151.0, 148.3, 140.0, 118.7, 85.7, 83.5, 70.9, 63.6, 38.5 (2C), and 37.1 ppm;

$^{31}$P NMR (202 MHz, D$_2$O): 8.75 ppm; and high resolution MS (ESI): m/z calculated for C$_{13}$H$_{19}$N$_8$O$_7$P 402.105 found 401.098.

2'-deoxyadenosine-5'-(glycolic acid) phosphodiester (b)

The imidazolate of deoxyadenosine monophosphate was synthesised according to the procedure of Lohrmann et al. in *Tetrahedron* (1978) 34:853. A solution of deoxyadenosine monophosphate imidazolate (20 mg, 50 µmole), hydroxyl acetic acid (7.6 mg, 1 mmole), zinc chloride (7 mg, 50 µmoles) in 2 mL N-ethylmorpholine aqueous buffer 0.2 M (pH 7.5) was stirred under argon atmosphere at room temperature for 1 day. Reaction was monitored by TLC (using a iPrOH:H$_2$O:NH$_3$ 7:2:1 eluent mixture), quenched with an EDTA 0.25 M solution in order to break-down the nucleotide-metal complex, and finally lyophilized affording a white solid (yield 42%). This product was isolated after HPLC purification on a PLRP-S column (100 Å 8 µm, 300*7.5 mm, Polymer Laboratories) running a gradient of acetonitrile in 50 nM triethylammonium acetate buffer, and characterized as follows:

$^{31}$P NMR (121 MHz): −0.09 ppm; and

MS ESI [M−H] 388.2, calculated for C$_{12}$H$_{16}$N$_8$O$_8$P=389.3.

Other Embodiments

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. A phosphate-modified nucleoside represented by the structural formula (I)

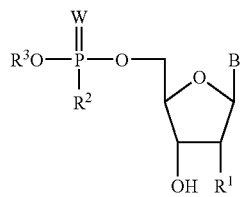

wherein
B is a pyrimidine or purine base, or an analogue thereof, optionally substituted with one or two substituents independently selected from the group consisting of halogen, hydroxyl, sulfhydryl, methyl, ethyl, amino and methylamino;
$R^1$ is H or OH;
$R^3$ is hydrogen;
W is O or S; and
$R^2$ is a group represented by the structural formula IV:

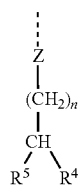

wherein
n is 0
Z is selected from the group consisting of O, S, NH and $NCH_3$;
each of $R^4$ and $R^5$ is independently selected from the group consisting of $(CH_2)_m$—$COOR^6$ and $(CH_2)_m$-imidazolyl;
$R^6$ is H or $C_{1-6}$ alkyl;
m is 0 or 1; and
dotted lines represent the point of attachment of Z to the phosphorous atom of formula (I);
or the structural formula (I'):

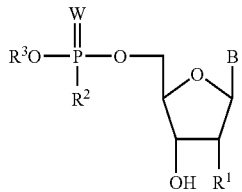

wherein
B is a pyrimidine or purine base, or an analogue thereof, optionally substituted with one or two substituents independently selected from the group consisting of halogen, hydroxyl, sulfhydryl, methyl, ethyl, isopropyl, amino, methylamino, ethylamino, trifluoromethyl and cyano;
$R^1$ is hydrogen or hydroxyl;
$R^3$ is selected from the group consisting of hydrogen, $C_{1-6}$ alkyl, $C_{3-6}$ cycloalkyl, aryl-$C_{1-6}$alkyl and 2-cyanoethyl, wherein said $C_{1-6}$ alkyl, $C_{3-6}$ cycloalkyl or aryl-$C_{1-6}$ alkyl is optionally substituted with one or more, preferably 1, 2 or 3, substituents independently selected from the group consisting of halogen, hydroxyl, $C_{1-6}$ alkoxy, trifluoromethyl, trifluoromethoxy, nitro, cyano and amino;
W is O; and
$R^2$ is a group represented by the structural formula (VI)

wherein
dotted lines represent the point of attachment of Z to the phosphorous atom of formula (I');
n is 0, 1 or 2;
Z is selected from the group consisting of O, S, NH and $NCH_3$; and
Ar is an aryl group;
and stereoisomers, enantiomers and pharmaceutically acceptable salts thereof, provided that said phosphate-modified nucleoside is not:

N-5'-adenylylphosphoramidate L-aspartic acid 1,4-dimethyl ester,
N-5'-uridylylphosphoramidate L-aspartic acid 1,4-dimethyl ester,
N-5'-thimidylylphosphoramidate L-aspartic acid 1,4-dimethyl ester,
N-5'-adenylylphosphoramidate L-aspartic acid 1,4-dimethyl ester, monoammonium salt,
N-5'-guanylylphosphoramidate L-aspartic acid 1,4-dimethyl ester, monoammonium salt,
N-5'-uridylylphosphoramidate L-aspartic acid 1,4-dimethyl ester, monoammonium salt,
N-5'-thymidylylphosphoramidate L-aspartic acid 1,4-dimethyl ester, monoammonium salt,
N-5'-citidylylphosphoramidate L-aspartic acid disodium salt,
N-5'-uridylylphosphoramidate L-histidine,
N-5'-uridylylphosphoramidate L-histidine 1-methyl ester,
N-5'-adenylylphosphoramidate L-histidine 1-methyl ester,
N-5'-cytidylylphosphoramidate L-histidine 1-methyl ester, or
N-5'-uridylylphosphoramidate L-aspartic acid.

2. The phosphate-modified nucleoside of claim 1, wherein $R^4$ is COOH and $R^5$ is selected from the group consisting of $CH_2$—COOH and $CH_2$-(3H-imidazol-4-yl).

3. A phosphate-modified nucleoside selected from the group consisting of 2'-deoxy-adenosine-5'-aspartyl-phosphoramidate (Asp-dAMP); 2'-deoxy-cytidine-5'-aspartyl-phosphoramidate (Asp-dCMP); 2'-deoxy-guanosine-5'-aspartyl-phosphoramidate (Asp-dGMP); 2'-deoxy-thymidine-5'-aspartyl-phosphoramidate (Asp-dTMP); 2'-deoxy-uridine-5'-aspartyl-phosphoramidate (Asp-dUMP); adenosine-5'-aspartyl-phosphor-amidate (Asp-AMP); cytidine-5'-aspartyl-phosphoramidate (Asp-CMP); guanosine-5'-aspartyl-phosphoramidate (Asp-GMP); 5-methyluridine-5'-aspartyl-phosphoramidate (Asp-m5 uMP); uridine-5'-aspartyl-phosphoramidate (Asp-UMP); 2'-deoxy-adenosine-5'-histidyl-phosphoramidate (His-dAMP); 2'-deoxy-cytidine-5'-histidyl-phosphoramidate (His-dCMP); 2'-deoxy-guanosine-5'-histidyl-phosphoramidate (His-dGMP); 2'-deoxy-thymidine-5'-histidyl-phosphoramidate (His-dTMP); 2'-deoxy-uridine-5'-histidyl-phosphoramidate (His-dUMP); adenosine-5'-histidyl-phosphoramidate (His-AMP); cytidine-5'-histidyl-phosphoramidate (His-CMP); guanosine-5'-histidyl-phosphoramidate (His-GMP); 5-methyluridine-5'-histidyl-phosphoramidate (His-m5 uMP); uridine-5'-histidyl-phosphoramidate (His-UMP); 5-O-1,3-dicarboxylphenyl-dAMP; 5-NH-1,3-dicarboxylphenyl-dAMP; 4-O-1,2-dicarboxylphenyl-dAMP; 5-O-1,3-dicarboxylphenyl-dCMP; 5-NH-1,3-dicarboxylphenyl-dCMP; 4-O-1,2-dicarboxylphenyl-dCMP; 5-O-1,3-dicarboxylphenyl-dGMP; 5-NH-1,3-dicarboxylphenyl-dGMP; 4-O-1,2-dicarboxylphenyl-dGMP; 5-O-1,3-dicarboxylphenyl-dTMP; 5-NH-1,3-dicarboxylphenyl-dTMP; 4-O-1,2-dicarboxyl-phenyl-dTMP; 5-O-1,3-dicarboxylphenyl-dUMP; 5-NH-1,3-dicarboxylphenyl-dUMP; 4-O-1,2-dicarboxylphenyl-dUMP; 5-O-1,3-dicarboxylphenyl-AMP; 5-NH-1,3-dicarboxyl-phenyl-AMP; 4-O-1,2-dicarboxylphenyl-AMP; 5-O-1,3-dicarboxlphenyl-CMP; 5-NH-1,3-dicarboxylphenyl-CMP; 4-O-1,2-dicarboxylphenyl-CMP; 5-O-1,3-dicarboxyl-phenyl-GMP; 5-NH-1,3-dicarboxylphenyl-GMP; 4-O-1,2-dicarboxylphenyl-GMP; 5-O-1,3-dicarboxylphenyl-TMP; 5-NH-1,3-dicarboxylphenyl-TMP; 4-O-1,2-dicarboxyl-phenyl-TMP; 5-O-1,3-dicarboxylphenyl-UMP; 5-NH-1,3-dicarboxylphenyl-UMP; and 4-O-1,3-dicarboxyl-phenyl-UMP.

4. The phosphate-modified nucleoside of claim 1, wherein said pyrimidine analogue is represented by the structural formula (B):

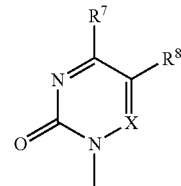

wherein
$R^7$ is selected from the group consisting of —OH, —SH, —$NH_2$, —$NHCH_3$ and —$NHC_2H_5$;
$R^8$ is selected from the group consisting of hydrogen, methyl, ethyl, isopropyl, amino, ethylamino, trifluoromethyl, cyano and halogen; and
X is CH or N.

5. The phosphate-modified nucleoside of claim 4, wherein $R^4$ is COOH and $R^5$ is selected from the group consisting of $CH_2$—COOH and $CH_2$-(3H-imidazol-4-yl).

6. The phosphate-modified nucleoside of claim 1, wherein said purine analogue is represented by the structural formula (D):

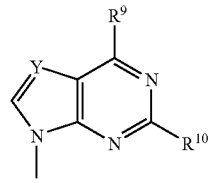

wherein
$R^9$ is selected from the group consisting of H, —OH, —SH, —$NH_2$, and —$NHCH_3$;
$R^{10}$ is selected from the group consisting of hydrogen, methyl, ethyl, hydroxyl, amino and halogen; and
Y is CH or N.

7. The phosphate-modified nucleoside of claim 6, wherein $R^4$ is COOH and $R^5$ is selected from the group consisting of $CH_2$—COOH and $CH_2$-(3H-imidazol-4-yl).

8. A method for preparing an oligonucleotide comprising phosphate-modified nucleosides, comprising the step of incorporating at least one of said phosphate-modified nucleosides into a DNA/RNA strand, wherein said phosphate-modified nucleoside is according to claim 1.

9. The method of claim 8, wherein the oligonucleotide is prepared by DNA/RNA polymerase-dependent amplification.

10. The method of claim 9, wherein said DNA/RNA polymerase-dependent amplification is PCR.

11. The method of claim 8, wherein the oligonucleotide is prepared by administering said phosphate-modified nucleosides to bacteriae comprising a DNA/RNA polymerase.

12. The method of claim 9, wherein said polymerase is from a microorganism or from bacterial or viral origin.

13. The method of claim 9, wherein said polymerase is Therminator DNA polymerase; KF (exo⁻) DNA polymerase or Reverse Transcriptase.

14. The method of claim 13, wherein said polymerase is HIV Reverse Transcriptase.

15. A non-pharmaceutical composition comprising a phosphate-modified nucleoside according to claim 1, an aqueous solution and optionally one or more buffering agents.

16. A pharmaceutical composition comprising a therapeutically effective amount of a phosphate-modified nucleoside according to claim 1, and one or more pharmaceutically acceptable excipients.

17. A pharmaceutical composition according to claim 16, wherein said therapeutically effective amount is a viral polymerase inhibiting amount.

18. A pharmaceutical composition according to claim 16, wherein said therapeutically effective amount is a HIV Reverse Transcriptase inhibiting amount.

19. A method of prevention or treatment of a viral infection in a mammal, comprising the administration of a therapeutically effective amount of a phosphate-modified nucleoside according to claim 1, optionally in combination with one or more pharmaceutically acceptable excipients.

20. The method of claim 19, wherein said viral infection is a HIV infection.

21. The method of claim 19, wherein said mammal is a human being.

22. The phosphate-modified nucleoside of claim 1, being represented by the structural formula (I'), wherein Ar is a phenyl group optionally substituted with one or more substituents independently selected from the group consisting of halogen, amino, trifluoromethyl, hydroxyl, sulfhydryl, nitro, ($C_1$-$C_6$)alkoxy, trifluoromethoxy, cyano and $(CH_2)_q$—COOR, wherein R is hydrogen or ($C_1$-$C_6$) alkyl, and q is 0, 1 or 2.

23. The phosphate-modified nucleoside of claim 1, being represented by the structural formula (I'), wherein $R^3$ is hydrogen and Ar is 1,2-dicarboxylphenyl or 1,3-dicarboxylphenyl.

24. A method for preparing an oligonucleotide comprising phosphate-modified nucleosides, comprising the step of incorporating at least one of said phosphate-modified nucleosides into a DNA/RNA strand, wherein said phosphate-modified nucleoside is according to claim 3.

25. The method of claim 24, wherein the oligonucleotide is prepared by DNA/RNA polymerase-dependent amplification.

26. The method of claim 25, wherein said DNA/RNA polymerase-dependent amplification is PCR.

27. The method of claim 24, wherein the oligonucleotide is prepared by administering said phosphate-modified nucleosides to bacteriae comprising a DNA/RNA polymerase.

28. The method of claim 25, wherein said polymerase is from a microorganism or from bacterial or viral origin.

29. The method of claim 25, wherein said polymerase is Therminator DNA polymerase; KF (exo⁻) DNA polymerase or Reverse Transcriptase.

30. The method of claim 29, wherein said polymerase is HIV Reverse Transcriptase.

31. A non-pharmaceutical composition comprising a phosphate-modified nucleoside according to claim 3, an aqueous solution and optionally one or more buffering agents.

32. A pharmaceutical composition comprising a therapeutically effective amount of a phosphate-modified nucleoside according to claim 3, and one or more pharmaceutically acceptable excipients.

33. A pharmaceutical composition according to claim 32, wherein said therapeutically effective amount is a viral polymerase inhibiting amount.

34. A pharmaceutical composition according to claim 32, wherein said therapeutically effective amount is a HIV Reverse Transcriptase inhibiting amount.

35. A method of prevention or treatment of a viral infection in a mammal, comprising the administration of a therapeutically effective amount of a phosphate-modified nucleoside according to claim 3, optionally in combination with one or more pharmaceutically acceptable excipients.

36. The method of claim 35, wherein said viral infection is a HIV infection.

37. The method of claim 35, wherein said mammal is a human being.

* * * * *

UNITED STATES PATENT AND TRADEMARK OFFICE
CERTIFICATE OF CORRECTION

PATENT NO.         : 8,242,087 B2
APPLICATION NO.    : 12/549117
DATED              : August 14, 2012
INVENTOR(S)        : Adelfinskaya et al.

It is certified that error appears in the above-identified patent and that said Letters Patent is hereby corrected as shown below:

Column 59, Claim 22, Line 29-30, replace "q is 0, 10r 2" with --q is 0, 1 or 2--.

Signed and Sealed this
Sixteenth Day of October, 2012

David J. Kappos
*Director of the United States Patent and Trademark Office*